(12) United States Patent
Sonderegger et al.

(10) Patent No.: US 9,522,229 B2
(45) Date of Patent: Dec. 20, 2016

(54) INFUSION DEVICE WITH AUTOMATIC INSERTION AND INTRODUCER NEEDLE RETRACTION

(75) Inventors: Ralph L. Sonderegger, Farmington, UT (US); Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 49 days.

(21) Appl. No.: 14/002,683

(22) PCT Filed: Feb. 8, 2012

(86) PCT No.: PCT/US2012/000068
§ 371 (c)(1),
(2), (4) Date: Dec. 6, 2013

(87) PCT Pub. No.: WO2012/134588
PCT Pub. Date: Oct. 4, 2012

(65) Prior Publication Data
US 2014/0088509 A1 Mar. 27, 2014

Related U.S. Application Data

(60) Provisional application No. 61/448,975, filed on Mar. 3, 2011, provisional application No. 61/441,258, filed on Feb. 9, 2011.

(51) Int. Cl.
*A61M 5/158* (2006.01)
*A61M 25/02* (2006.01)
(Continued)

(52) U.S. Cl.
CPC ............ *A61M 5/158* (2013.01); *A61M 5/3287* (2013.01); *A61M 25/02* (2013.01);
(Continued)

(58) Field of Classification Search
CPC ............ A61M 2005/1581; A61M 2005/1585; A61M 2005/1587
(Continued)

(56) References Cited

U.S. PATENT DOCUMENTS 4,490,141 A * 12/1984 Lacko .................. A61M 25/02
128/879
6,830,562 B2 12/2004 Mogensen et al.
(Continued)

FOREIGN PATENT DOCUMENTS

EP 2 667 913 12/2013
WO WO 2009/010399 1/2009

OTHER PUBLICATIONS

Nilimedix, "Lighty, The Next Generation in Subcutaneous Infusion Sets", Internet Advertisement, May 10, 2009, pp. 1 and 2.

*Primary Examiner* — Laura Bouchelle
*Assistant Examiner* — Anh Bui
(74) *Attorney, Agent, or Firm* — Dickinson Wright PLLC

(57) ABSTRACT

An infusion device (10) includes one or more of automatic insertion and retraction of an introducer needle (40) and catheter (28), introducer needle safety and extension set. The device (10) can further comprise a top-push button (16) activation feature, a side-push button (402) activation feature or a rotary-button (412) activation feature, and one or more of a manual interlock of an outer barrel and base, and a manual interlock for an extension set top and base. Packaging (500) for an integrated and/or removable inserter with activation button protection is also disclosed.

8 Claims, 58 Drawing Sheets

(51) Int. Cl.
*A61M 25/06* (2006.01)
*A61M 5/32* (2006.01)
A61M 5/00 (2006.01)
A61M 25/00 (2006.01)

(52) U.S. Cl.
CPC ......... *A61M 25/0631* (2013.01); *A61M 5/002* (2013.01); *A61M 25/002* (2013.01); *A61M 2005/1583* (2013.01); *A61M 2005/1585* (2013.01); *A61M 2005/1586* (2013.01); *A61M 2025/028* (2013.01); *A61M 2025/0253* (2013.01)

(58) Field of Classification Search
USPC .... 604/164.01, 164.12, 164.04, 164.07, 513, 604/180
See application file for complete search history.

(56) References Cited

U.S. PATENT DOCUMENTS

| | | |
|---|---|---|
| 7,713,258 B2 | 5/2010 | Adams et al. |
| 2004/0158207 A1* | 8/2004 | Hunn .................... A61M 5/158 604/164.01 |
| 2009/0048578 A1* | 2/2009 | Adams ............... A61M 5/14248 604/513 |
| 2010/0280460 A1* | 11/2010 | Markussen ......... A61M 5/2033 604/195 |
| 2010/0298830 A1* | 11/2010 | Browne ............. A61B 17/1615 606/79 |
| 2012/0136310 A1* | 5/2012 | Kadamus ............. A61M 5/158 604/164.04 |

\* cited by examiner

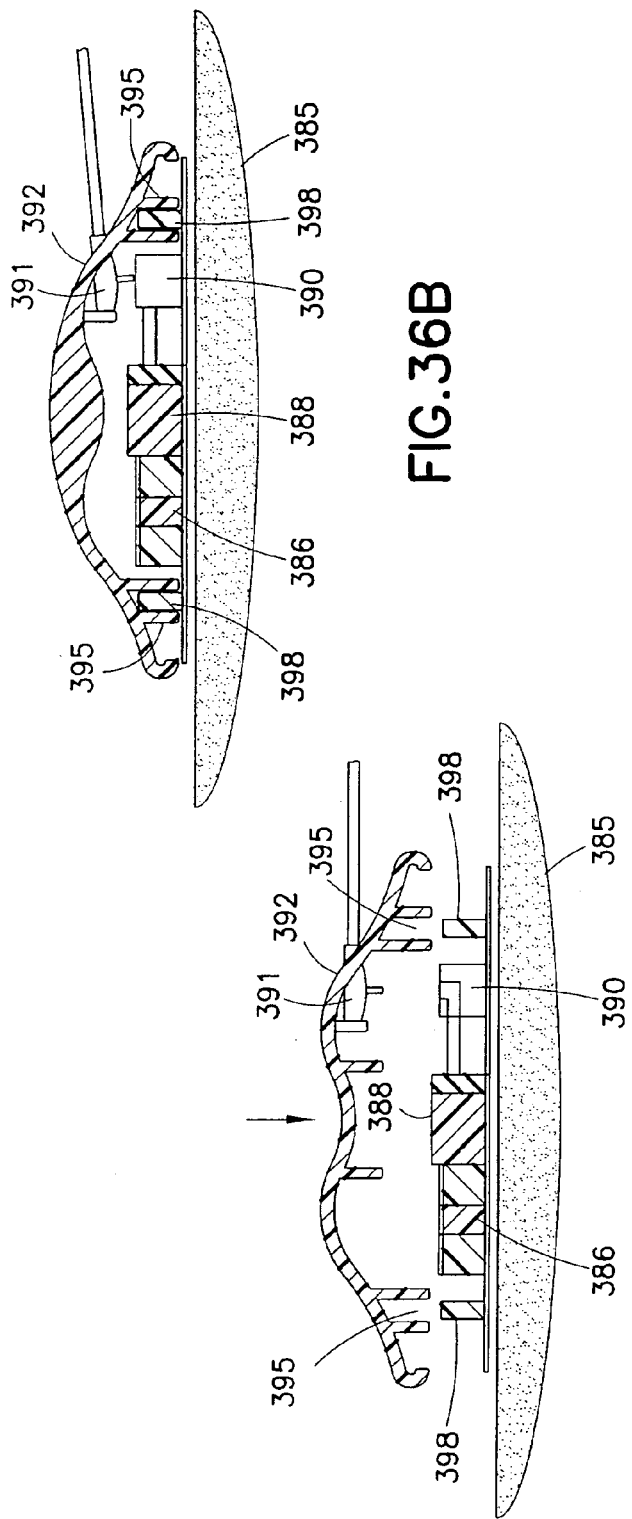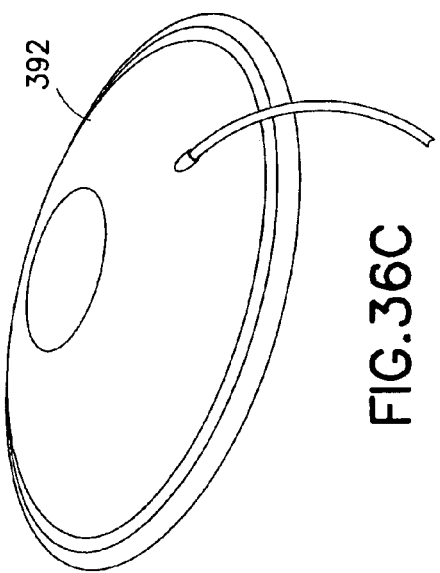

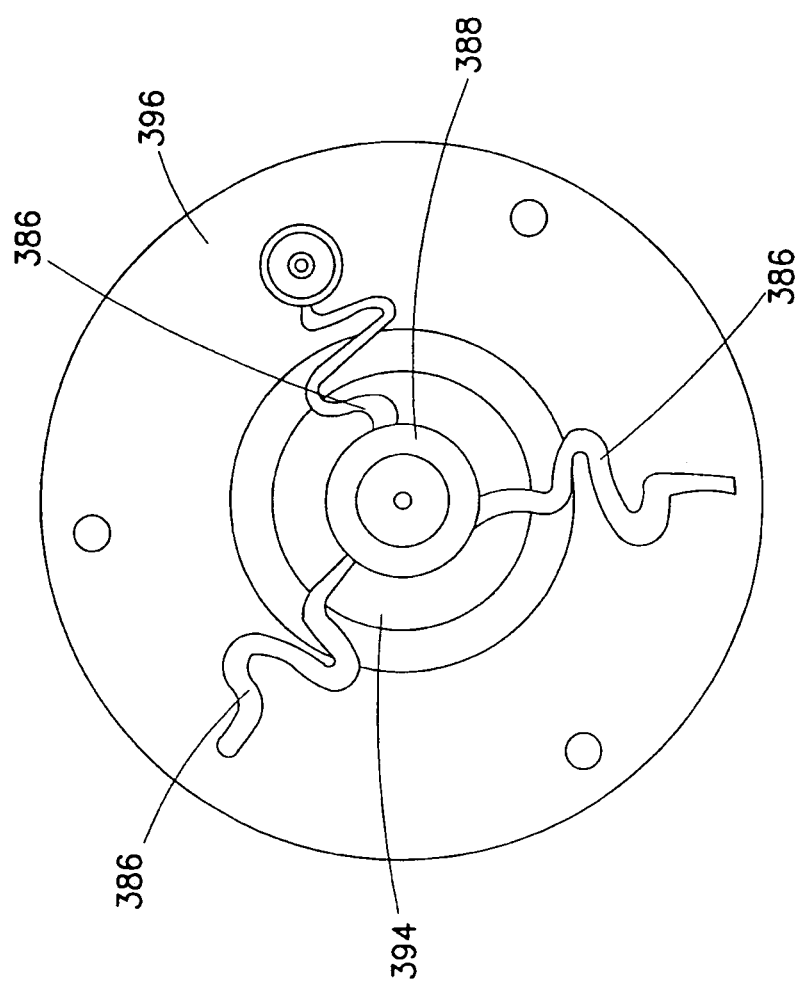

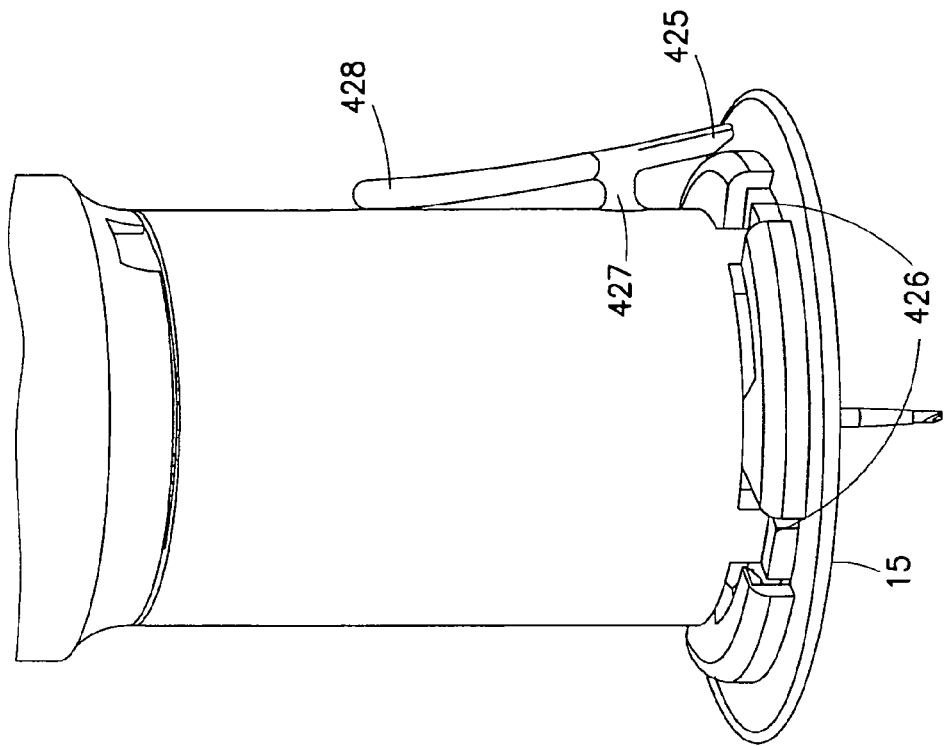
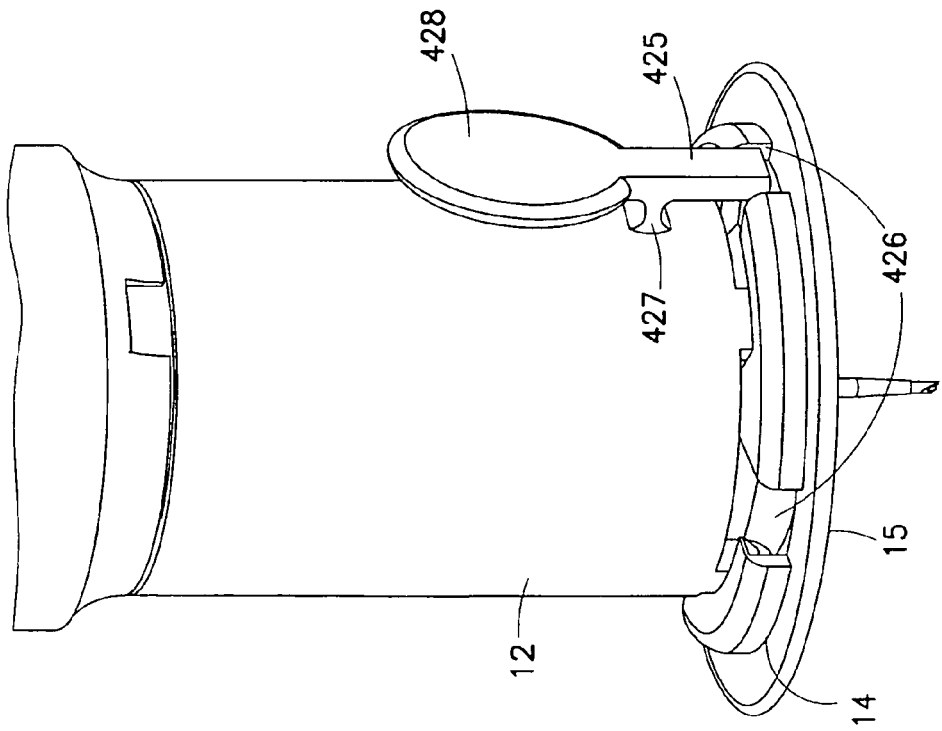

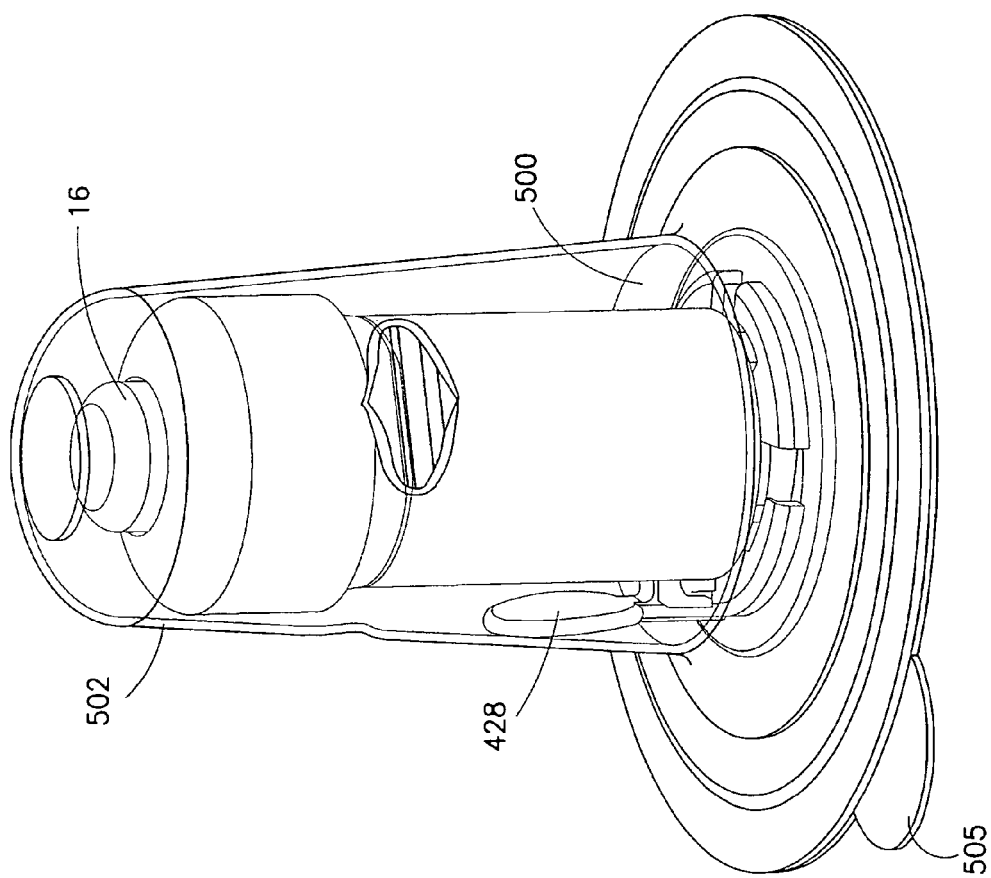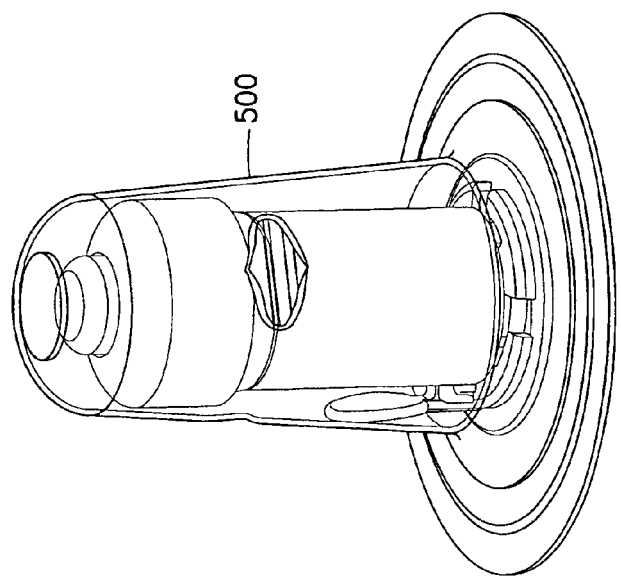

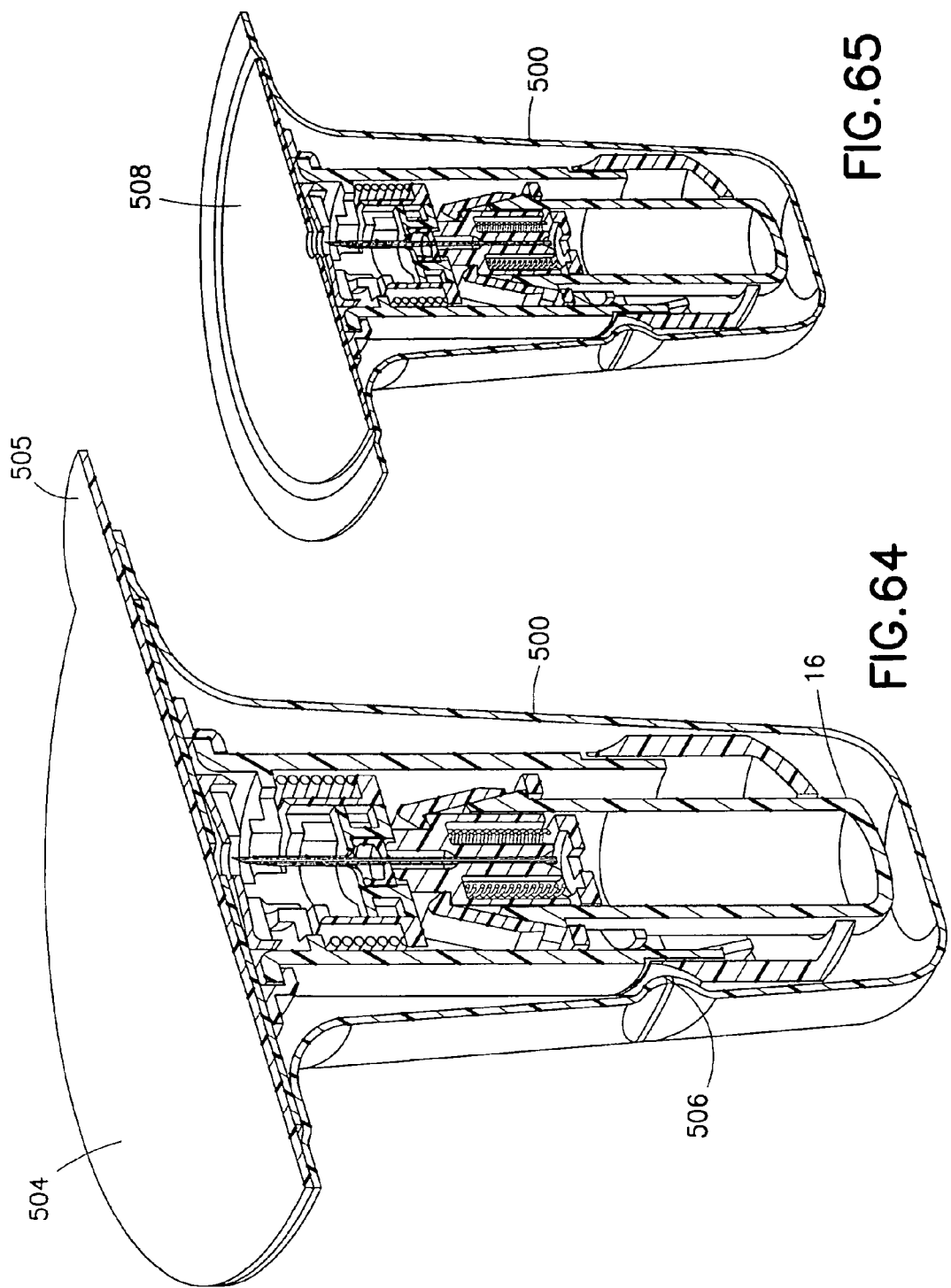

INFUSION DEVICE WITH AUTOMATIC INSERTION AND INTRODUCER NEEDLE RETRACTION

CROSS-REFERENCE TO RELATED APPLICATIONS

The application claims the benefit under 35 U.S.C. 119(e) of a U.S. provisional patent application of Ralph L. Sonderegger entitled "Infusion Device with One or More of Automatic Insertion, Automatic Retraction, Safety, Side-Push Button Activation, Rotary-Button Activation, Manual Interlock and Packaging", Ser. No. 61/448,975, filed Mar. 3, 2011, and a U.S. provisional patent application of Ralph L. Sonderegger et al. entitled "One-Piece Molded Catheter Assembly and Method of Manufacture", Ser. No. 61/441,258, filed Feb. 9, 2011, the entire contents of both of said applications being incorporated herein by reference.

FIELD OF THE INVENTION

The present invention relates generally to medical infusion systems, such as an insulin infusion device with one or more of automatic insertion and automatic retraction, needle safety, soft catheter and extension set. The system can further comprise a side-push button activation feature or a rotary-button activation feature, and one or more of a manual interlock of an outer barrel and base, and an extension set top and base, a manual interlock for an extension set top and base and packaging for an integrated and/or removable inserter for activation button protection.

BACKGROUND OF THE INVENTION

A large number of people, including those suffering from conditions such as diabetes, use some form of infusion therapy, such as daily insulin infusions, to maintain close control of their glucose levels. Currently, there are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer blood glucose control and an improved feeling of wellness.

The use of an infusion pump requires the use of a disposable component, typically referred to as an infusion set or pump set, which conveys the insulin from a reservoir within the pump into the skin of the user. An infusion set typically consists of a pump connector, a length of tubing, and a hub or base from which an infusion needle or a flexible cannula extends. The hub or base has an adhesive which retains the base on the skin surface during use, which may be applied to the skin manually or with the aid of a manual or automatic insertion device.

There are many available types of infusion sets, including steel needle infusion sets and soft catheter sets. Soft catheter sets are typically inserted into a patient manually with the aid of a steel needle introducer, which is removed from the patient after insertion to leave the soft catheter in place. In another type of infusion set, a mechanized insertion device is used to forcefully and rapidly insert the introducer needle and catheter, remove the introducer, or both. Often, the insertion device is a separate, stand-alone unit that the user is required to carry and provide. Stand-alone inserters typically require the user to manually load a set and compress a spring of the inserter, which can result in catheter insertion failure when either the set or the spring is not properly loaded or compressed.

In soft catheter sets, the introducer needle is completely removed from the infusion set before being connected to the insulin pump. One problem associated with manually inserting and retracting the introducer needle is variability in the insertion and retraction force, speed, smoothness and angle. This variability can lead to an increased rate of catheter insertion failure.

Further, as noted above, the user typically must remove the introducer needle after inserting the catheter. This exposes the user to accidental needle sticks from handling the removed introducer needle.

Accordingly, a need exists for infusion sets and insertion devices that facilitate insertion of the catheter, while reducing the number of components a user must carry and substantially preventing accidental needle sticks.

SUMMARY OF THE INVENTION

An object of the present invention is to substantially address the above and other concerns, and provide infusion sets and insertion devices that facilitate insertion of the catheter, while reducing the number of components a user must carry and substantially preventing accidental needle sticks.

Another object of the present invention is to provide an infusion device with one or more of automatic insertion and automatic retraction and a safety insulin catheter and extension set.

Another object of the present invention is to provide an infusion device with a side-push button activation feature.

Another object of the present invention is to provide an infusion device with a rotary-button activation feature.

Another object of the present invention is to provide an infusion device with a manual interlock of an outer barrel and base, and an extension set top and base.

Another object of the present invention is to provide an infusion device with a manual interlock for an extension set top and base.

Another object of the present invention is to provide an infusion device with packaging for an integrated and/or removable inserter for activation button protection.

These and other objects are substantially achieved by providing an infusion device that includes one or more of automatic insertion and automatic retraction, needle safety, soft catheter and extension set. The device can further comprise a top-push button activation feature, a side-push button activation feature or a rotary-button activation feature, and one or more of a manual interlock of an outer barrel and base, and a manual interlock for an extension set top and base.

BRIEF DESCRIPTION OF THE DRAWINGS

The various objects, advantages and novel features of the exemplary embodiments of the present invention will be more readily appreciated from the following detailed description when read in conjunction with the appended drawings, in which:

FIGS. 35A-35B, 36A-36C, and 37 illustrate views of the device of FIG. 34 during use;

FIGS. 46-51 illustrate views of a manually-activated interlock for use with the above or other embodiments of the present invention;

FIGS. 61-67 illustrate views of a package for use with the above or other embodiments of the present invention.

Throughout the drawings, like reference numerals will be understood to refer to like parts, components and structures.

DETAILED DESCRIPTION OF THE EXEMPLARY EMBODIMENTS

The exemplary embodiments of the present invention deliver insulin to the subcutaneous layers of the skin via a standard insulin pump or other similar device. By utilizing an infusion device with one or more of automatic insertion and automatic retraction, needle safety, soft catheter and extension set, with either top, side or rotary activation and one or more interlocks, proper insertion and maintenance of the inserted catheter in the subcutaneous space is ensured, while maintaining a degree of comfort to the user. In each embodiment of the present invention described below, standard infusion set elements such as connectors, infusion catheters, adhesives and hubs can be provided.

Figure 1:
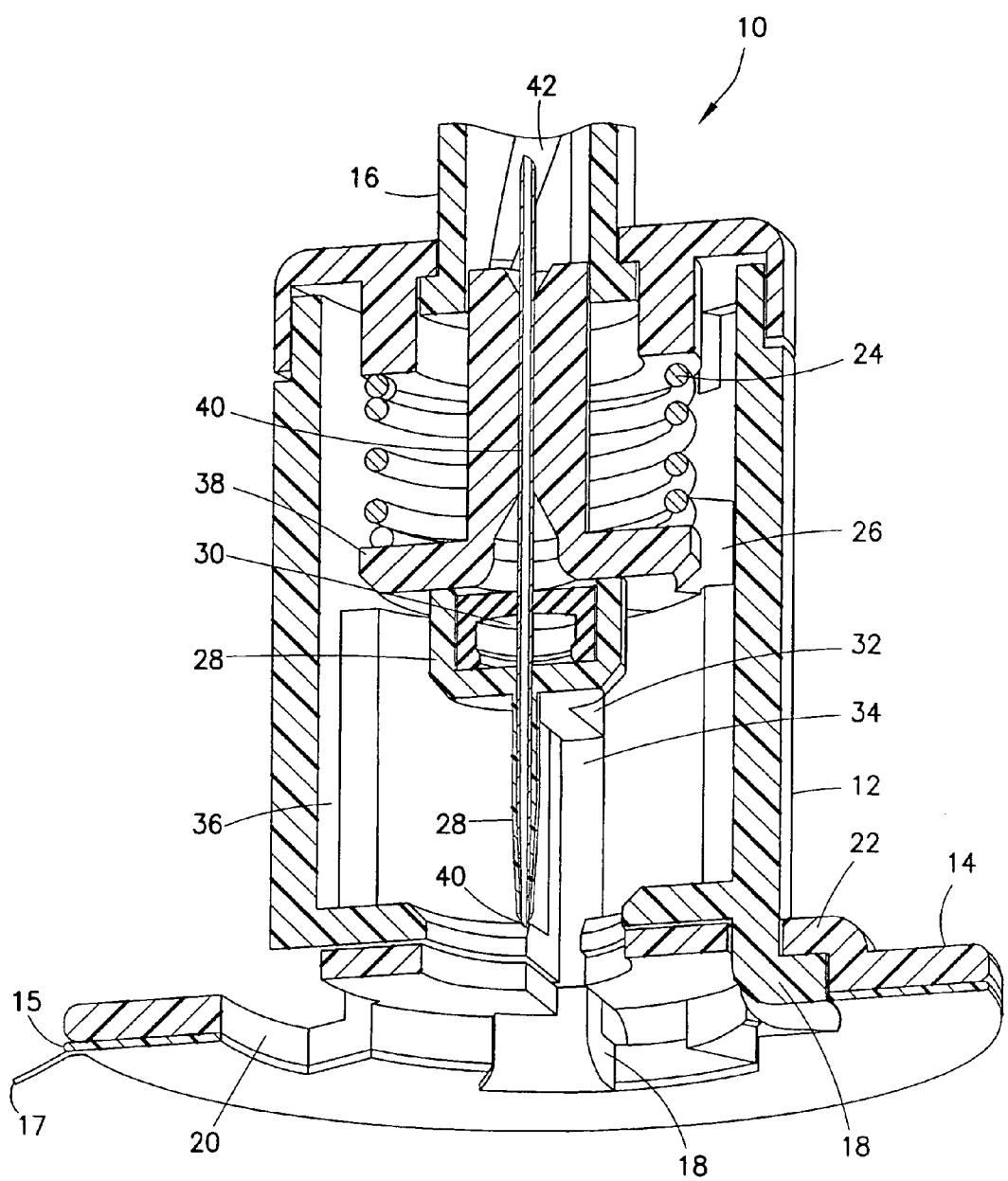
FIG. 1 is a sectional view of an infusion device utilizing a top-push button in accordance with a first embodiment of the present invention.

In a first exemplary embodiment of the present invention, the device comprises an infusion set and insertion device packaged as a single unit, thereby eliminating the need to carry any additional accessories and avoid the difficulty associated with loading the infusion set onto the insertion device at each use. FIG. 1 is a sectional view of a device 10 in accordance with an embodiment of the present invention. The device 10 comprises an outer barrel 12, a base 14 and a button 16. The base 14 comprises at least one outer barrel retention tab 18 that is configured to rotatably enter openings 20 in the base 14 and be captured at a rotational position by shoulders 22 of the base 14. A drive spring 24, needle hub sear 26 and catheter 28 are disposed within the outer barrel 12. The catheter 28 contains a septum 30, and has one or more catheter alignment and retention tabs 32 extending therefrom, to be captured and guided within one or more catheter alignment slots 34 within the outer barrel 12. One or more needle hub sear slots 36 are also provided within the outer barrel 12.

The embodiment of the present invention can be provided with a skin contacting adhesive layer 15 such as a pressure sensitive adhesive (PSA), and an adhesive cover 17. Precise insertion is achieved by removing the adhesive cover 17 and securing the infusion set to the infusion site via the adhesive layer 15, which permits the user to activate the inserter or place the catheter as described below at the proper alignment and depth. In doing so, the adhesive at or very near the insertion site secures the skin surface such that the introducer needle and catheter, or in-dwelling catheter are driven into the skin surface in a manner to minimize the risk of tenting at needle insertion.

Figure 2:
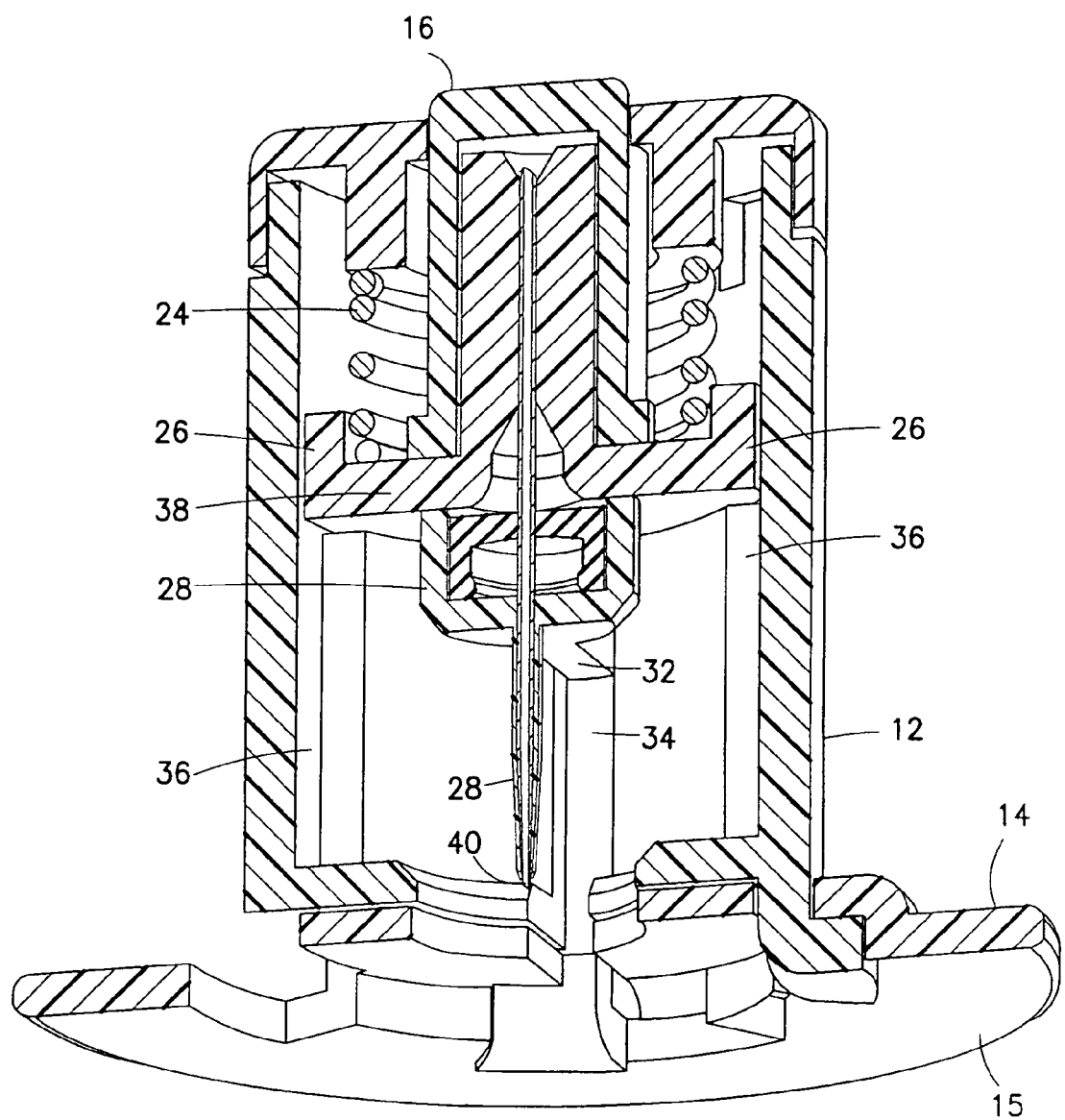
FIGS. 2-5 are views of the device of FIG. 1 during use.
Figure 3:
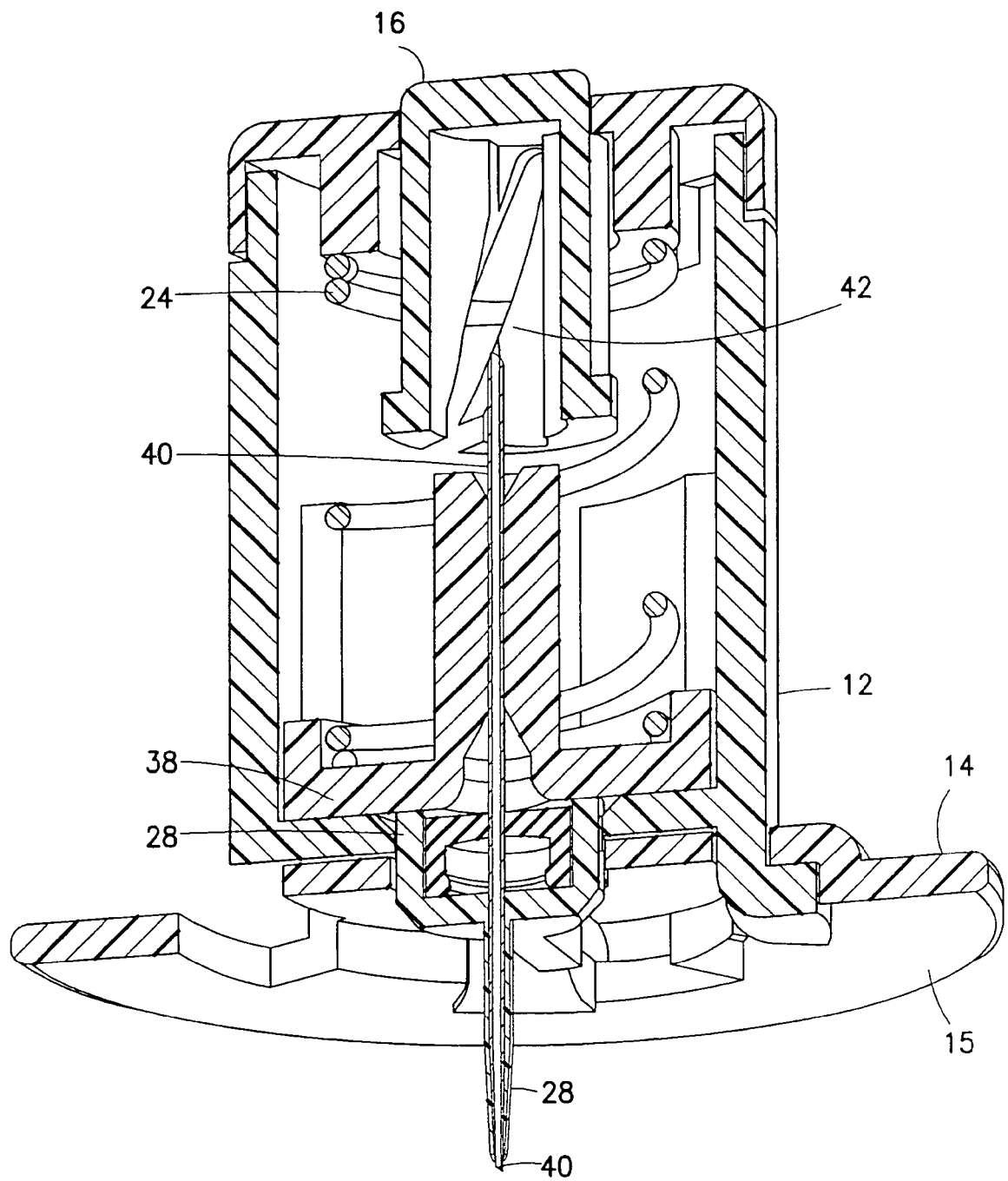

In the loaded position shown in FIG. 1, the outer barrel 14 is rotatably secured to the base 14 and the button 16 is extended from the top of the device, the drive spring 24 is compressed, and the catheter 28 is in a retracted position. The needle hub 38 and introducer needle 40 are also retracted. In the unloaded position shown in FIG. 2, the button 16 has been pressed and contacts the needle hub 38. As described in greater detail below, the downward travel of the button 16 serves to rotate the needle hub 38 such that the needle hub sear 26 becomes aligned with the needle hub sear slot 36. The device 10 is then permitted to activate as driven by the spring 24 such that the introducer needle 40 and catheter 28 are inserted into the skin surface (not shown). Specifically, one or more button cam slots 42 shown in FIG. 3, rotate the needle hub 38 by guiding the rotational lugs 44 (see FIG. 6) on the needle hub 38 as the button 16 is pressed down, so that the needle hub sears 26 become aligned with the needle hub sear slots 36 and the device 10 is permitted to activate.

Figure 4:
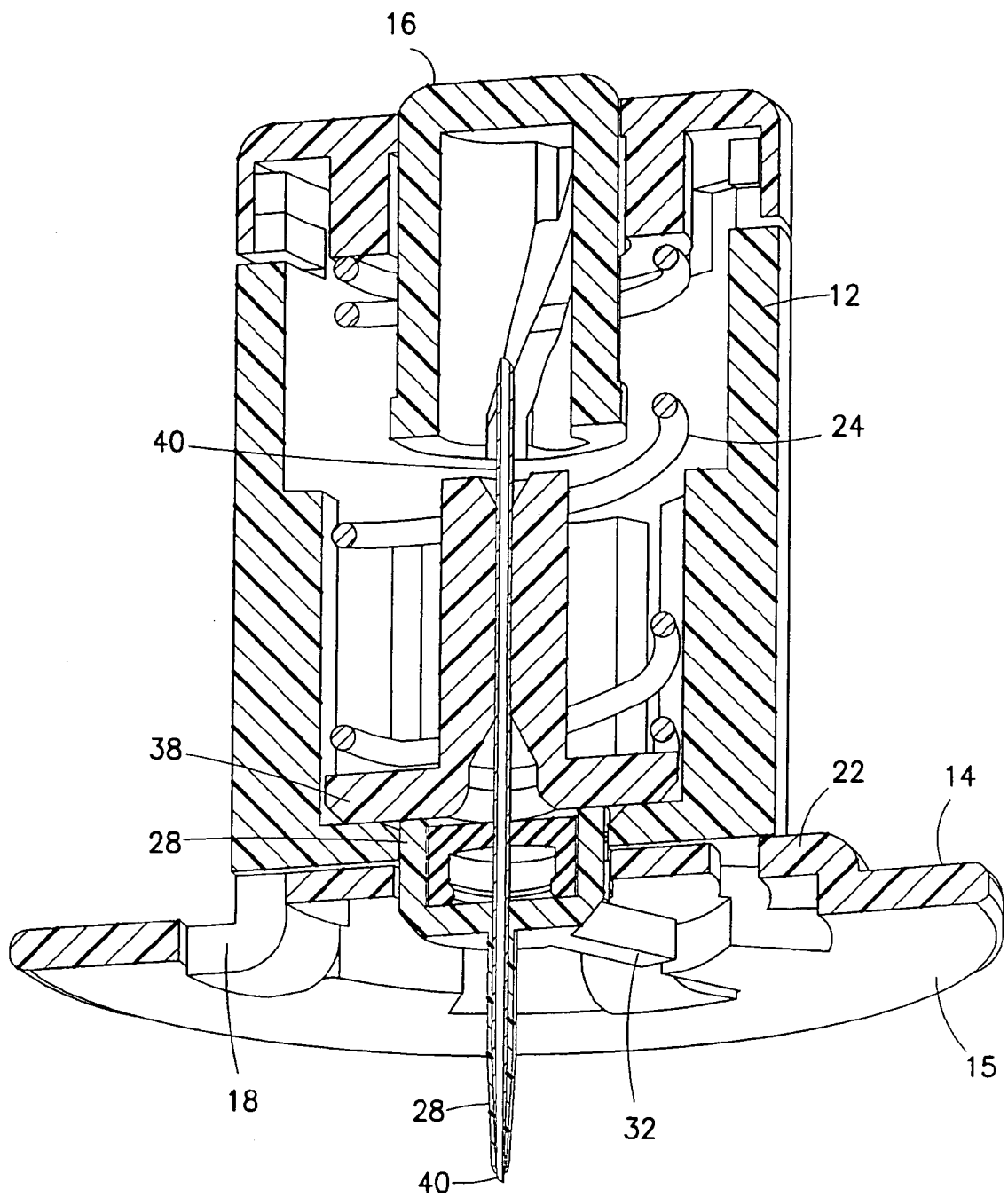
Figure 5:
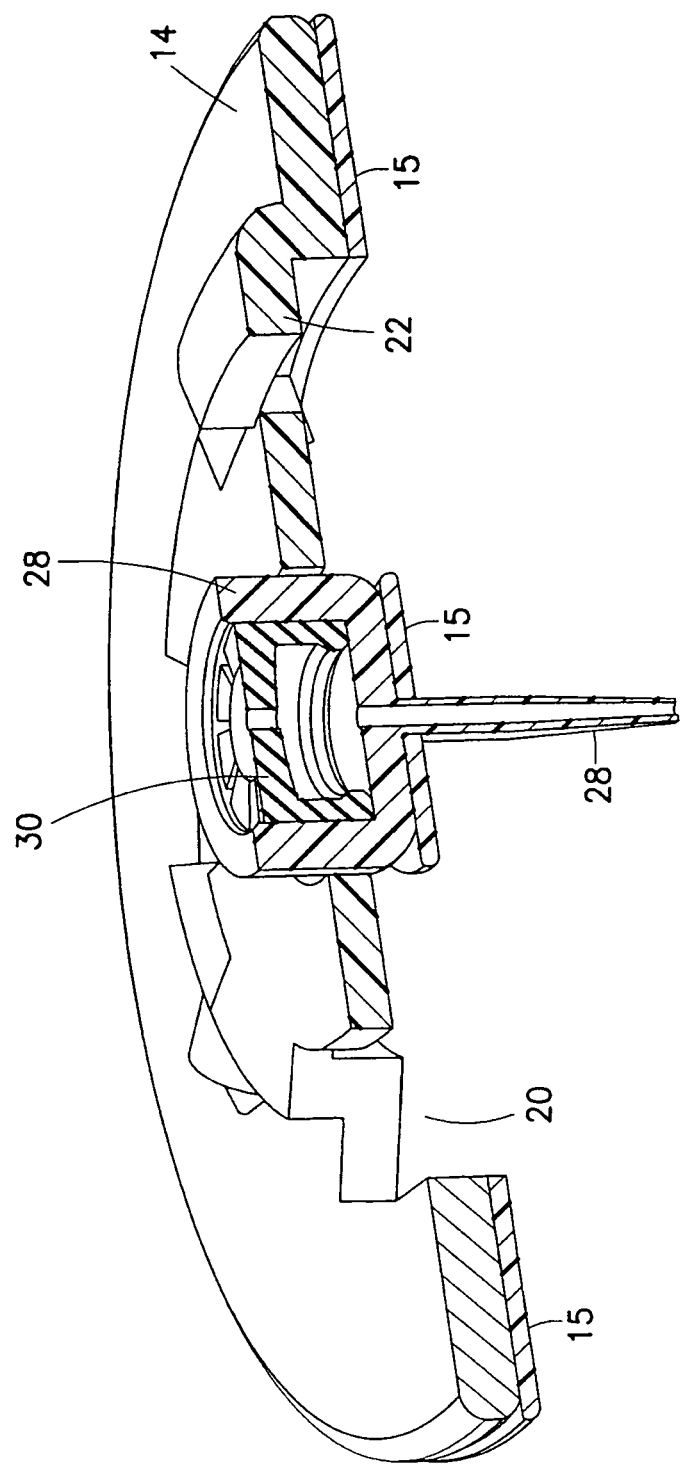

After activating the device 10 as described above, and the introducer needle 40 and catheter 28 are inserted into a skin surface, the user turns the outer barrel 12 of the device, which moves the catheter alignment/retention tab 32 into a locked position with the base 14. That is, the catheter alignment/retention tabs 32 enter the openings 20 to be captured by the shoulders 22 of the base 14 as shown in FIG. 4. The turning motion also serves to release the barrel retention tabs 18 of the outer barrel 12 from the same openings 20 and shoulders 22 of the base 14, leaving the base 14 as shown in FIG. 5 in condition for attachment of the tube set (not shown).

Figure 6:
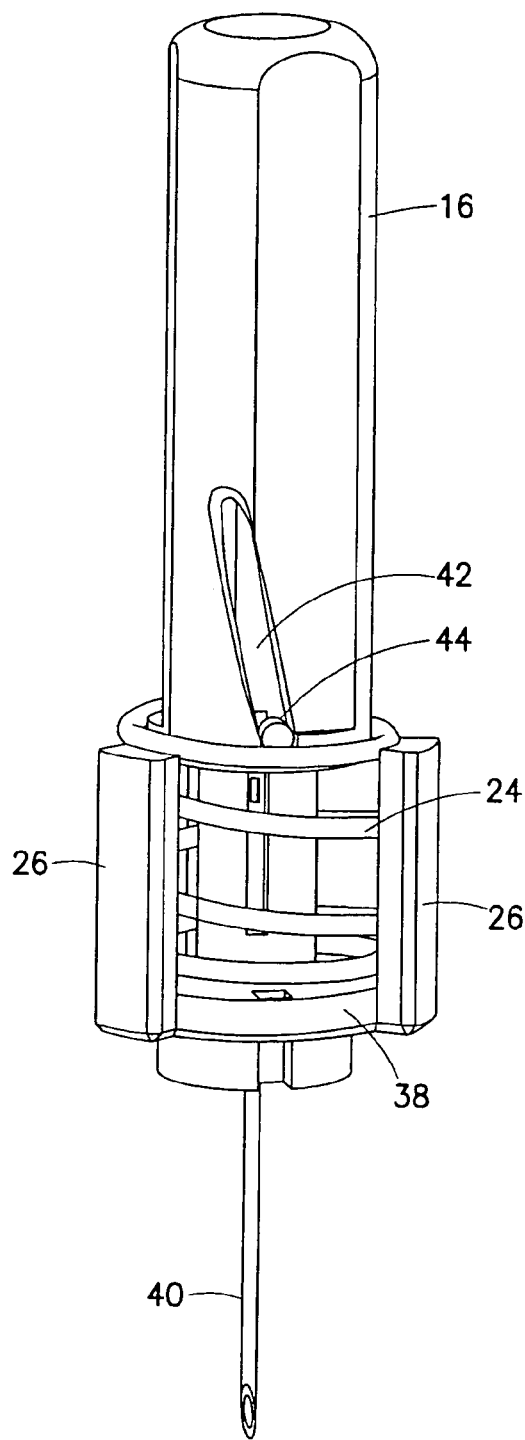
FIGS. 6 and 7 are views of the top-push button of the device of FIG. 1 incorporating a needle safety feature in accordance with an embodiment of the present invention.
Figure 7:
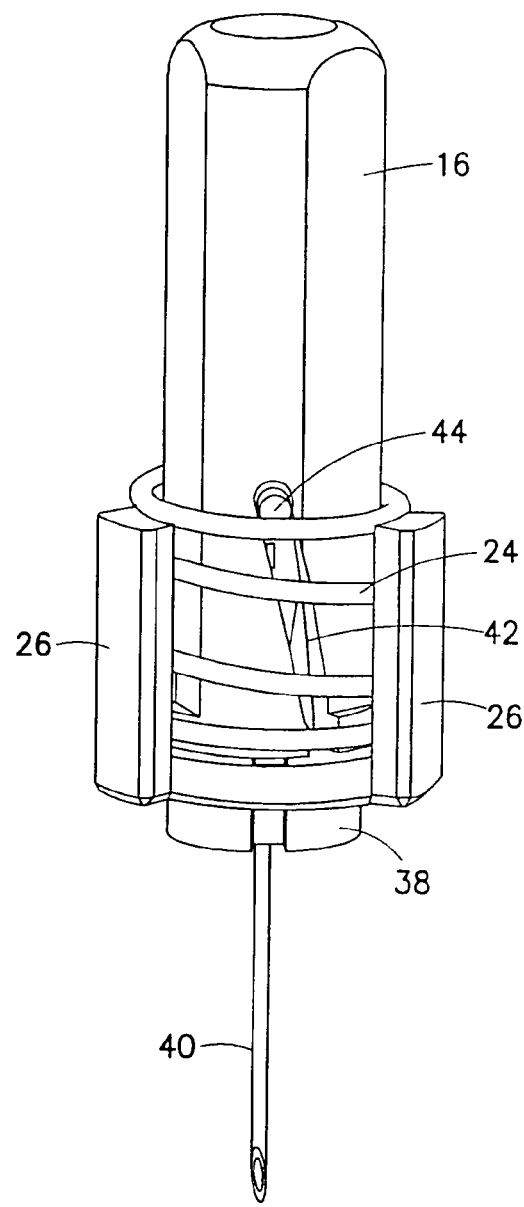

In yet another embodiment of the present invention, a needle safety can be configured to operate with the above device, utilizing the same actions and operations for deployment. For example, the button 16 is shown again in FIG. 6 to illustrate such a safety concept button cam in detail, in an inactivated position, and in FIG. 7 to illustrate an activated position. FIGS. 6 and 7 show the rotational lugs 44 of the needle hub 38 within the slots 42 of the button 16. To provide an automatic safety shown in greater detail in FIG. 8, the device 10 can further comprise an outer barrel cap 50, inner barrel cap 52, inner barrel 54 and safety spring 56.

Figure 8:
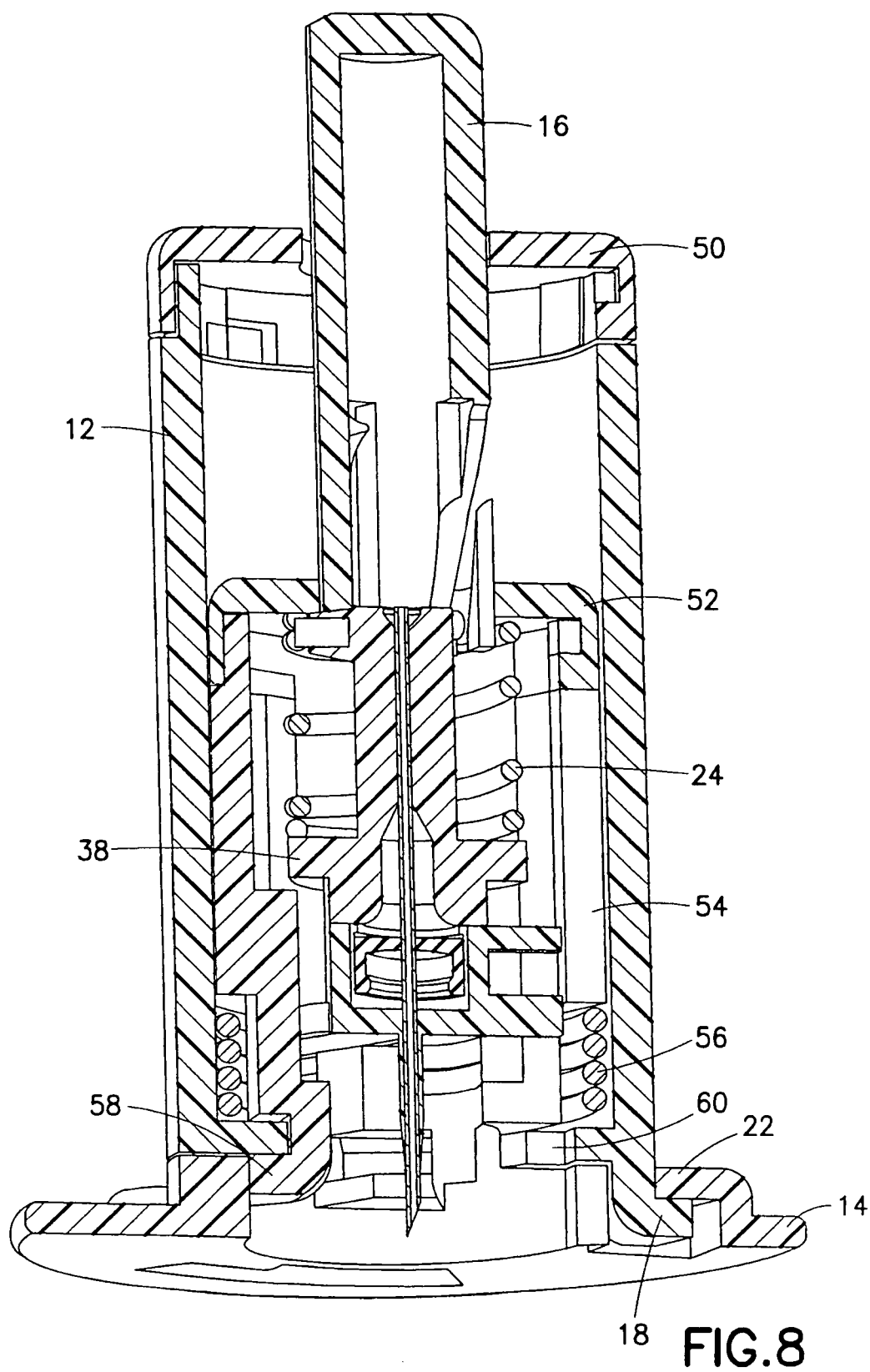
FIG. 8 is a sectional view of the device of FIG. 1 incorporating a needle safety feature in accordance with an embodiment of the present invention.
Figure 9:
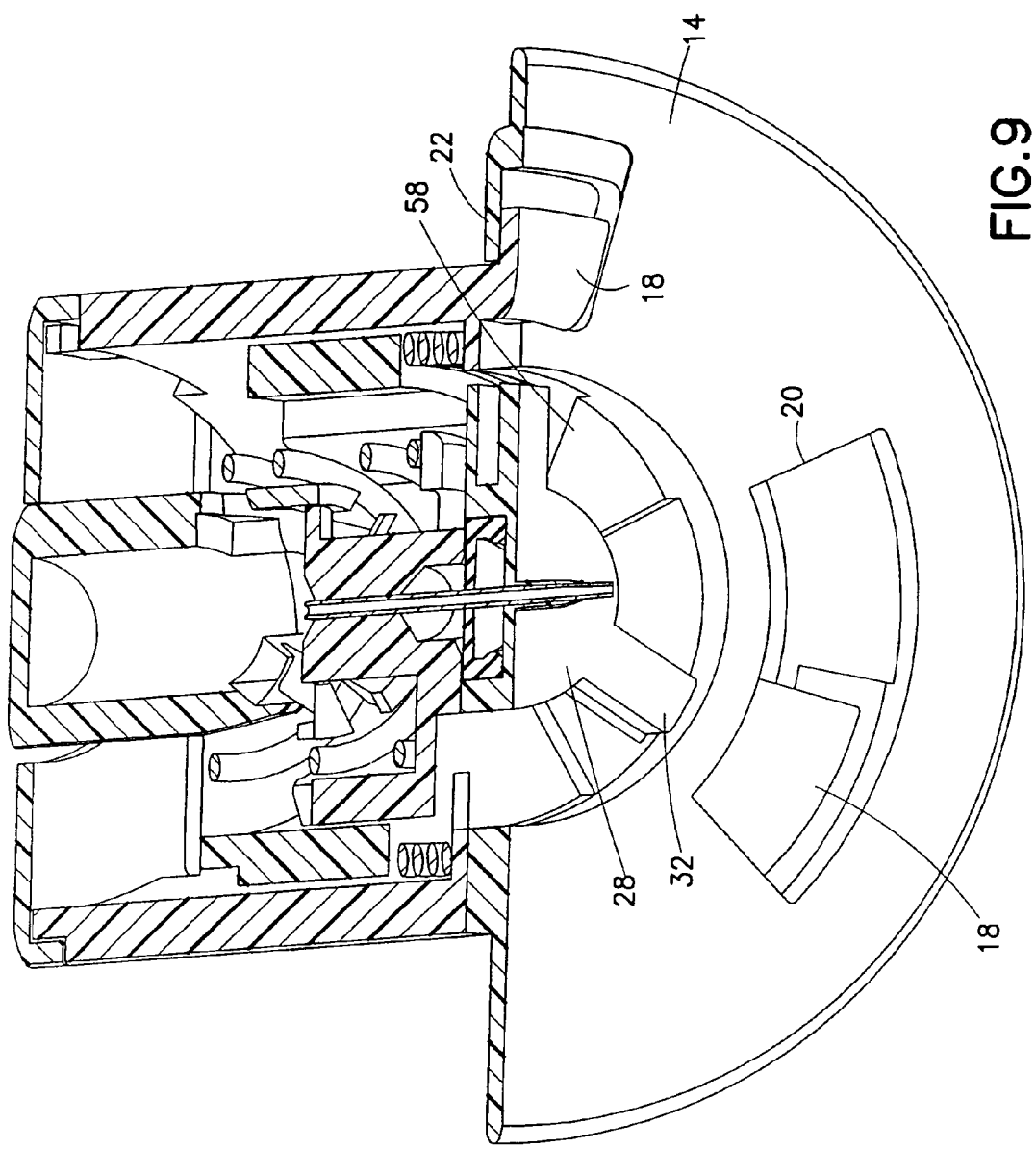
FIGS. 9-17 are views of the device of FIG. 8 during use.
Figure 10:
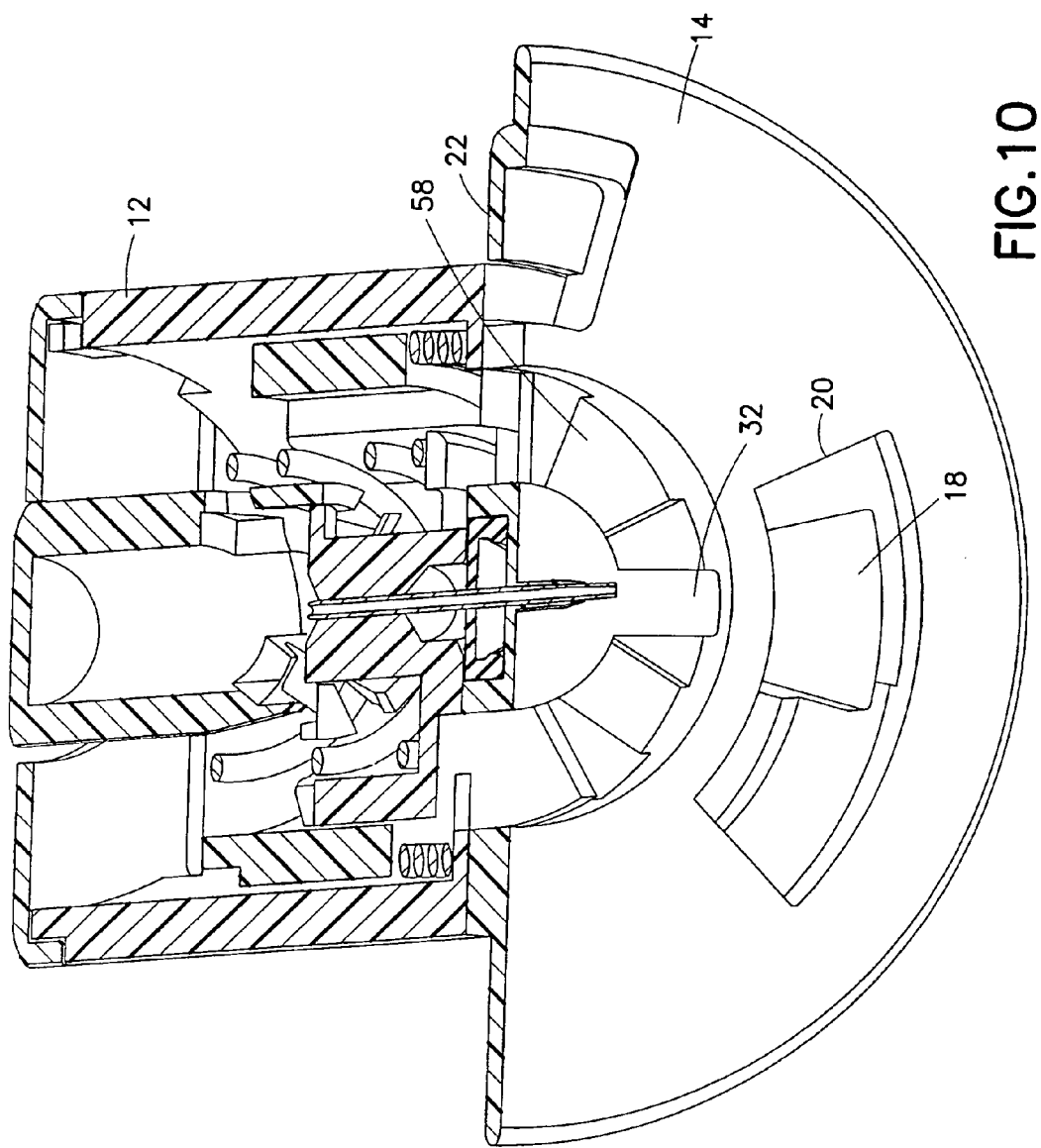
Figure 11:
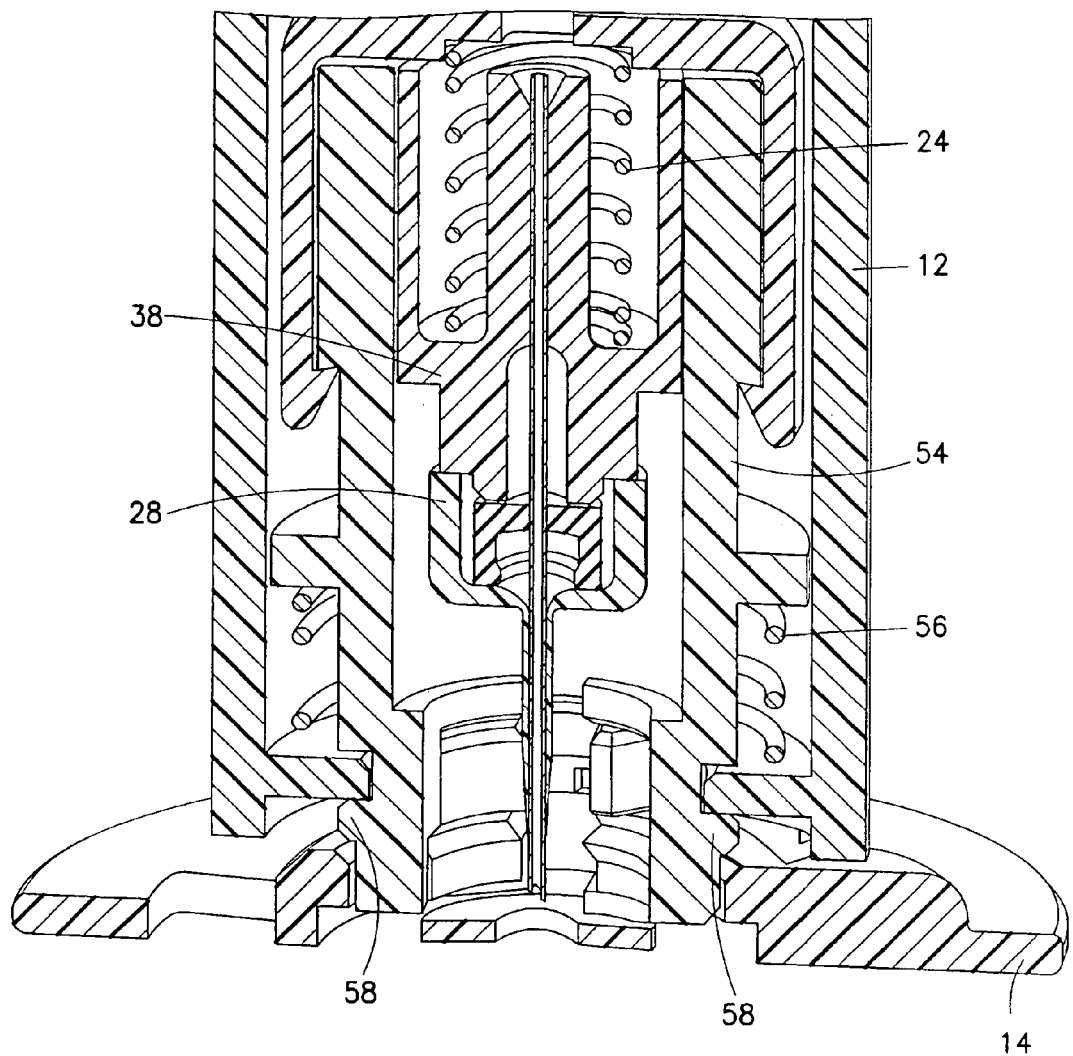
Figure 12:
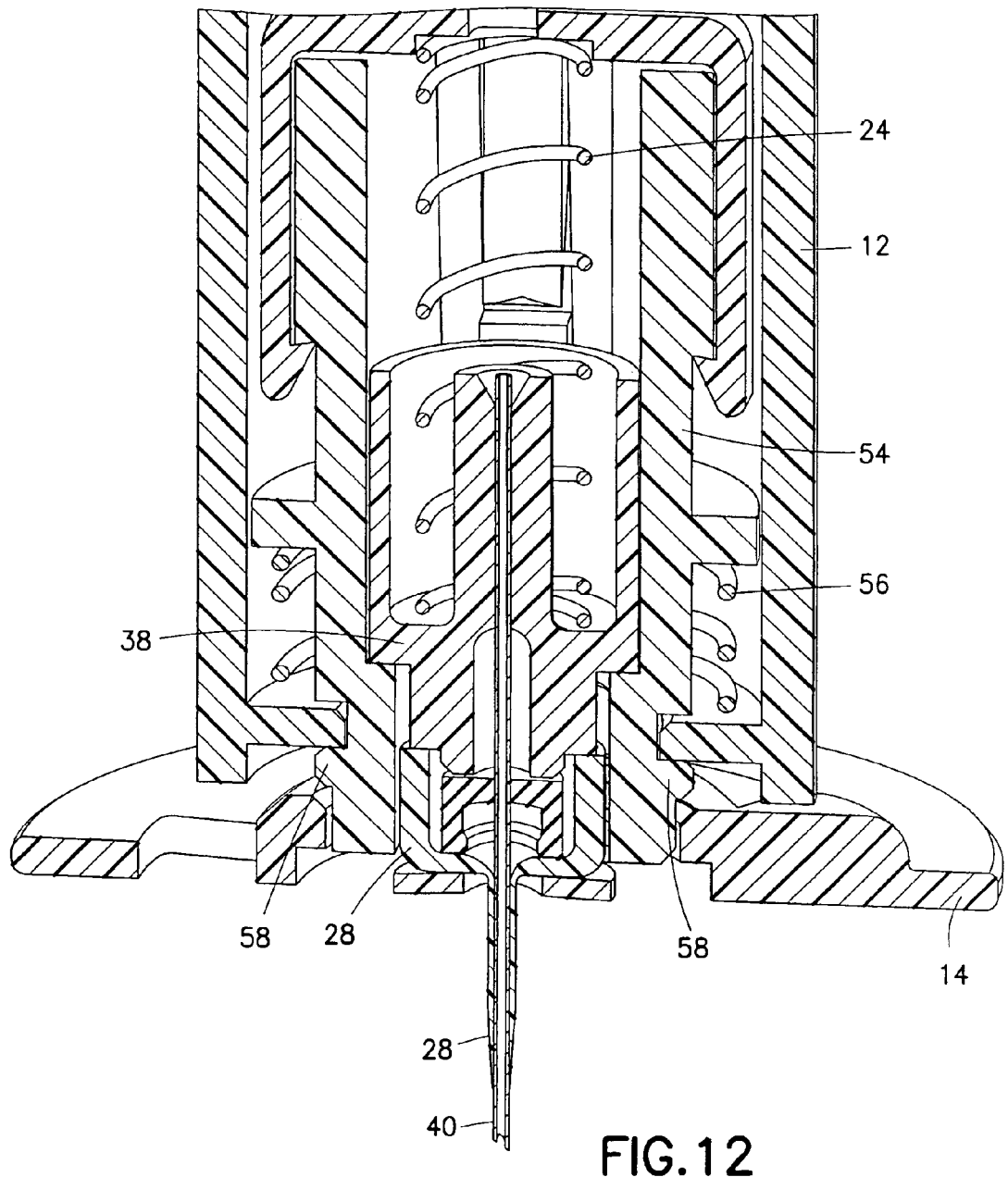
Figure 13:
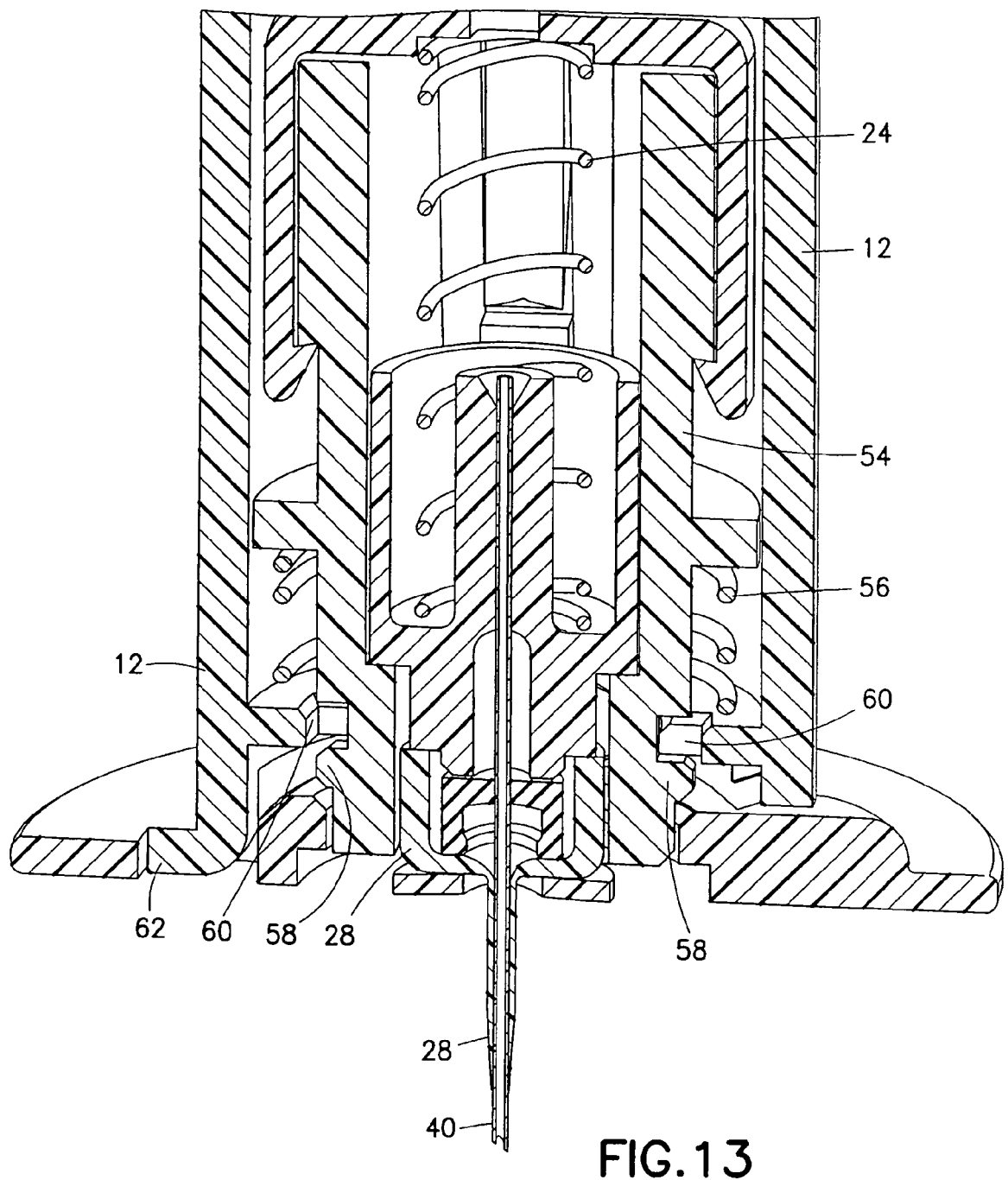
Figure 14:
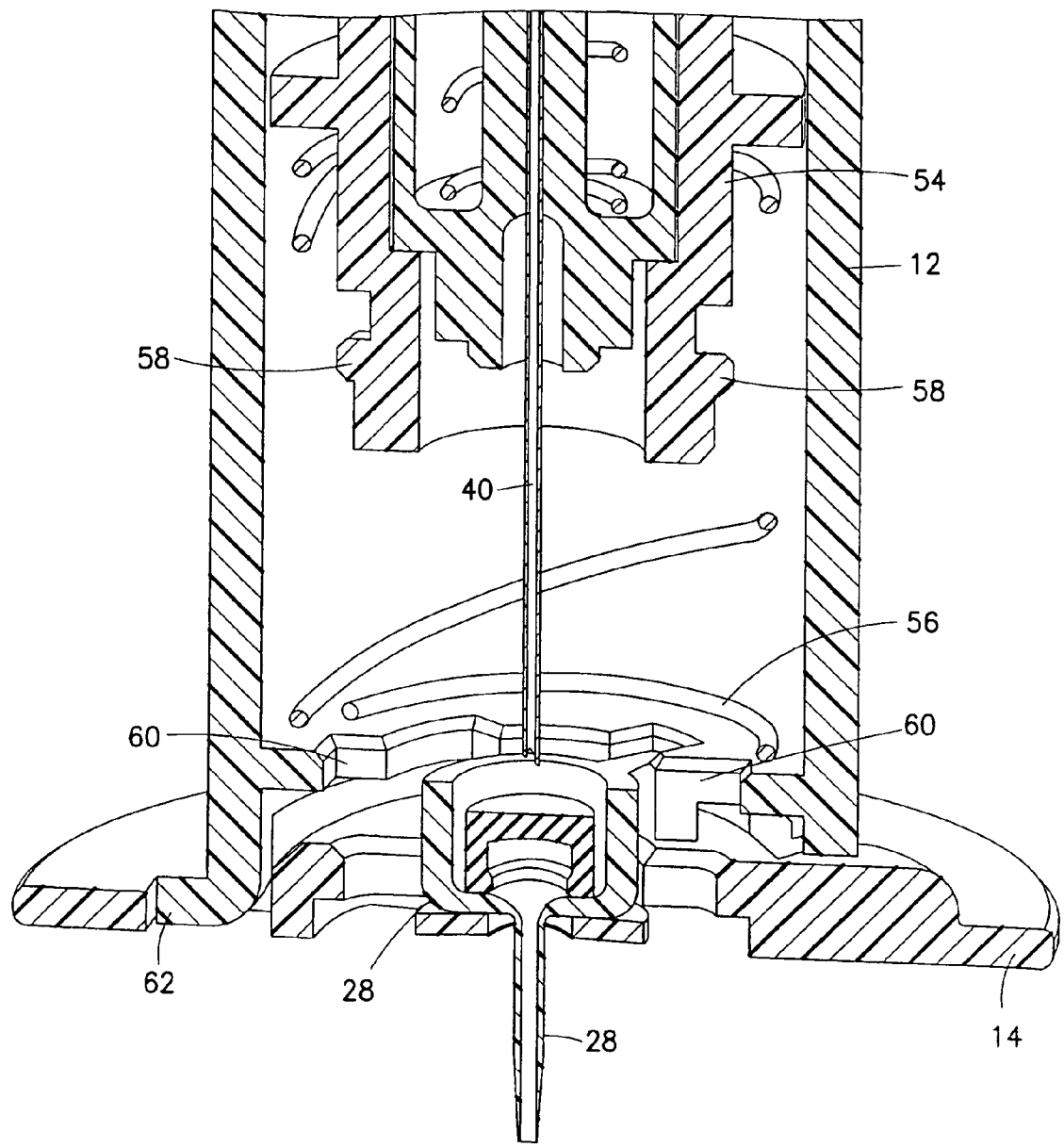

In this case, the rotation of the outer barrel 12 which serves to secure the catheter alignment/retention tabs 32 and release the barrel retention tabs 18 as described above, can also serve to move an inner barrel retention tab 58 from an initial state where the inner barrel retention tab 58 is locked to the outer barrel 12 as shown in FIG. 8, to a position to release the safety. As the outer barrel 12 is turned, the inner barrel retention tab 58 is restrained so as not to rotate, and aligns with the release slot 60 in the outer barrel 12. The catheter alignment/retention tab 32 is engaged with the base 14 as described above. The outer barrel retention tab 18 is then disengaged from the base 14. In FIG. 11, the inner barrel retention tabs 58 are shown engaged with the outer barrel 12, and FIG. 12 illustrates the inner barrel retention tabs 58 engaged with the outer barrel 12 in an activated position. The inner barrel retention tabs 58 disengage the instant before the needle safety activates, and once rotated to align with the trigger slot 60 in the outer barrel 12 as shown in FIG. 13, allows the needle safety to activate into the retracted position shown in FIG. 14.

Figure 15:
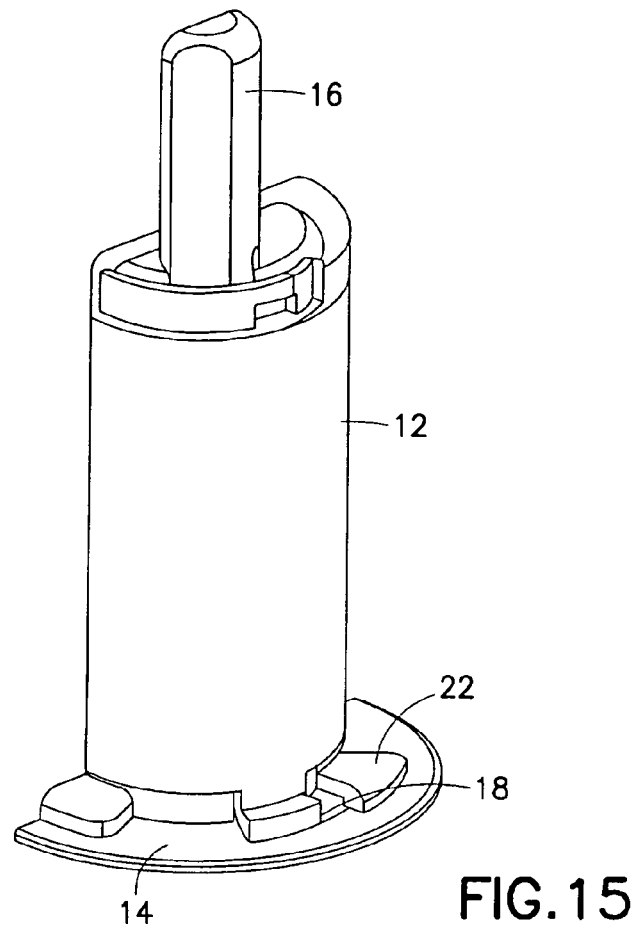
Figure 16:
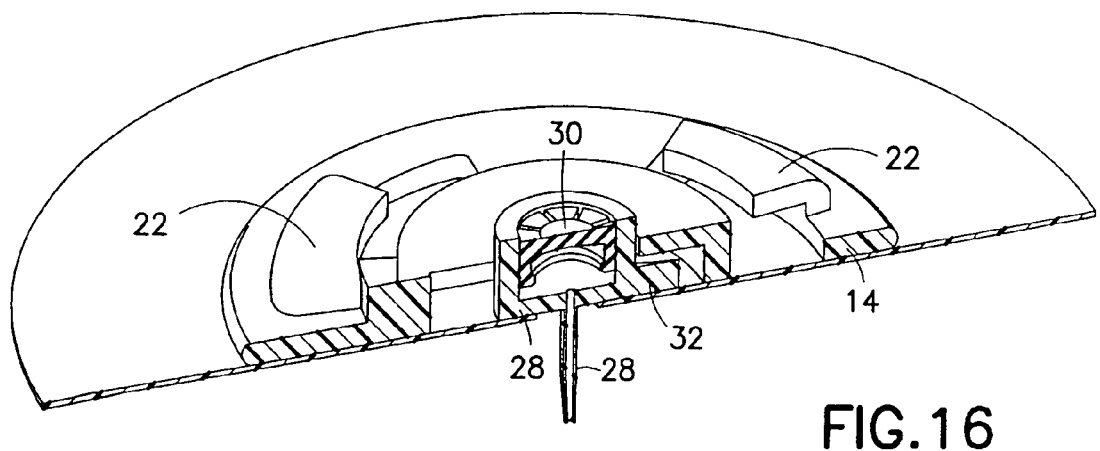
Figure 17:
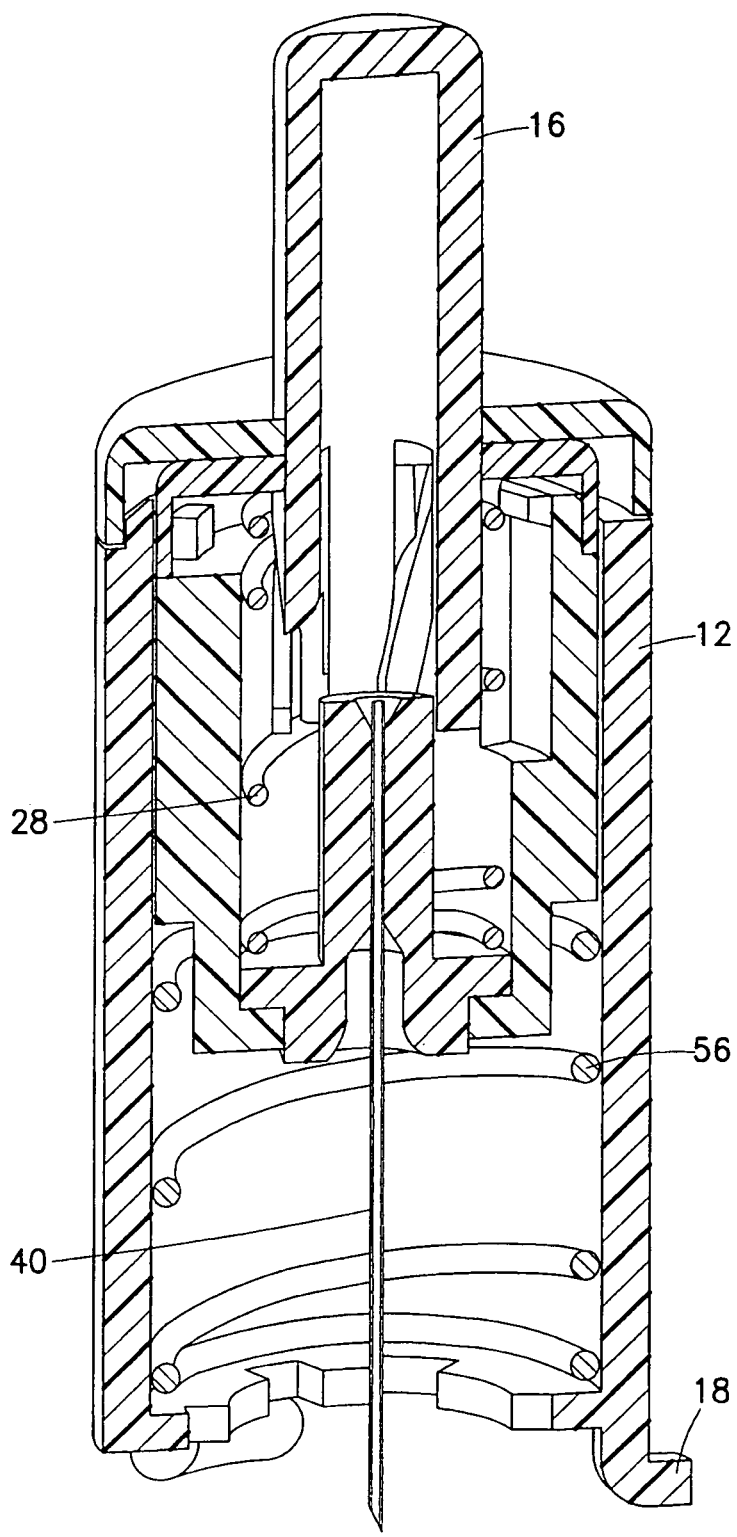

Further turning results in the disengagement of the outer barrel retention tabs 18 from the base 14 as shown in FIG. 15, and moves the catheter alignment/retention tab 32 into a locked position with the base 14, leaving the base 14 in condition for attachment of the tube set as shown in FIG. 16. The disposable launcher or inserter assembly can then be removed and discarded as shown in FIG. 17.

Figure 18:
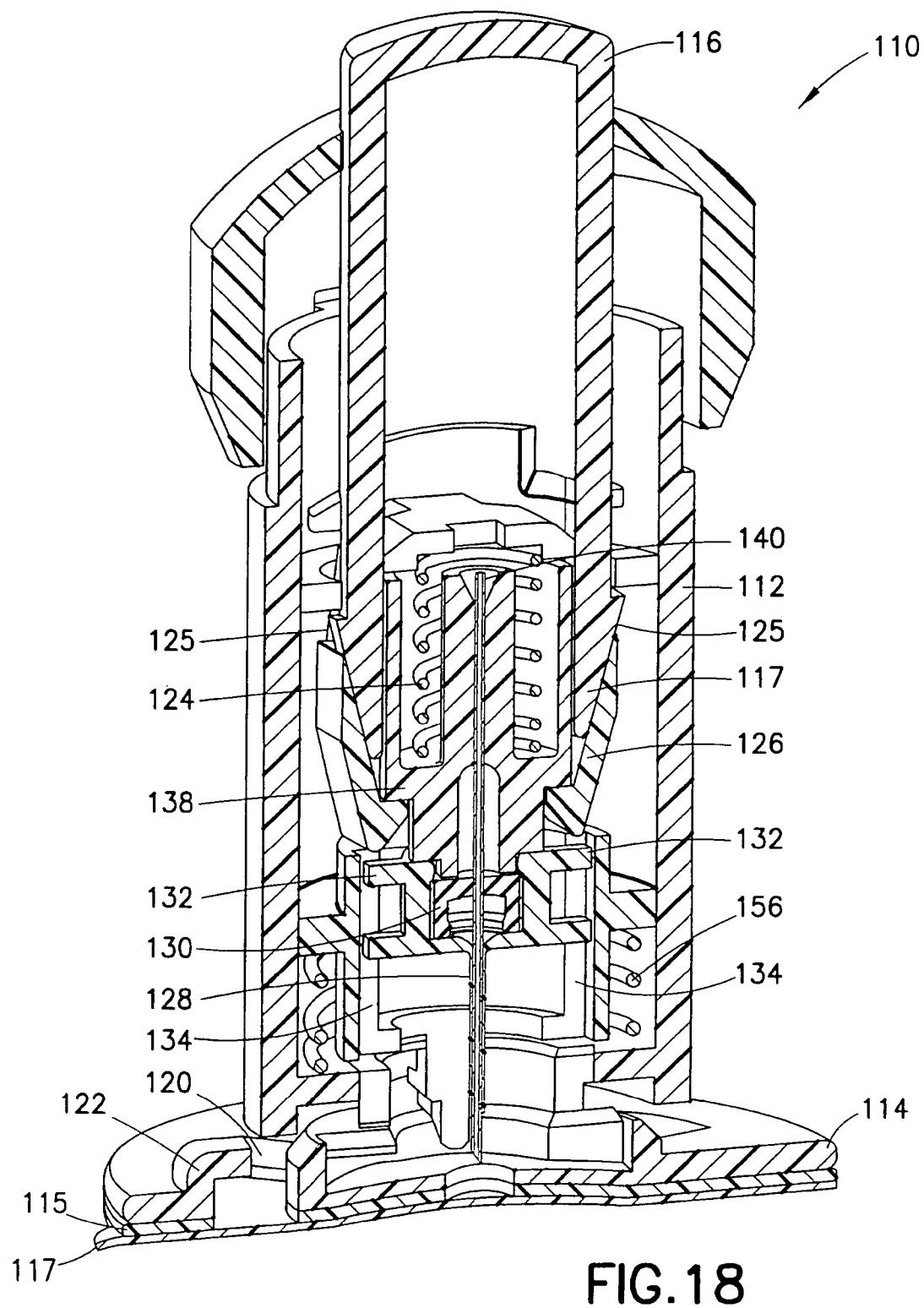
FIG. 18 is a sectional view of an infusion device utilizing a top-push button in accordance with a second embodiment of the present invention.
Figure 19:
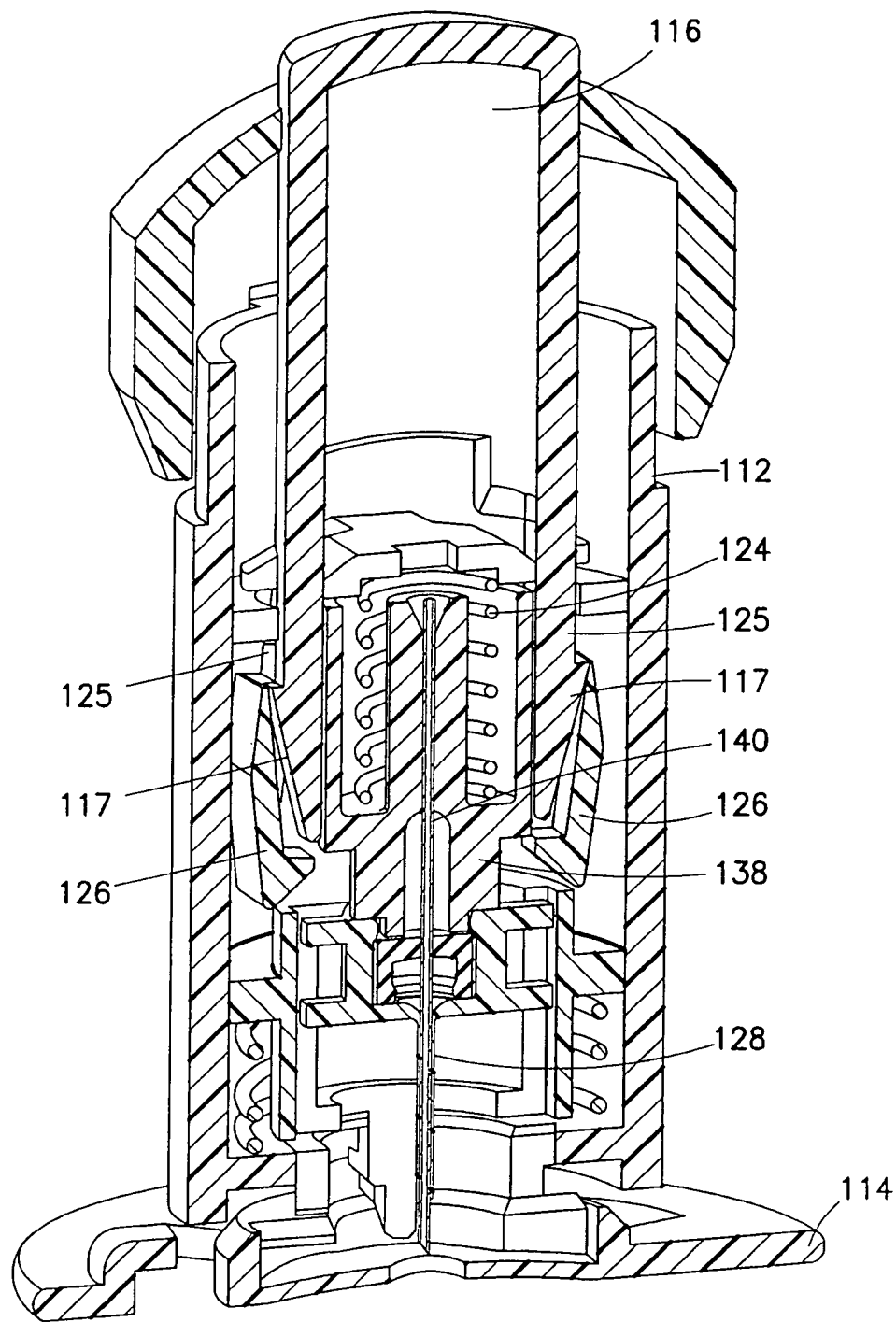
FIGS. 19-26 illustrate views of the device of FIG. 18 during use.
Figure 21:
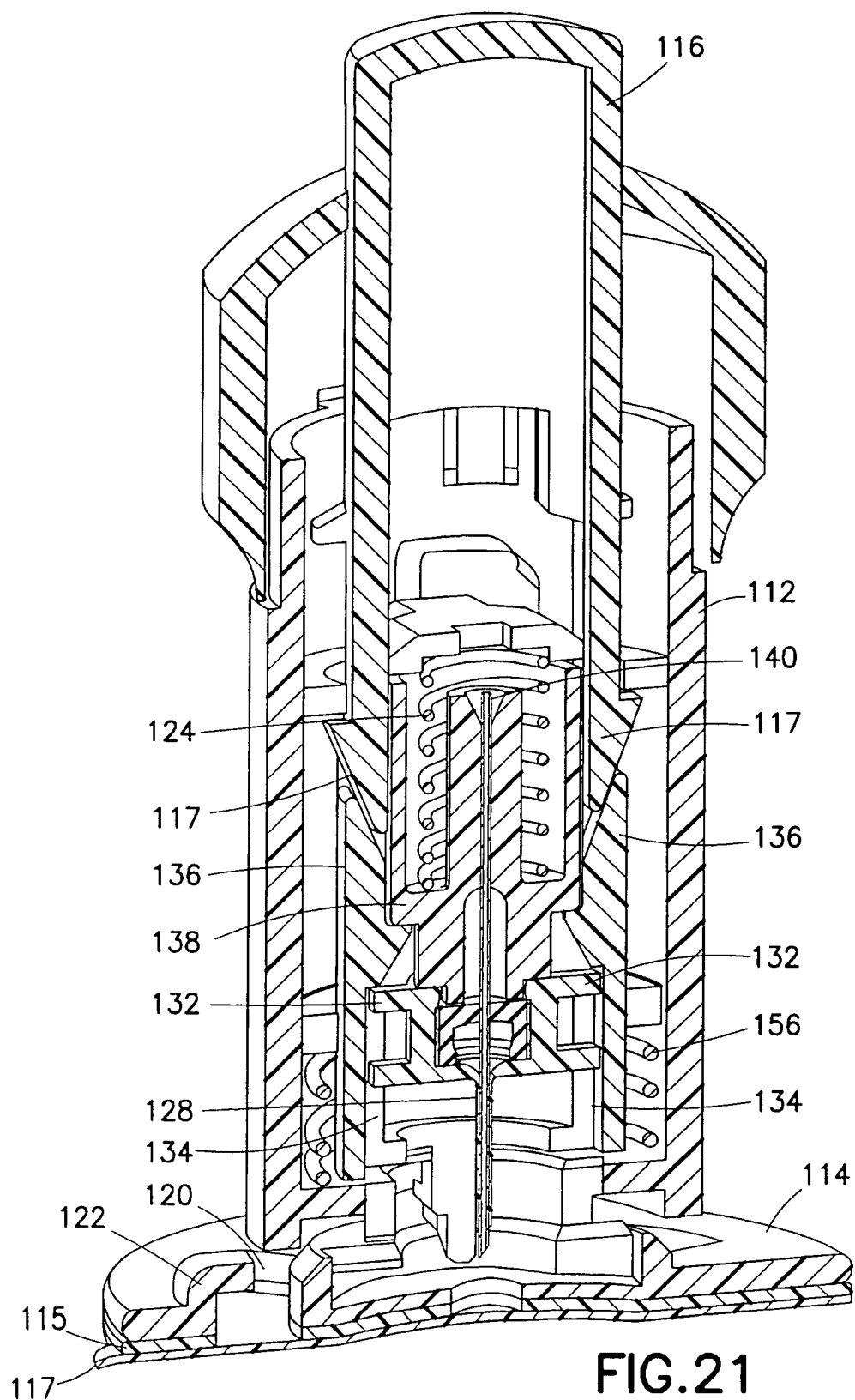
Figure 22:
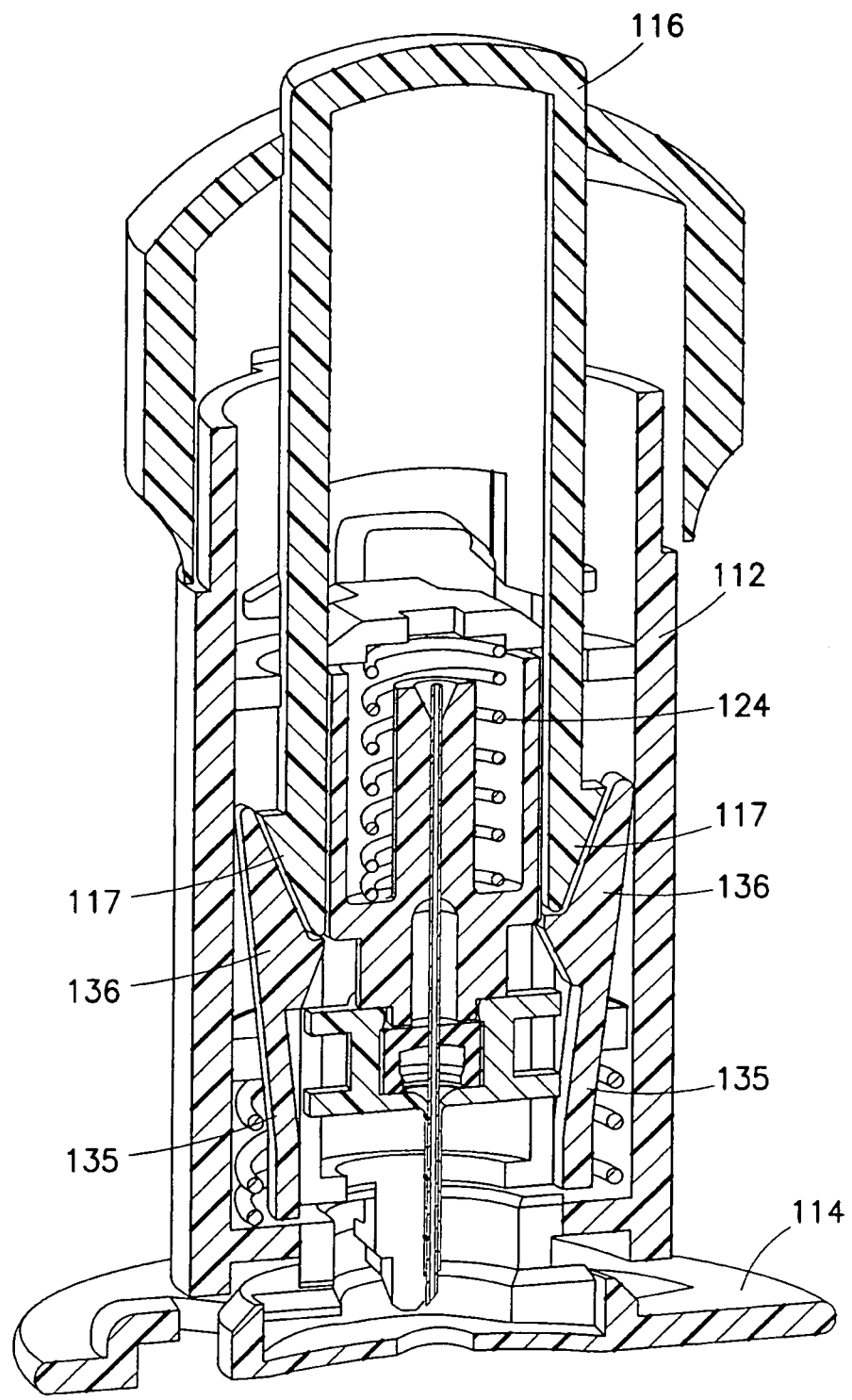
Figure 23:
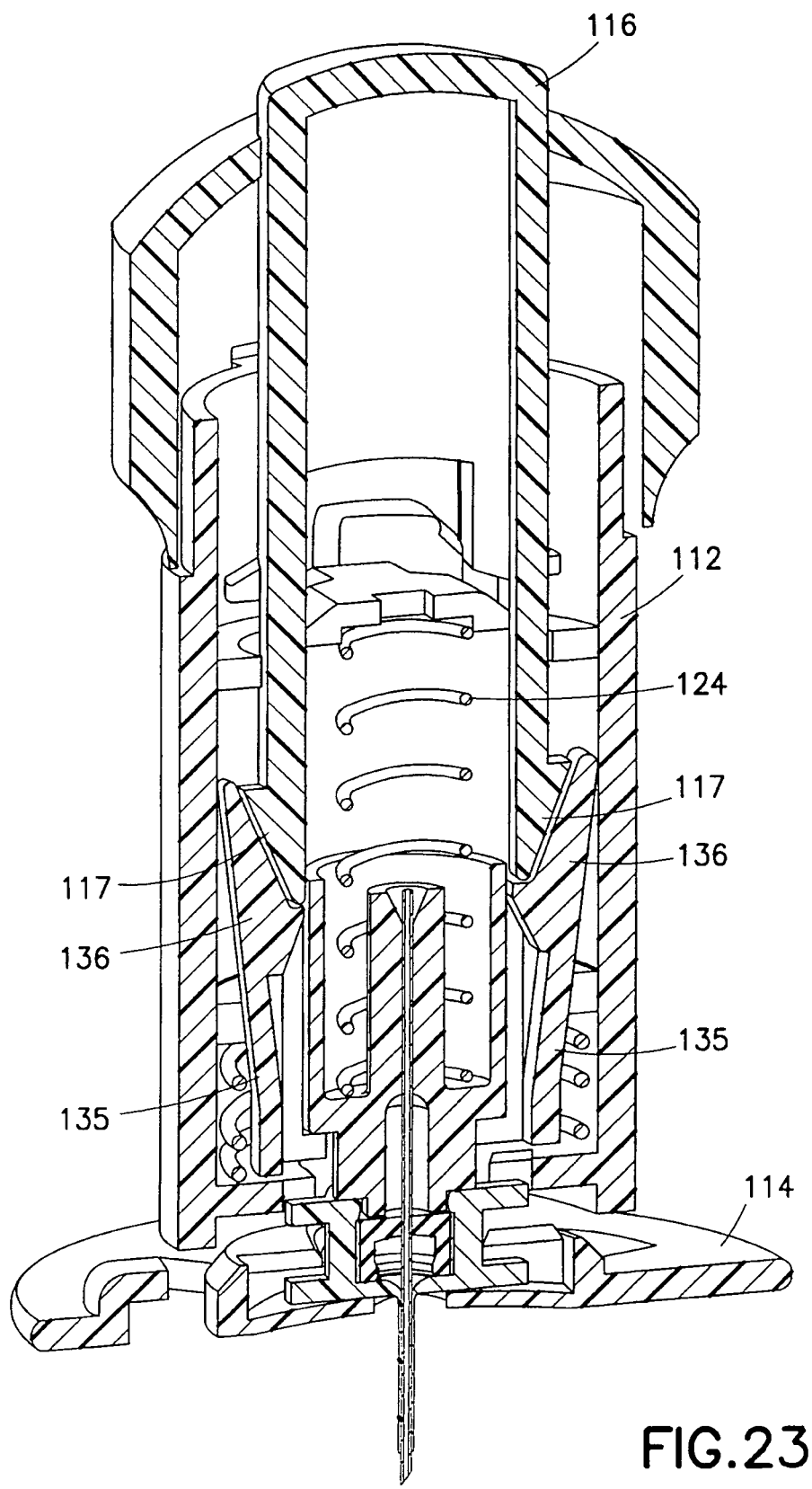

In a second exemplary embodiment of the present invention, the device again comprises an infusion set and insertion device packaged as a single unit, thereby eliminating the need to carry any additional accessories and avoid the difficulty associated with loading the infusion set onto the insertion device at each use. FIG. 18 is a sectional view of a device 110 utilizing an inserter and set in accordance with the second embodiment of the present invention. The device 110 comprises an outer barrel 112, a base 114 and a button 116. The base 114 comprises at least one outer barrel retention tab 118 that is configured to rotatably enter openings 120 in the base 114 and be captured at a rotational position by shoulders 122 of the base 114 as described above. A drive spring 124, flexible sear 126 and catheter 128 are disposed within the outer barrel 112. The flexible sear of the second embodiment can be provided in a number of positions. For example, in the embodiment shown in FIGS. 18-20, the flexible sear 126 is secured to the outer barrel 112 at a point 125. In the embodiment shown in FIGS. 21-23, the flexible sear 136 is secured to the outer barrel 112 at a point 135.

Disposed within the device 110, the catheter 128 contains a septum 130, and has one or more catheter alignment and retention tabs 132 extending therefrom, to be captured and guided within one or more catheter alignment slots 134 within the outer barrel 112. The push button 116 further comprises one or more deflectable, inclined button cams 117 to engage, deflect and release the flexible sears 126 from a needle hub 138. The needle hub 138 is provided with an introducer needle 140.

The embodiment of the present invention can be provided with a skin contacting adhesive layer 115 such as a pressure sensitive adhesive (PSA), and an adhesive cover 117. Precise insertion is achieved by removing the adhesive cover 117 and securing the infusion set to the infusion site via the adhesive layer 115, which permits the user to activate the inserter or place the catheter as described below at the proper alignment and depth. In doing so, the adhesive at or very near the insertion site secures the skin surface such that the introducer needle and catheter, or in-dwelling catheter are driven into the skin surface in a manner to minimize the risk of tenting at needle insertion.

Figure 20:
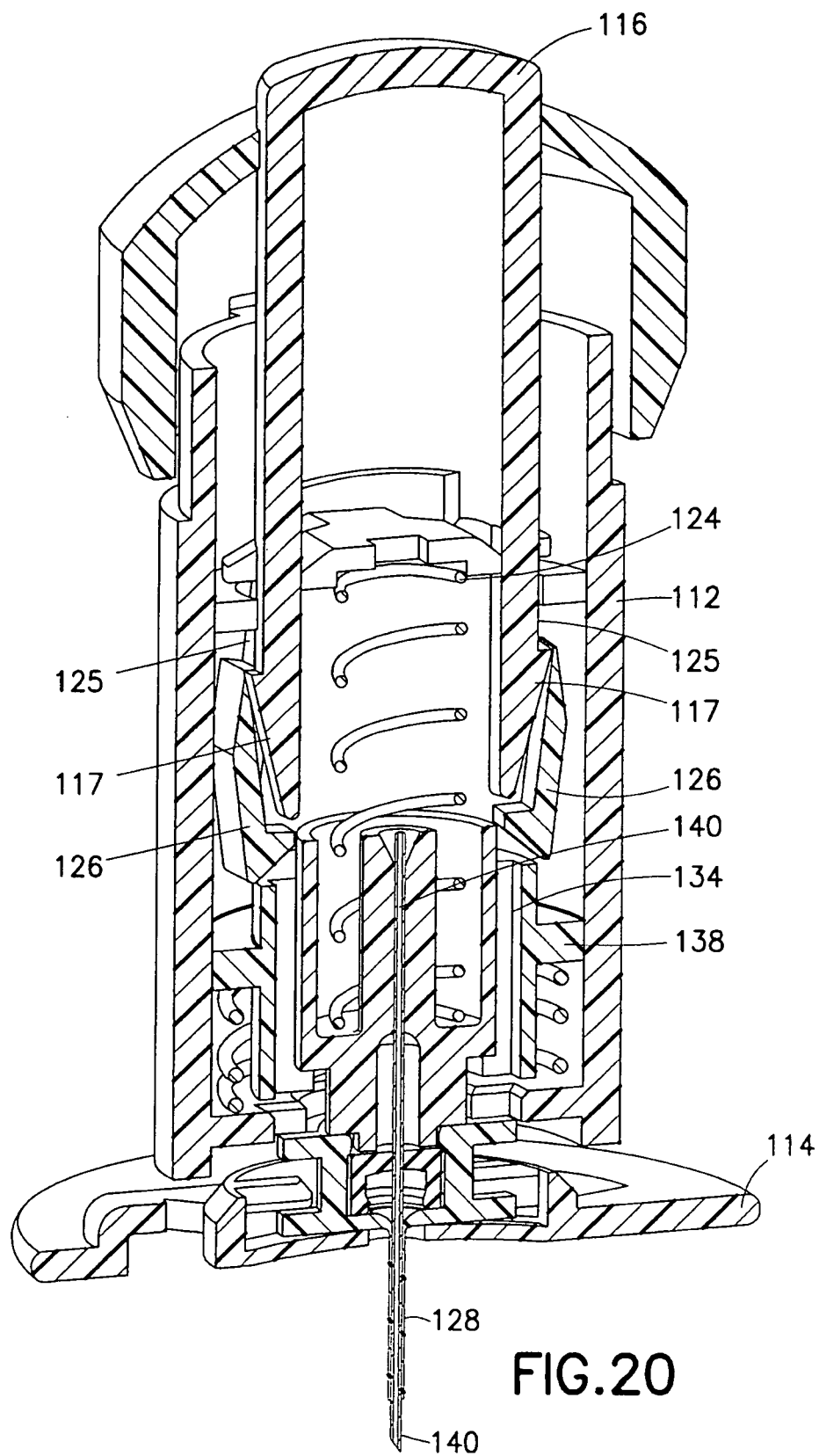

In the loaded position shown in FIG. 18, the outer barrel 114 is rotatably secured to the base 114 and the button 116 is extended from the top of the device, the drive spring 124 is compressed, and the catheter 128 is in a retracted position. The needle hub 138 and introducer needle 140 are also retracted. In the unloaded position shown in FIG. 19, the button 116 has been pressed and the deflectable, inclined button cams 117 engage, deflect and release the flexible sear 126 from the needle hub 138. At this point, the device 110 is permitted to activate as driven by the spring 124 such that the introducer needle 140 and catheter 128 are inserted into the skin surface as shown in FIG. 20.

Figure 24:
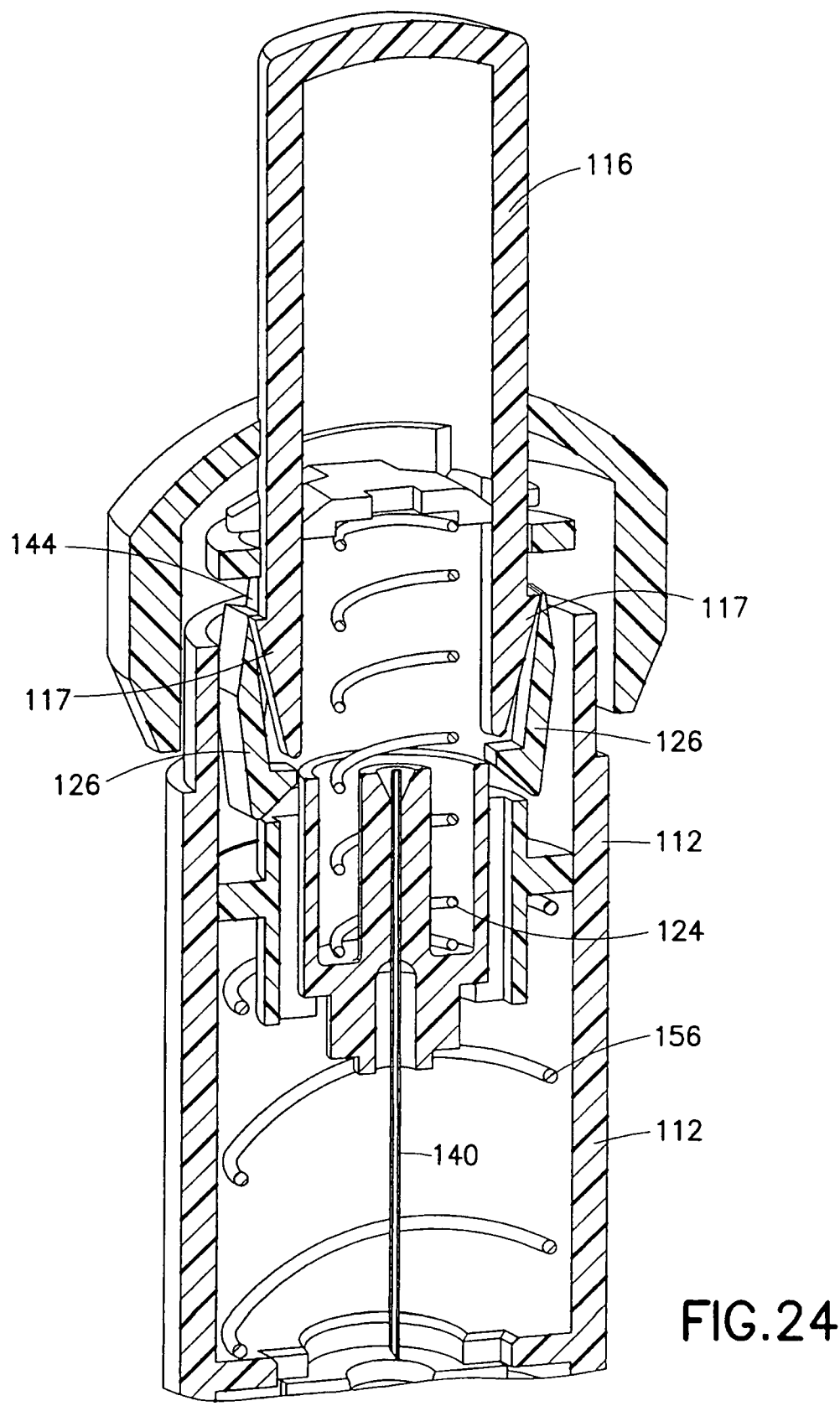

After activating the device 110 as described above, the user turns the outer barrel 112 of the device which moves the catheter alignment/retention tab 132 into a locked position with the base 114. That is, the catheter alignment/retention tabs 132 enter the openings 120 to be captured by the shoulders 122 of the base 114. The turning motion also serves to release the barrel retention tabs 118 of the outer barrel 112 from the same openings 120 and shoulders 122 of the base 114, leaving the base 114 in condition for attachment of the extension (tube) set. Further turning of the outer barrel 112 can activate a safety as described above. FIG. 24 shows the safety 144 in greater detail.

Figure 25:
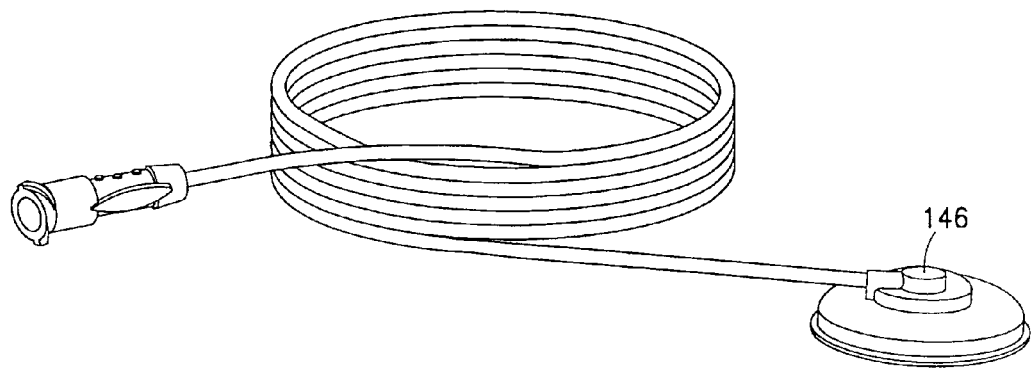
Figure 26:
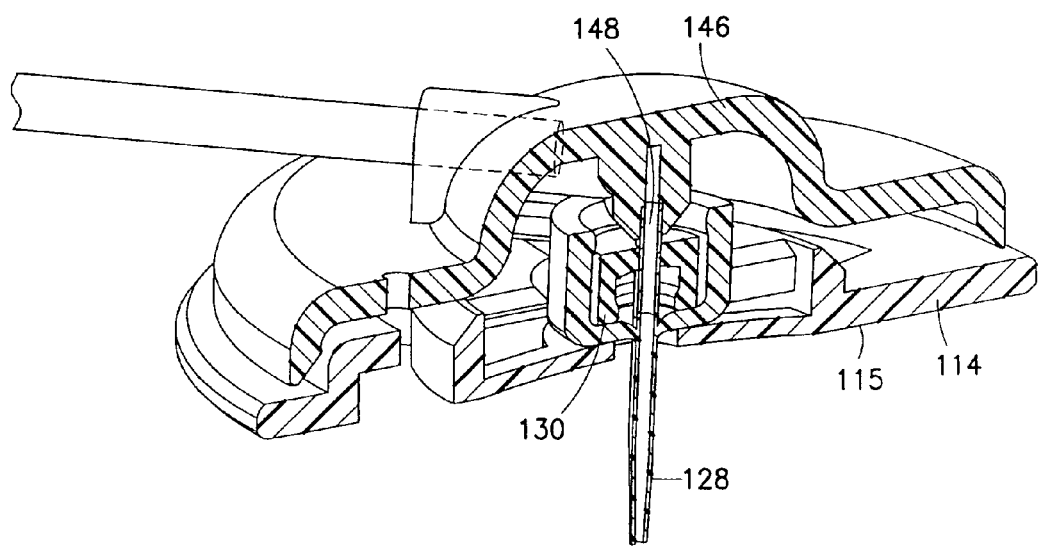

Turning of the outer barrel 112 results in the disengagement of the outer barrel retention tabs 118 from the base 114, and moves the catheter alignment/retention tab 132 into a locked position with the base 114, leaving the base 114 in condition for attachment of the extension set 146 as shown in FIGS. 25 and 26. The turning of the outer barrel 112 also allows the needle safety to activate into the retracted position shown in FIG. 24 substantially as described above. A blunt cannula 148 can be provided in the extension set connector to penetrate the septum 130 of the set as shown in FIG. 26. The disposable launcher or inserter assembly can then be removed and discarded.

Figure 27:
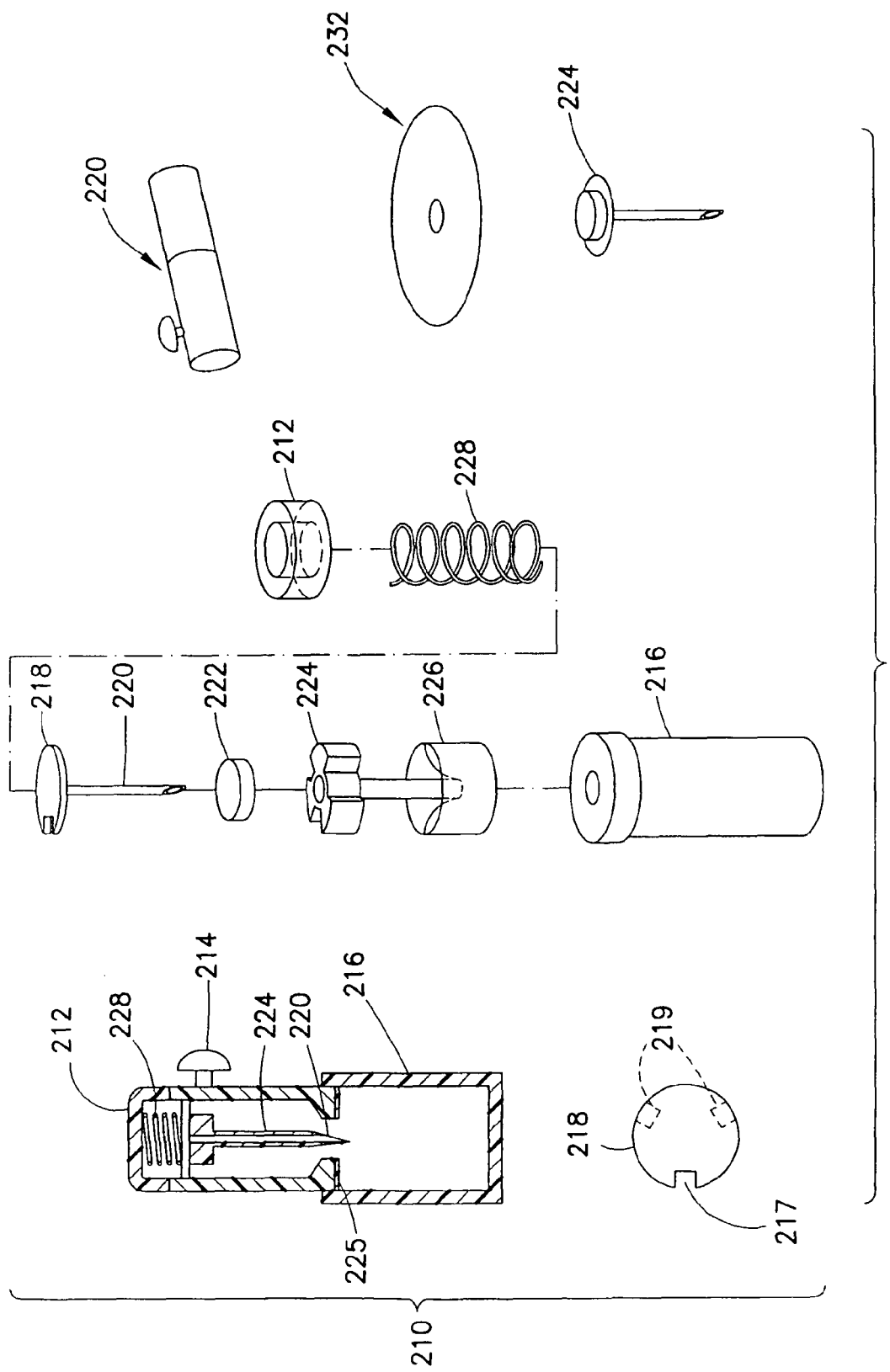
FIG. 27 illustrates additional features for use with the above or other infusion devices.

FIGS. 27-37 illustrate additional features for use with the above or other infusion devices. For example, a clocked inserter can be provided to secure and release an introducer needle 220 and catheter 224. FIG. 27 illustrates a device 210 having a top cap 212, a button 214 and a sterility/safety cap 216. A circular control member 218 is shown having stops 219, and at least one clock 217, and is secured to a top of the introducer needle 220. The circular control member 218 can be held in place by stops 219, and released by aligning the clock 217 with the stops allowing downward movement of the circular control member 218 and introducer needle 220.

Within the top cap 212, the introducer needle 220, septum 222, catheter 224 and septum 226 are positioned beneath a drive spring 228. When the safety cap 216 is removed, rotation of one or more of the elements using the top cap 212 or push button 214 can align the clock 217 with the stops allowing downward movement of the circular control member 218 and introducer needle 220 for placement of the catheter 224. The device 210 is configured to be very small, and to place the catheter 224 using, for example, a reversed BD Autoguard™ inserter, and a 3M Tegaderm™-style adhesive 232. The embodiment of the present invention can be provided with a skin contacting adhesive layer 225 such as a pressure sensitive adhesive (PSA), and an adhesive cover. Precise insertion is achieved by removing the adhesive cover and securing the infusion set to the infusion site via the adhesive layer 22, which permits the user to activate the inserter or place the catheter at the proper alignment and depth. In doing so, the adhesive at or very near the insertion site secures the skin surface such that the introducer needle and catheter, or in-dwelling catheter are driven into the skin surface in a manner to minimize the risk of tenting at needle insertion.

Figure 28:
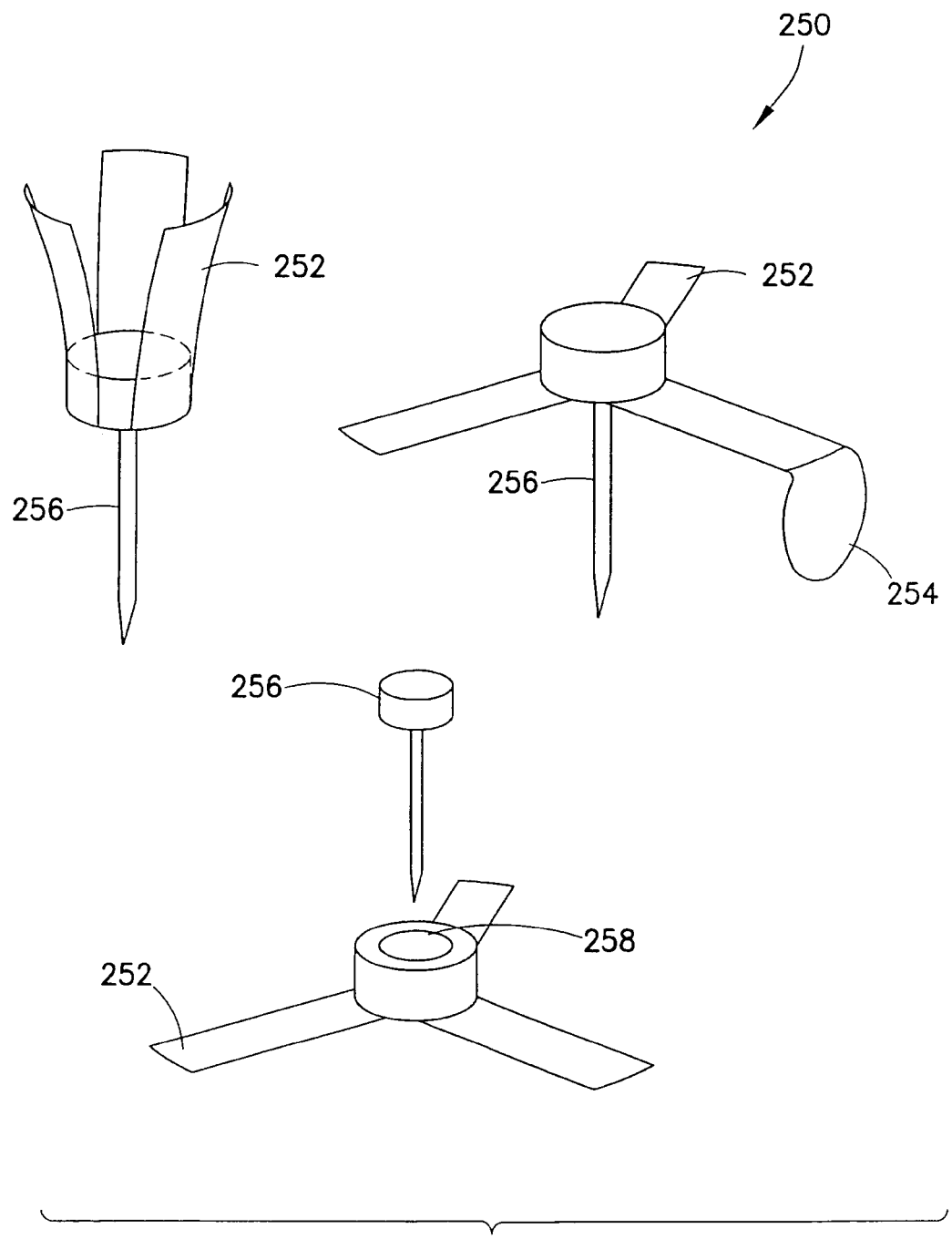
FIG. 28 illustrates views of a stabilizer for use with the above or other embodiments of the present invention.

FIG. 28 illustrates another feature for use with the above or other infusion devices. Specifically, FIG. 28 illustrates views of a catheter stabilizer 250 for use with the above or other embodiments of the present invention. The catheter stabilizer 250 can be molded as a separate part, using materials such as Vialon™, or stamped from foam or other similar materials. The catheter stabilizer 250 comprises a plurality of arms or stabilizers 252, one or more having an adhesive and backing 254. A press-in catheter 256 can then be positioned within a central opening 258 of the catheter stabilizer 250. The stabilizers 252 can be adhesively secured to a surface to stabilize the catheter 256 during use.

Figure 29:
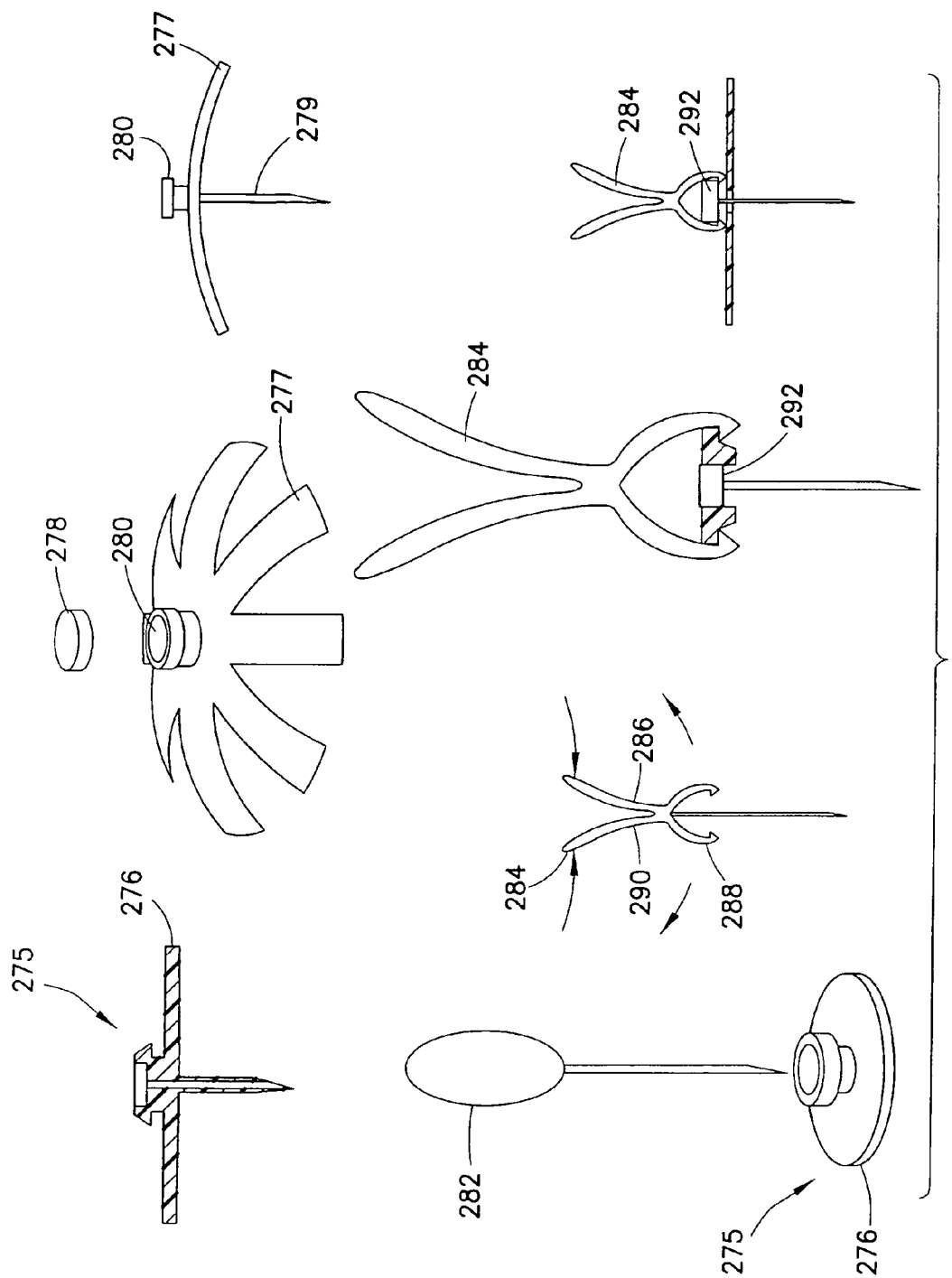
FIG. 29 illustrates views of another stabilizer for use with the above or other embodiments of the present invention.

FIG. 29 illustrates views of another catheter stabilizer for use with the above or other embodiments of the present invention. The catheter stabilizer 275 can be molded as a one-piece, molded catheter/hub stabilization part, using a polymeric material such as Teflon™ or BD Vialon™ biomaterial, or stamped from foam or other similar materials. The catheter stabilizer 275 comprises a circular stabilizer 276 or plurality of wings 277, one or more having an adhesive and backing as described above. A catheter 279 can be provided at a first side and opposite, a septum 278 can be positioned within a central opening 280 of the catheter stabilizer 275 to stabilize the catheter during use. As shown in FIG. 29, a manual inserter 282 or 284 can be used. The first inserter 282 is an introducer needle and handle 282. The second inserter 284 is shown having compressible handles 286 to move grasping arms 288 at an opposite end, via a living hinge 290 therebetween. The grasping arms 288 can comprise snap features configured to grab similar features of a septum, hub and needle 292.

FIGS. 30A-30D illustrate views of an exemplary strain relief member for use with the above or other exemplary embodiments of the present invention. The exemplary strain relief member of FIGS. 30A and 30B comprises a strap-type latch 300 that can be used with a set, such as the exemplary set 306 and tube 304. The latch 300 can be adhesively secured to a skin surface some distance from the set 306, or can be incorporated with the set 306. Once in position, the tube 304 can be pressed into the latch 300, which serves to absorb any strain imparted on the tube 304.

Figure 30A:
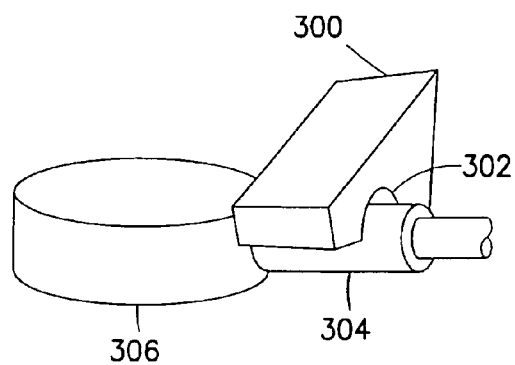
FIGS. 30A-30D illustrate views of a strain relief member for use with the above or other embodiments of the present invention.
Figure 30B:
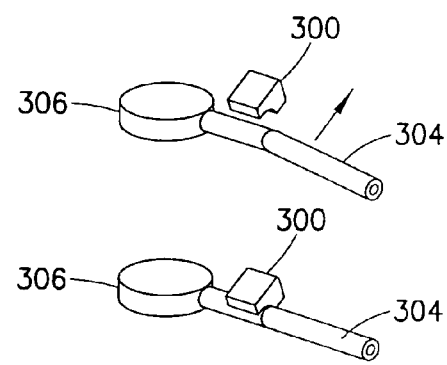
Figure 30C:
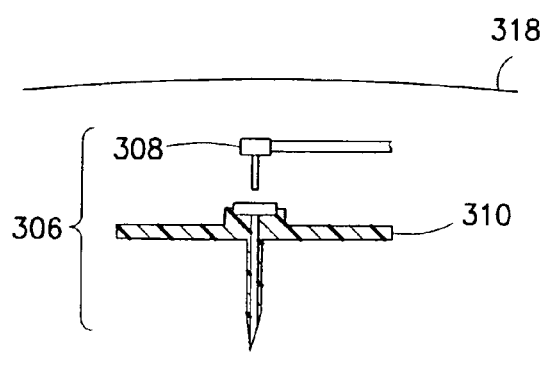
Figure 30D:
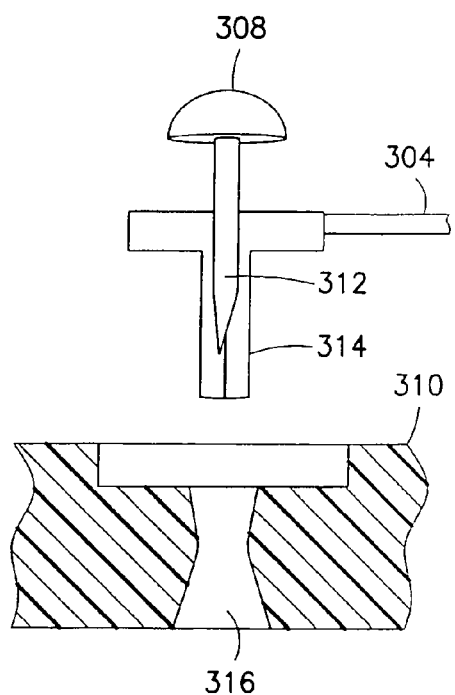

FIGS. 30C and 30D also illustrate views of an exemplary rivet-type tube set connector for use with the above or other exemplary embodiments of the present invention. The exemplary strain relief member comprises a rivet connector 308 and a rivet receiving base 310. Such a set can use a rivet connector 308 which is configured to expand a distal end when pressed. The expanding distal end, if first placed into an opening of the base 310, secures the rivet 308 to the base 310. Specifically, the rivet 308 can be proved with a slidable member 312 in a tube connecting end 314. When placed into a contoured opening 316 of the base 310, pressing the rivet 308 expands the tube connecting end in the opening 316 of the base 310 to secure the tube 304 to the set. In such exemplary embodiments, on or more of the elements can be secured using an adhesive or covering 318, such as Tegaderm™.

Figure 31A:
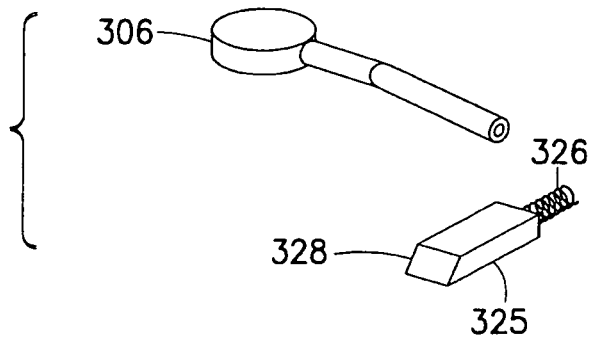
FIGS. 31A-31E illustrate views of a securing member for use with the above or other embodiments of the present invention.
Figure 31B:
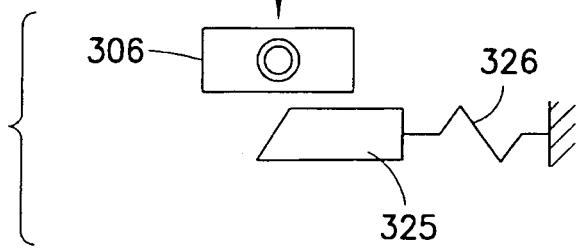
Figure 31C:
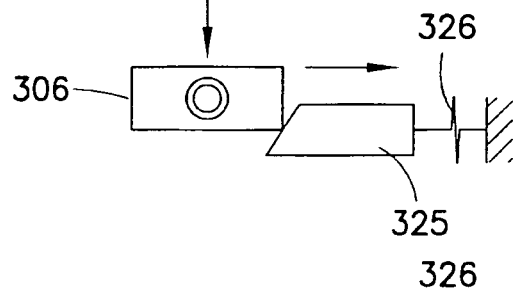
Figure 31D:
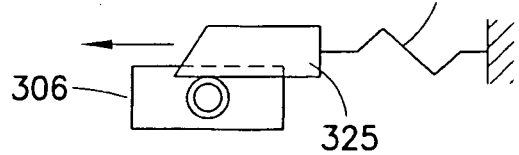
Figure 31E:
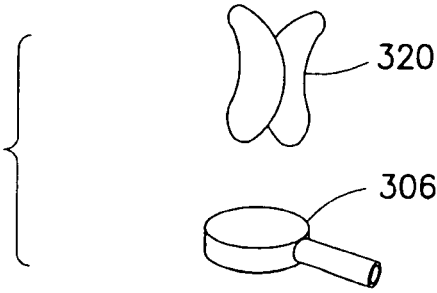

FIGS. 31A-31E illustrate views of another securing member for use with the above or other embodiments of the present invention. The securing member 325 can be used with a set, such as the set 306 described above. The securing member 325 can comprise a spring 326 and an incline 328. The securing member 325 can be adhesively secured to a skin surface some distance from the set 306, or can be incorporated with the set 306. Accordingly, as a set 306 is positioned as illustrated in FIG. 31B, the set 306 can contact the incline 328 such that the securing member 325 is deflected to the side compressing the spring 326 as illustrated in FIG. 31C, but returns to a position above the set 306 after placement as illustrated in FIG. 31D, such that the set 306 is secured. A deployment device, such as a fuse-puller style device 320 as illustrated in FIG. 31E can be used to defeat the securing member 325 to place or remove the set 306.

Figure 32A:
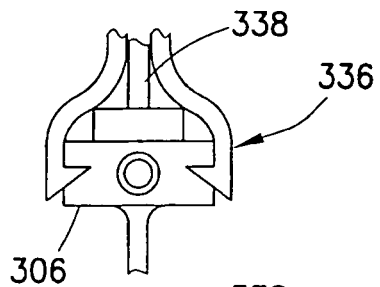
FIGS. 32A-32E show another embodiment in which the securing member can be used with a set.
Figure 32B:
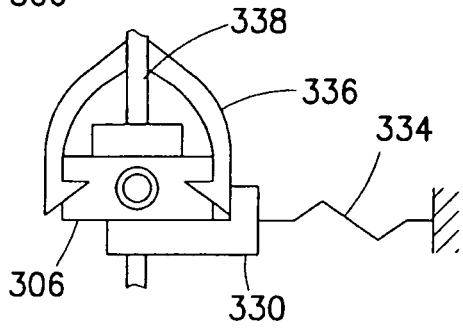
Figure 32C:
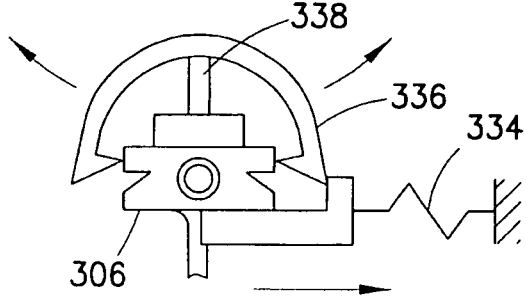
Figure 32D:
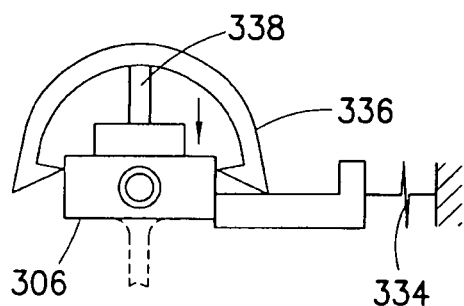
Figure 32E:
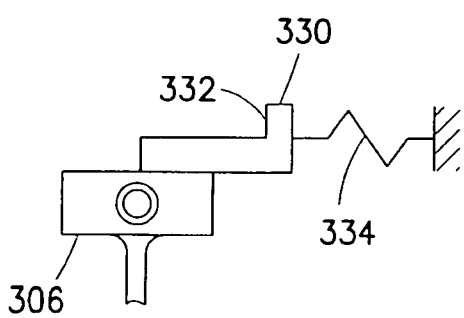

FIGS. 32A-32E show another embodiment in which the securing member 330 can be used with a set, such as the set 306. The securing member 330 can comprise a spring 334 and a shoulder 332 as illustrated in FIG. 32E. The securing member 330 can be adhesively secured to a skin surface some distance from the set 306, or can be incorporated with the set 306. Accordingly, as a set 306 is positioned as illustrated in FIGS. 32A and 32B, the securing member 330 is deflected to the side by the inserter arms 336 as the arms move outward to release the set 306, thereby compressing the spring 334 as illustrated in FIGS. 32C and 32D. The securing member 330 returns to a position above the set 306 after placement by the plunger 338 as illustrated in FIG. 32E, such that the set is secured.

Figure 33:
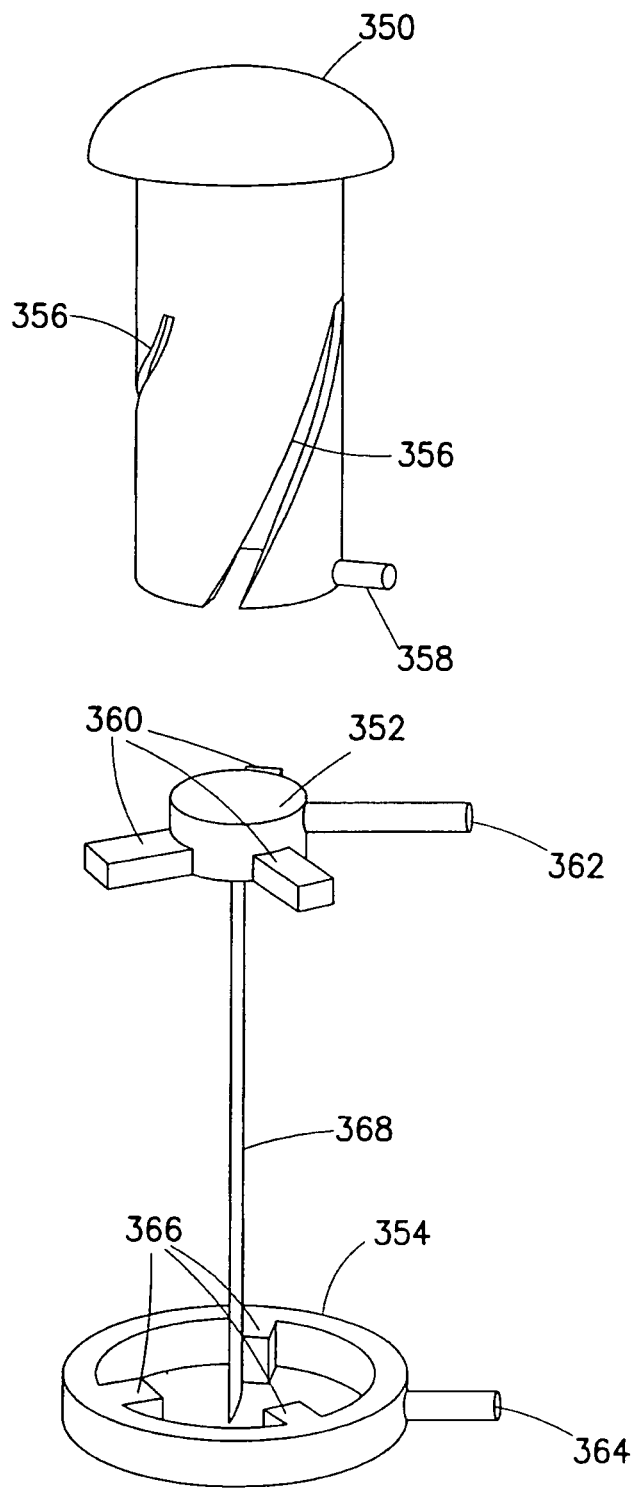
FIG. 33 illustrates views of a top-push button for use with the above or other embodiments of the present invention.

FIG. 33 illustrates views of a top-push button for use with the above or other embodiments of the present invention. The button 350 can be used with a needle hub 352, and a trigger 354. The needle hub 352 comprises an introducer needle 368, alignment pins 360 and pin 362 to engage an outer enclosure to prevent the needle hub 352 from rotating. The trigger 354 comprises alignment pins 366 and pin 364 to engage a guide slot 356 of the button. The button 350 is configured to be pushed downward into the device, and comprises guide slots 356 with a pitch to rotate pin 364 of the trigger 354 for releasing the needle hub 352. As the button 350 is pushed, the trigger 354 is rotated and moves pins 366 from blocking pins 360 allowing the needle hub 352 to release and place the introducer needle or in-dwelling catheter 368 into the skin surface. The button 350 further comprises a pin 358 to engage the outer housing for further guidance and control of the button.

Figure 34A:
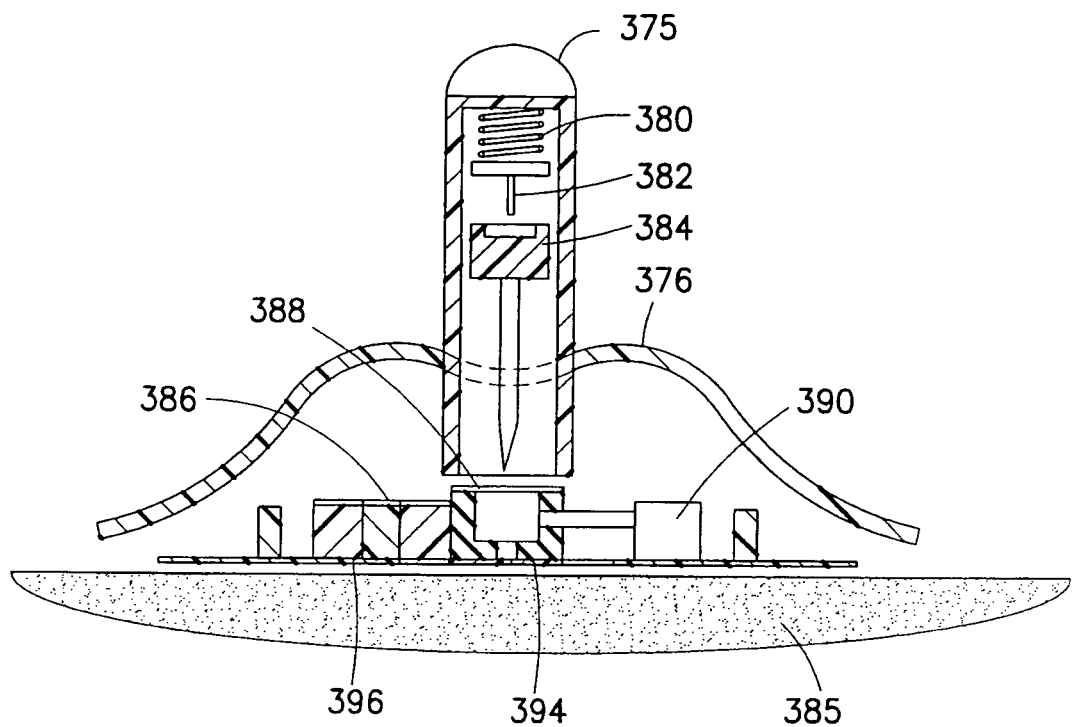
FIGS. 34A and 34B illustrate views of a pen-style actuator for use with the above or other embodiments of the present invention.
Figure 34B:
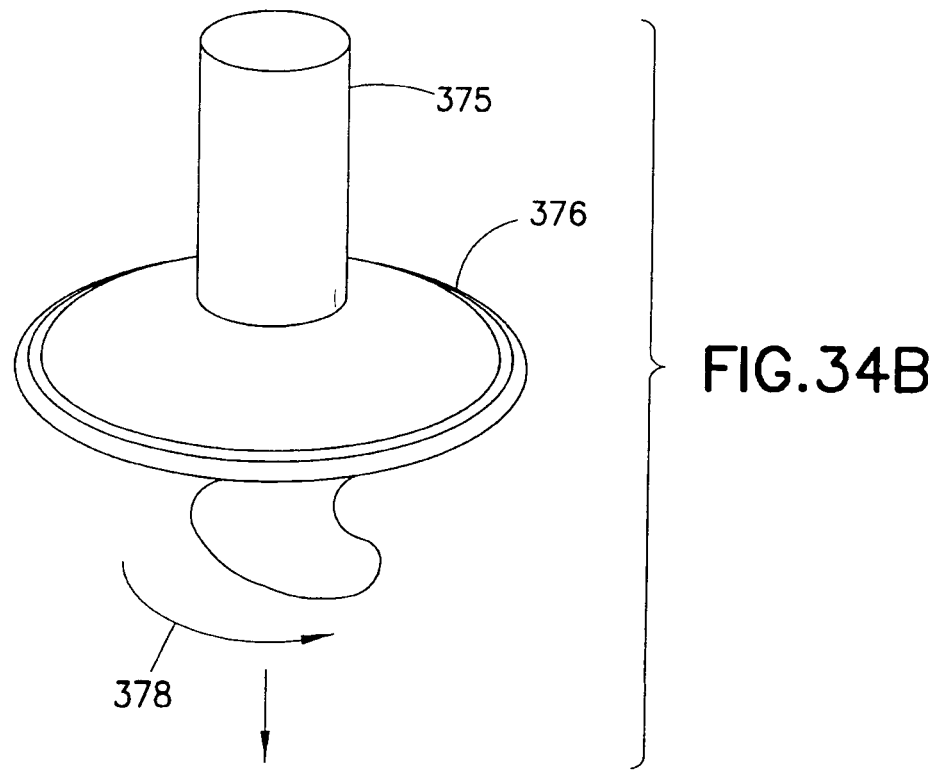

FIGS. 34A and 34B illustrate views of a pen-style actuator 375 for use with the above or other embodiments of the present invention. The actuator 375 comprises a drive spring 380, introducer needle 382, and septum and/or catheter 384 as illustrated in FIG. 34A. The actuator 375 can be positioned though a dome 376 which is configured to contain the contents therein and place an outer adhesive ring 396 and an inner adhesive ring 394 beneath the septum 388. Two or more molded flexures 386 can be provided between the adhesive rings 396 and 394, and between a septum or U-shaped gasket 388 and a tubing connection 390. The dome 376 is shaped and configured to flex, so as to be user-friendly.

The embodiment of the present invention can be provided with a skin contacting adhesive layers 394 and 396 such as a pressure sensitive adhesive (PSA), and an adhesive cover 378. Precise insertion is achieved by removing the adhesive cover 378 and securing the infusion set to the infusion site 385 via the adhesive layers 394 and 396, which permits the user to activate the inserter or place the catheter as described below at the proper alignment and depth. In doing so, the adhesive at or very near the insertion site secures the skin surface such that the introducer needle and catheter, or in-dwelling catheter are driven into the skin surface in a manner to minimize the risk of tenting at needle insertion.

In an exemplary use, the user removes an adhesive layer cover 378 and places the device on a skin surface 385. The actuator 375 can then be used to place the introducer needle 382 and catheter 384, or an in-dwelling catheter. The actuator 375 and dome 376 can then be removed with the introducer needle. As noted above, the flexures 386 can be provided between the adhesive rings 396 and 394, and between the septum 388 and the tubing connection 390, and can comprise for example, molded S-shaped members extending between the septum 388 of the inner ring to the outer ring as more clearly shown in FIG. 37. Accordingly, once the catheter 384 is in place, the flexures 386 stabilize the outer adhesive ring 396 to the inner adhesive ring 394 beneath the septum 388.

Figure 35A:
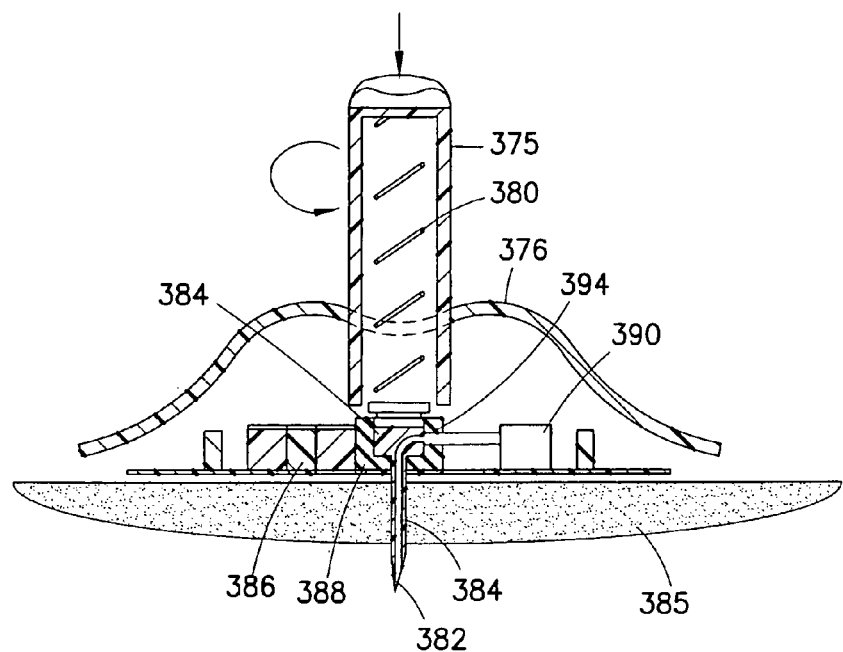
Figure 35B:
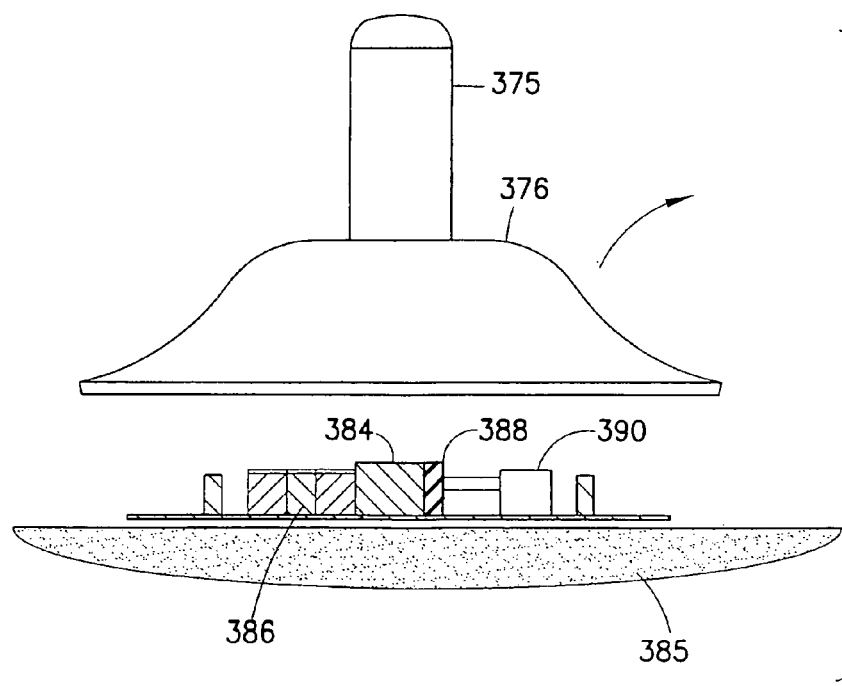

FIGS. 35A, 35B, 36A-36B and 37 illustrate views of the use of the device of FIG. 34. In FIG. 35A, a top of the actuator 375 is pressed to deploy the introducer needle 382 and catheter 384 into the infusion site 385, and turning the actuator 375 releases the actuator and dome from the set as shown in FIG. 35B, leaving the catheter 384 within the septum 388 and removing the introducer needle 382. FIGS. 36A-36C show views of the placement of a tube set and cap system 392 with the set. The tube set and cap system 392 can be snapped into place with the set as illustrated in FIGS. 36A and 36B.

In one example, the cap 392 can comprise detents 395 to releasably capture detents 398 of the set such that the cap 392 can be releasably secured to the set as illustrated in FIG. 36B. Further, the cap 392 can be provided with a blunt cannula connector 391 for completing a fluid connection with the tubing connection 390. In such an embodiment, there are fewer and better controlled insertion and connection steps, with limited error points. Use is silent, with painless insertion due to scale. The embodiment also provides an integrated and disposable actuator for every tube set. The integrated inserter is slim, and disposable, with a pen barrel-style, with a low-impact, activation mechanism. Further, the strain relief is provided by inner and outer adhesive rings coupled by flexures to decouple the catheter site from the tubing connection site as illustrated in FIG. 37. Any tugs and pulls can break connections on the outer ring, but do not affect the catheter site. The adhesive is placed on the skin surface first, which minimizes tenting, improves stability and accuracy, and minimizes kinking at insertion. In yet other embodiments, the flexures 386 can be omitted so that the septum 388 is totally independent from outside movement. Further, the device comprises inherent dampening of motion due to the completion of the fluid path with, for example, a U-shaped gasket.

In exemplary embodiments of the present invention, the housings, hubs and other elements can be constructed of molded plastic materials, polycarbonate, thermoplastic polymers such as polyethylene terephthalate (PET and PETG), or similar materials. Springs and introducer needles can be constructed of stainless steel or similar materials. Although the embodiments described above are dimensioned and configured for subcutaneous injection, they can also be used for other types of injection, such as intradermal or intramuscular injection.

In current infusion sets which deliver insulin or other medicament to the subcutaneous layer, the catheter is not isolated from any undesired outside forces, which may cause pain when translated to the catheter which then moves within the skin. Also, other devices face problems of premature or unintended catheter removal when the device is bumped if the catheter is not isolated from the outside forces. In embodiments of the present invention, the catheter can be isolated from outside forces by at least one flexible or resilient feature, or protected from outside forces by at least one covering member.

As noted above, exemplary embodiments of the present invention provide a catheter and extension set for insulin infusion from an insulin pump or other medicament supply. The device is placed upon the skin surface of a user with adhesive, such as an adhesive layer disposed upon a base member, then activated by pressing a button, whereupon insertion of the introducer needle and catheter are performed manually or automatically using energy supplied by a drive member, such as a drive spring. Removal of the introducer needle is also performed manually or automatically and the introducer needle is retracted into the outer barrel where it is locked into place using for example, a latch, such that it cannot cause accidental needle sticks when the launcher or inserter is removed from the base. The extension set is then attached to the base, and the fluid path to the catheter is completed by a blunt cannula that pierces the septum of the base. The exemplary system is then connected to an infusion pump or other supply, and primed for use. In doing so, the device is configured to insert the catheter by pressing a button without requiring the user to load the catheter into a launching device or inserter, or loading the launching device in some way by the user. The device is further configured to retract the introducer needle and/or implement other safety features.

Since the element being launched comprises only the catheter and needle hub subassembly, the mass is much smaller than what is launched with existing devices. The effect of this is that the energy requirements of the device are less, leading to smaller, quieter devices, with further advantages of being environmentally "greener" (i.e., requiring less construction materials, construction steps, and generating less waste), and with less noise and impact upon activation. Further, since the adhesive layer is already in place on the skin surface of the user, manipulation of the adhesive after insertion of the catheter is less likely to occur and thereby eliminating a common cause of kinking of the catheter.

Still further, exemplary embodiments are configured to be smaller than comparative devices, yet accomplish both insertion and retraction of the introducer needle. Further, because the device is packaged and shipped in an assembled and loaded state, there are inherently fewer pieces to carry and preparatory steps than associated with comparative devices. Such advantages are realized, in part, due to the requirement for activation or launching a smaller mass. In exemplary embodiments provided with flexible sears for activation control, the embodiments have smaller activation forces and larger part tolerances, as compared to other exemplary embodiments.

Figure 38:
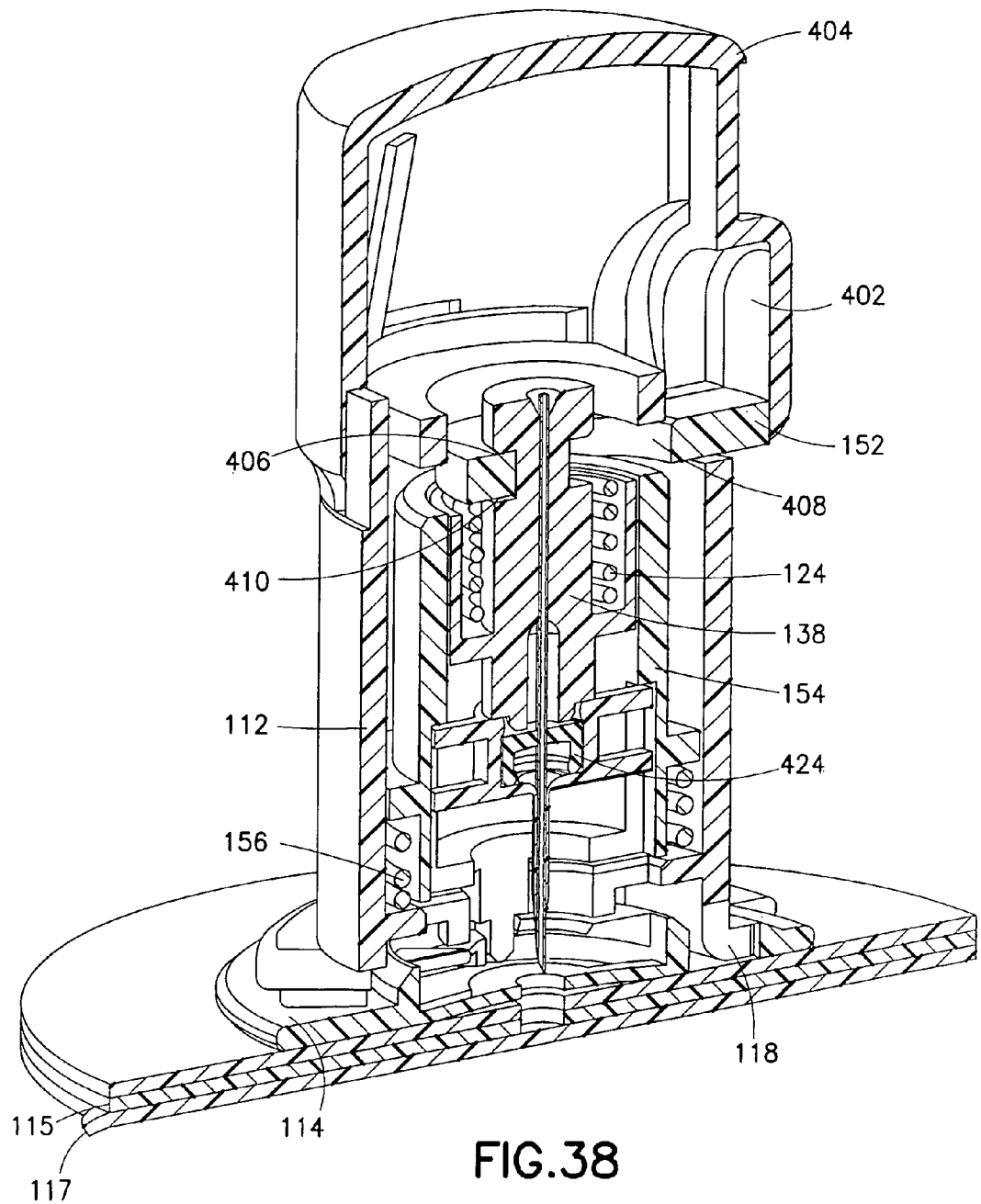
FIGS. 38-41 illustrate views of an infusion device utilizing a side-push button in accordance with a third embodiment of the present invention.

The first and second embodiments described above used an exemplary top-push activation button providing a number of advantages. In yet another embodiment of the present invention, similar or other advantages can be achieved using a side-push activation button. That is, instead of pressing a top or top-mounted button into a device (i.e., toward the skin surface of the user) as described above, the device can be activated by pressing a button located on the side of the device, potentially molded into the outer barrel cap as shown in FIGS. 38-41. FIG. 38 is a sectional view of a device utilizing a side-push button in accordance with a third embodiment of the present invention. The device is substantially as described above in regard to the second embodiment, and comprises an outer barrel 112, a slidable inner barrel cap 152 and inner barrel 154 and a base 114. The base 114 comprises at least one outer barrel retention tab 118 that is configured to rotatably enter openings in the base 114 and be captured at a rotational position by shoulders 122 of the base 114 as described above. A drive spring 124 and a safety spring 156 are also provided to extend and retract an introducer needle.

Figure 39:
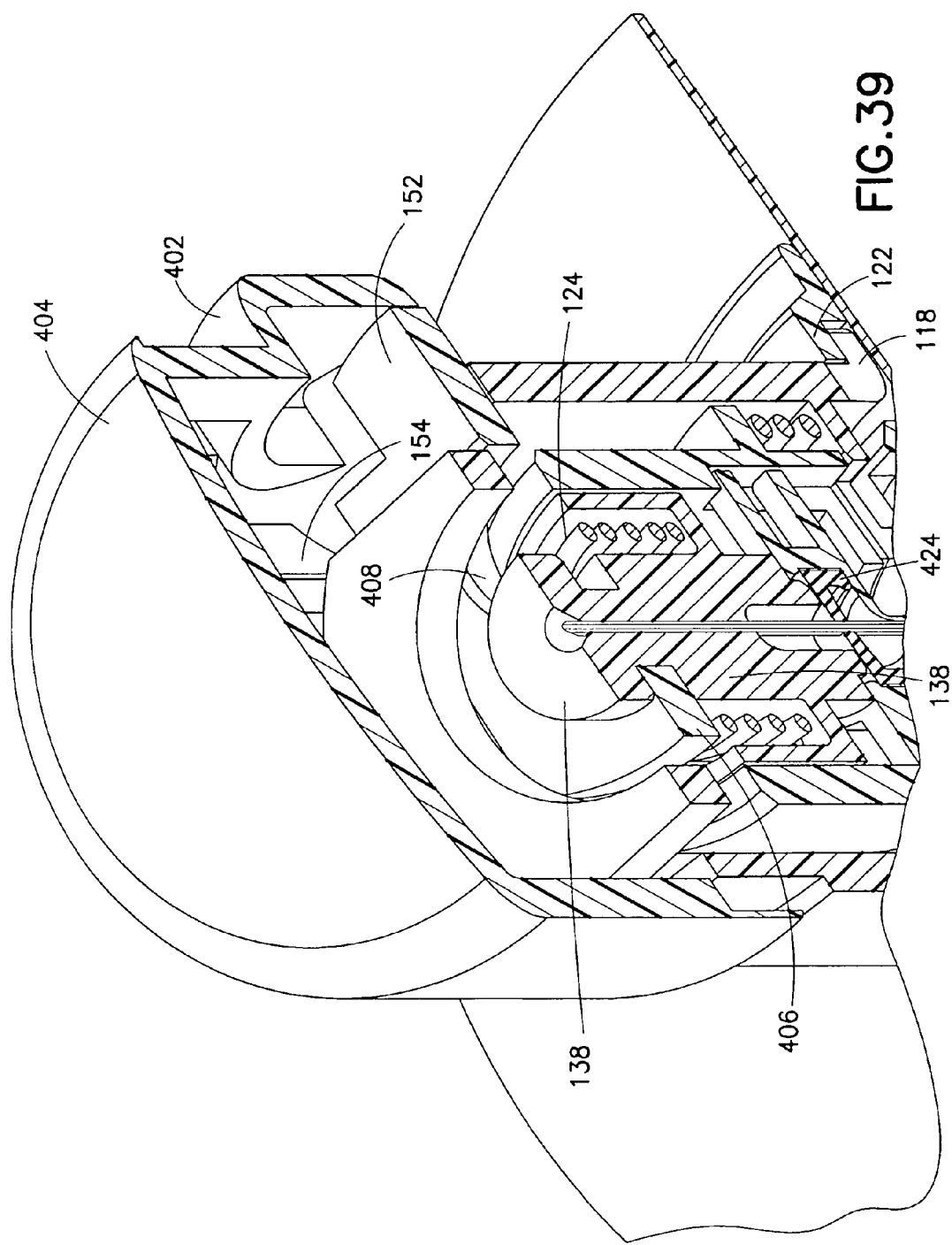
Figure 40:
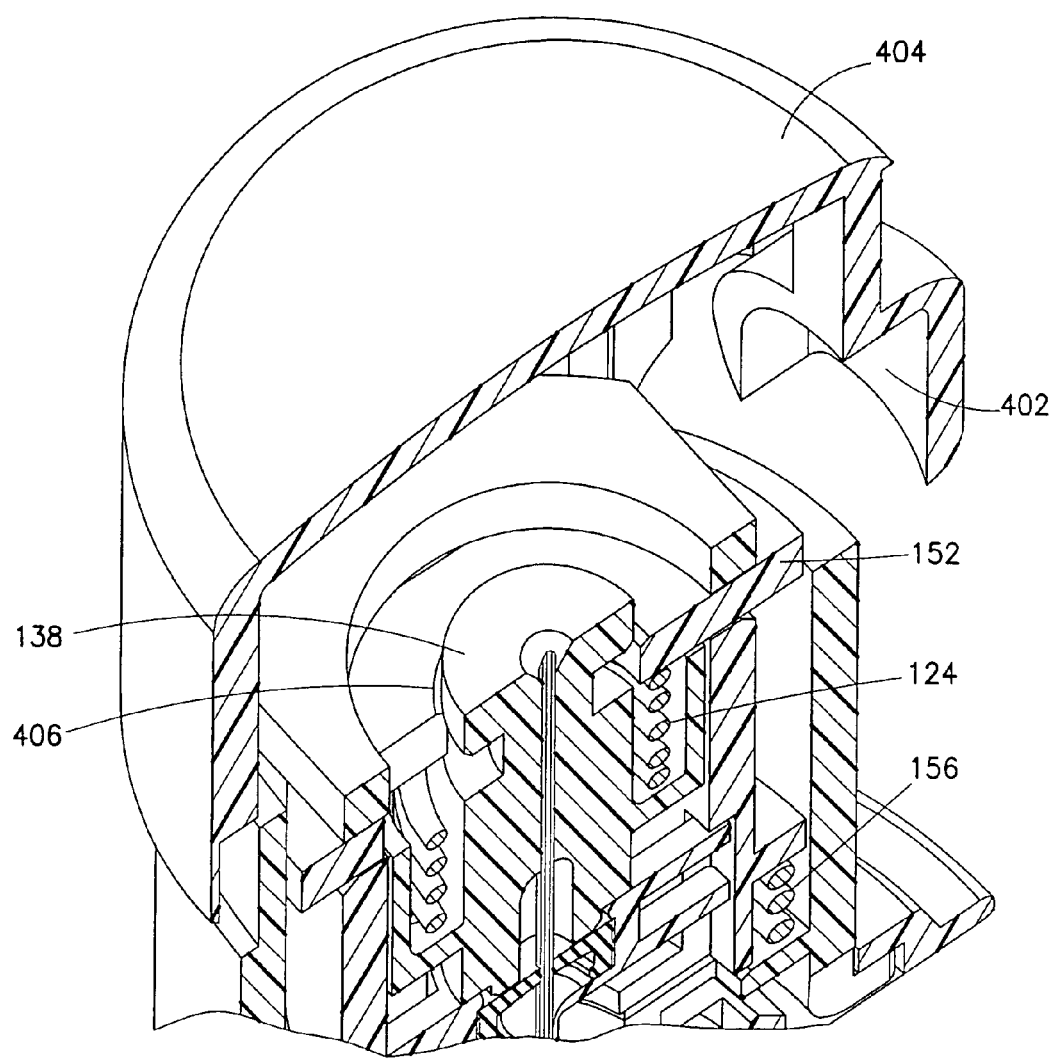
Figure 41:
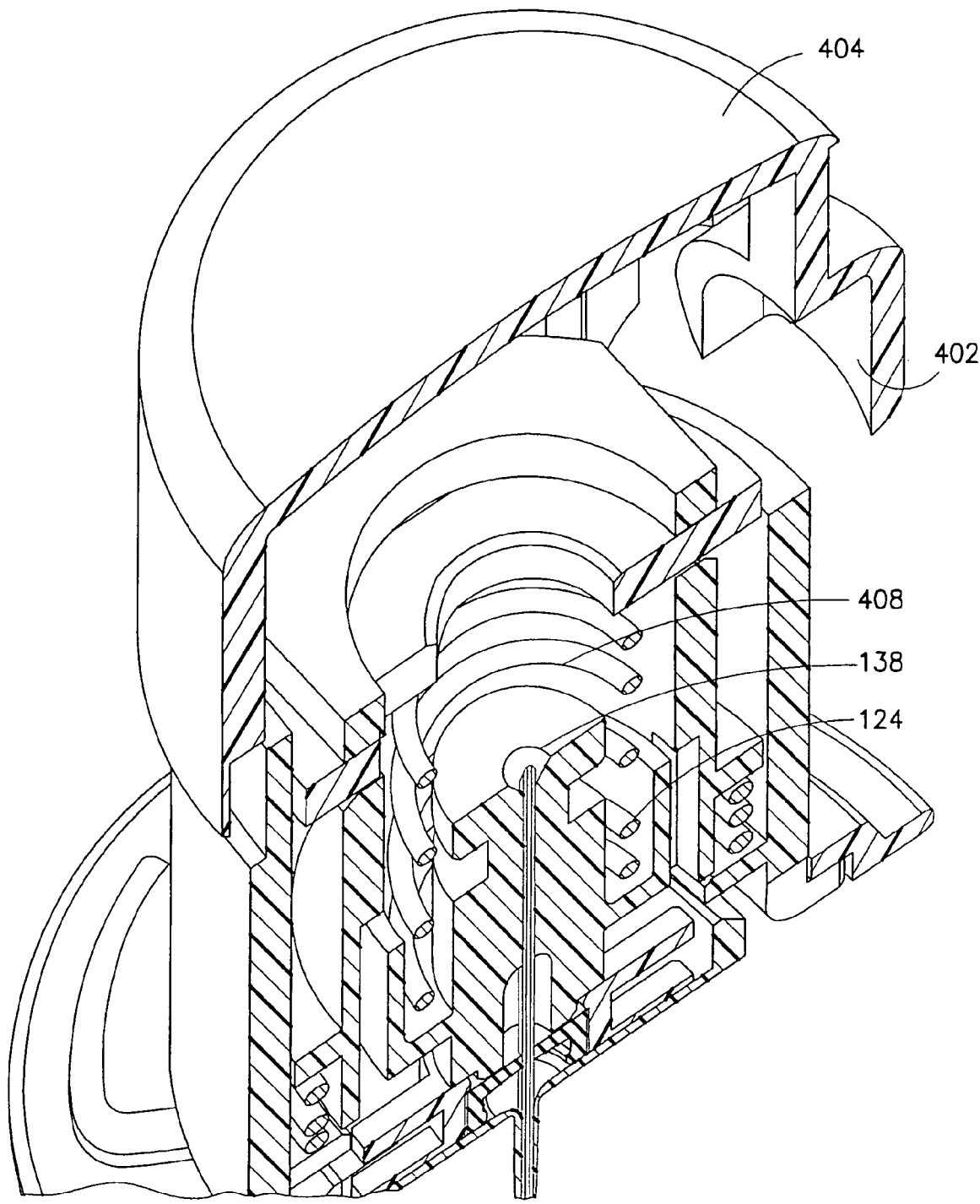

In the third exemplary embodiment shown in FIGS. 38-41, a side-push button 402 and conforming outer barrel cap 404 and inner barrel cap 406 are provided to facilitate a different method of activating the third exemplary embodiment. The side-push button 402 is located on the side of the device, molded into the outer barrel cap 404, and acts upon the slidable inner barrel cap 152 as shown in FIGS. 38 and 39, causing the inner barrel cap 152 to slide to the left. That is, the slidable inner barrel cap 152 comprises an interference side 406 which captures a slot of the needle hub 138 in a first position, and comprises a clearance side 408 which permits the slidable inner cap 152 to be slide toward the needle hub 138 and move the interference side 406 from the slot of the needle hub 138 as shown in FIG. 40. Once the inner barrel cap 152 has advanced to the position shown in FIG. 40, the slot in the needle hub 138 disengages the keyhole slot in the inner barrel cap 152, releasing the needle hub 138 to drive the catheter assembly 424 into the user's skin surface. The catheter assembly 424 can be molded as a single piece or provided with a septum, and can include the septum, introducer needle and catheter, or an in-dwelling catheter.

The embodiment of the present invention can be provided with a skin contacting adhesive layer 115 such as a pressure sensitive adhesive (PSA), and an adhesive cover 117. Precise insertion is achieved by removing the adhesive cover 117 and securing the infusion set to the infusion site via the adhesive layer 115, which permits the user to activate the inserter or place the catheter as described below at the proper alignment and depth. In doing so, the adhesive at or very near the insertion site secures the skin surface such that the introducer needle and catheter, or in-dwelling catheter are driven into the skin surface in a manner to minimize the risk of tenting at needle insertion.

In the embodiment shown, the button 402 can be a molded-in component that drives the inner barrel cap 152 as opposed to a sliding button that has the keyhole slot molded therein. In doing so, the embodiment ensures that the button will not inadvertently become caught on the outer barrel 112 when the needle stick protection mechanism is activated. However, other embodiments of the sliding button can have the keyhole molded in as part of the button. Further, these embodiments can be configured to work with these or any other spring-assisted catheter insertion devices, and/or combined with spring-assisted needle stick prevention features. Such a keyhole triggering configuration can be more robust for shipping and handling than a top-push button embodiment. Also, the embodiment addresses the event where there is a user preference for a side-push button as opposed to a top-push button.

Figure 42:
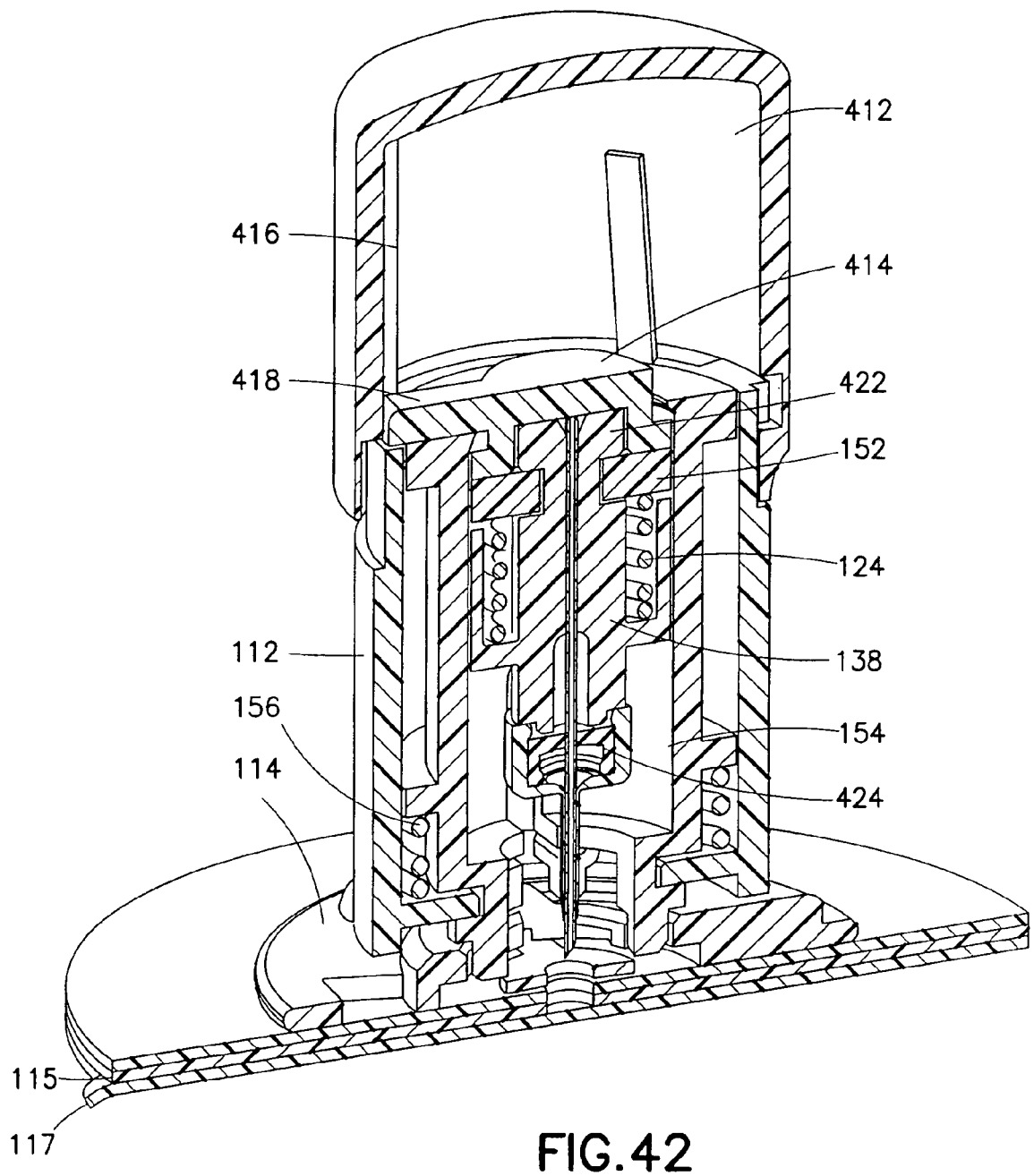
FIGS. 42-45 illustrate views of an infusion device utilizing a rotary button in accordance with a fourth embodiment of the present invention.

In yet another embodiment of the present invention, similar or other advantages can be achieved using a rotary activation button. That is, instead of pressing a top or top-mounted button into a device (i.e., toward the skin surface of the user) as described above, the device can be activated by rotating a button located on the device and, by further rotation, disengage the inserter, insertion mechanism or module, from the base. FIG. 42 is a sectional view of a device utilizing a rotary button in accordance with a fourth embodiment of the present invention. The device is substantially as described above in regard to the second and third embodiments, and comprises an outer barrel 112, inner barrel cap 152 and inner barrel 154 and a base 114. The base 114 comprises at least one outer barrel retention tab 118 that is configured to rotatably enter openings in the base 114 and be captured at a rotational position by shoulders 122 of the base 114 as described above. A drive spring 124 and a safety spring 156 are also provided to extend and retract an introducer needle.

The embodiment of the present invention can be provided with a skin contacting adhesive layer 115 such as a pressure sensitive adhesive (PSA), and an adhesive cover 117. Precise insertion is achieved by removing the adhesive cover 117 and securing the infusion set to the infusion site via the adhesive layer 115, which permits the user to activate the inserter or place the catheter as described below at the proper alignment and depth. In doing so, the adhesive at or very near the insertion site secures the skin surface such that the introducer needle and catheter, or in-dwelling catheter are driven into the skin surface in a manner to minimize the risk of tenting at needle insertion.

In the fourth exemplary embodiment, the user can use one motion to activate the device. That is, a rotary motion can be used to activate the device or inserter of the device, followed by further rotation to activate the safety of the device, the retraction of the introducer needle for needle stick protection, and further rotation to detach the inserter from the base. All actions can be implemented using a single, smooth rotation by the user. In this or other embodiments, tactile and/or audible feedback can be provided to indicate needle insertion, needle retraction, safety activation and removal.

In an exemplary embodiment, the button 412 can be rotated about the remainder of the device, being adhesively secured to the skin surface, and in turn, rotate a trigger 414 via the button slot 416 pressing on a trigger tab 418, as shown in FIG. 42. Activation occurs by rotating the button 412 first to the introducer needle and catheter insertion position, then to the safe position, all in one smooth rotary motion. The drive spring 124 is compressed between the inner barrel cap 152 and the needle hub 138, and is retained by the needle hub sear engagement with the inner barrel cap as shown in FIGS. 42 and 43.

The rotation of the button 412 rotates the trigger 414 via the trigger tab 418, and rotation of the trigger 414 rotates a bar-shaped needle hub sear 422. A slot 420 is provided in the inner barrel cap 152 such that, when the bar-shaped needle hub sear 422 is rotated into alignment with the slot 420, the drive spring 124 will drive the needle hub 138, including the introducer needle and catheter assembly 424, into the skin of the user. Such a rotation triggering configuration can also be more robust in shipping and handling than a top-push button embodiment, and the disclosed embodiments address the situation where there is a user preference for a rotation button as opposed to a top-push button.

Activation of the needle safety, or needle tip shielding, can be achieved by disengaging the tabs in the outer barrel from the base, which also allows removal of the inserter from the base as described above. Further, the disclosed embodiments can be used with any number of triggering modes, such as one wherein the needle hub rotates until the molded-in tabs align with the slots in the inner barrel. Still further, the disclosed embodiments can be configured to work with these or any other spring-assisted, catheter insertion devices, and/or combined with spring-assisted needle stick prevention features.

Figure 43:
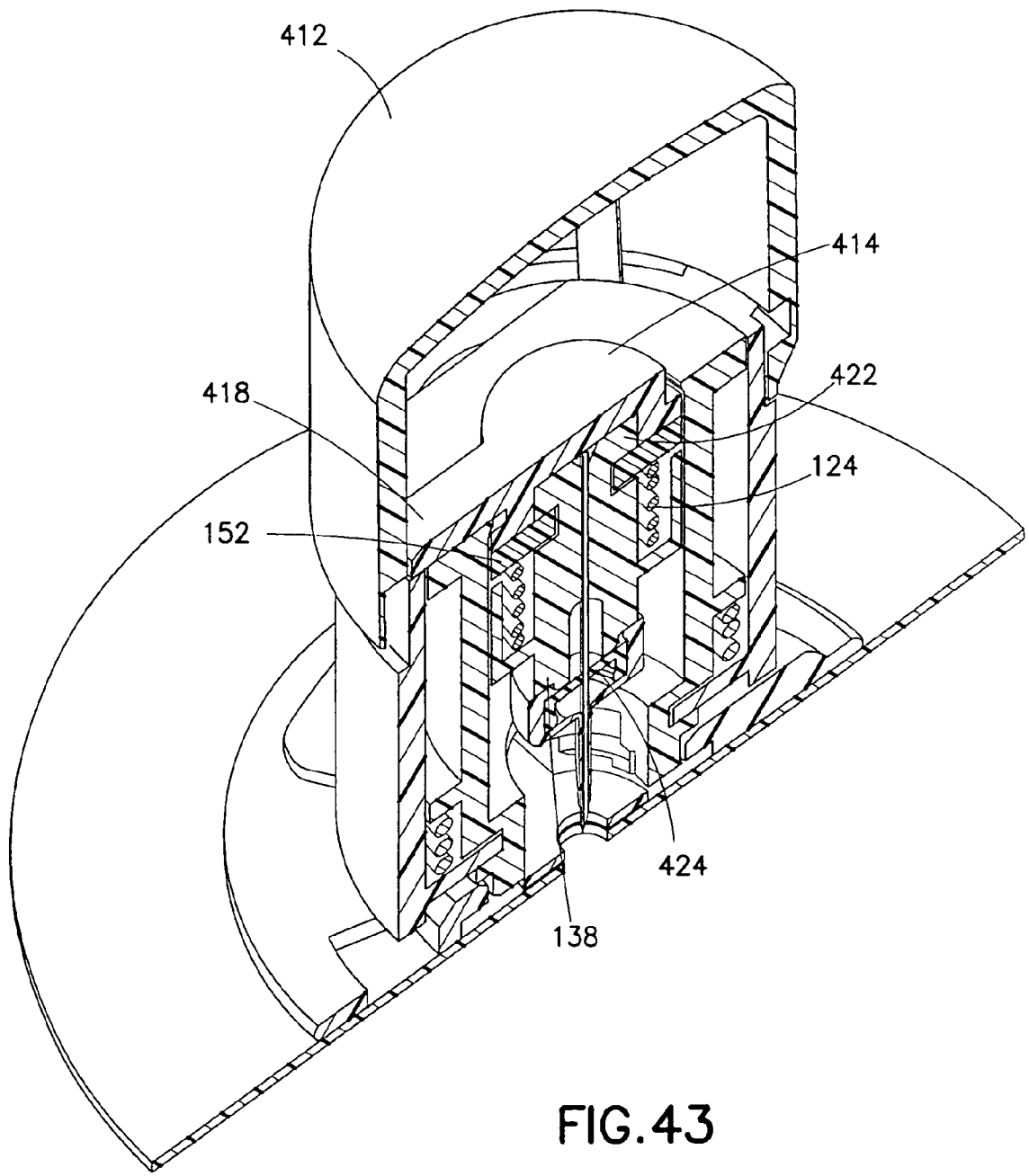
Figure 44:
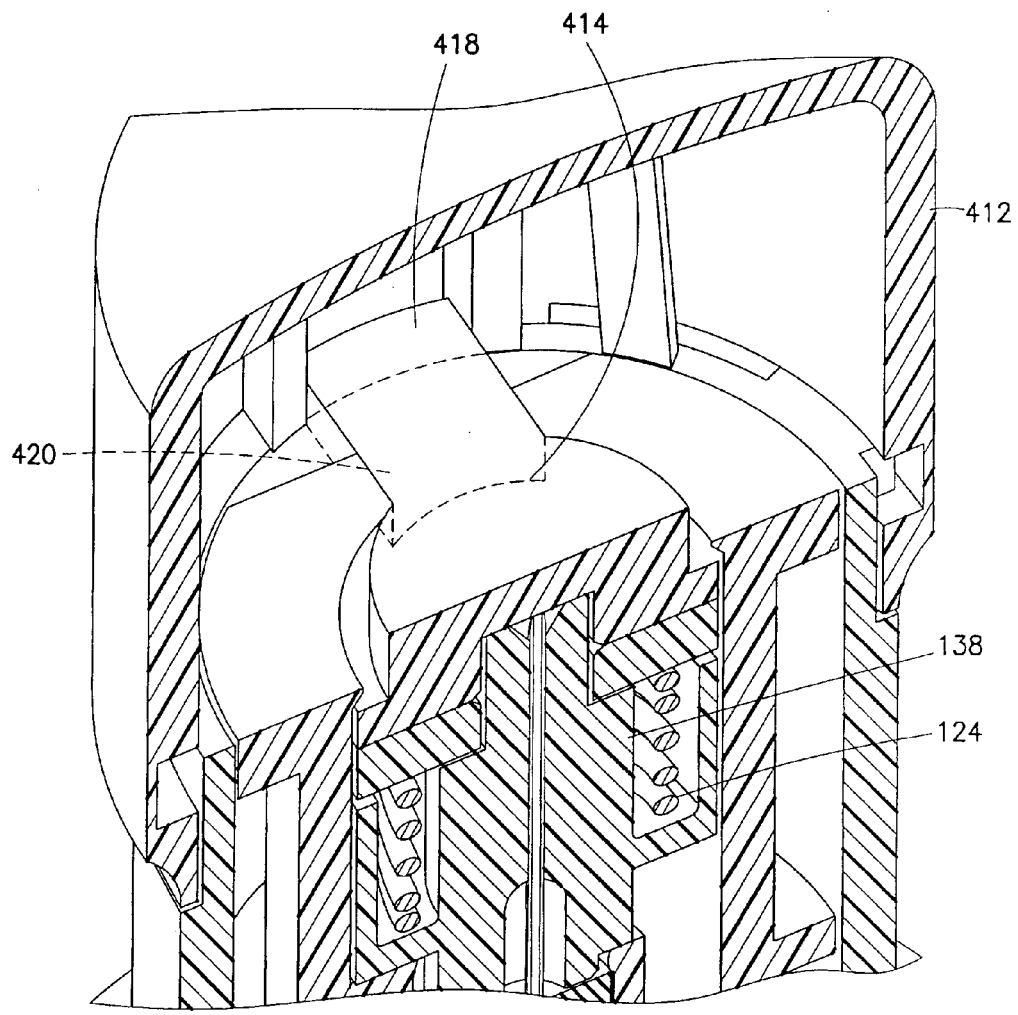
Figure 45:
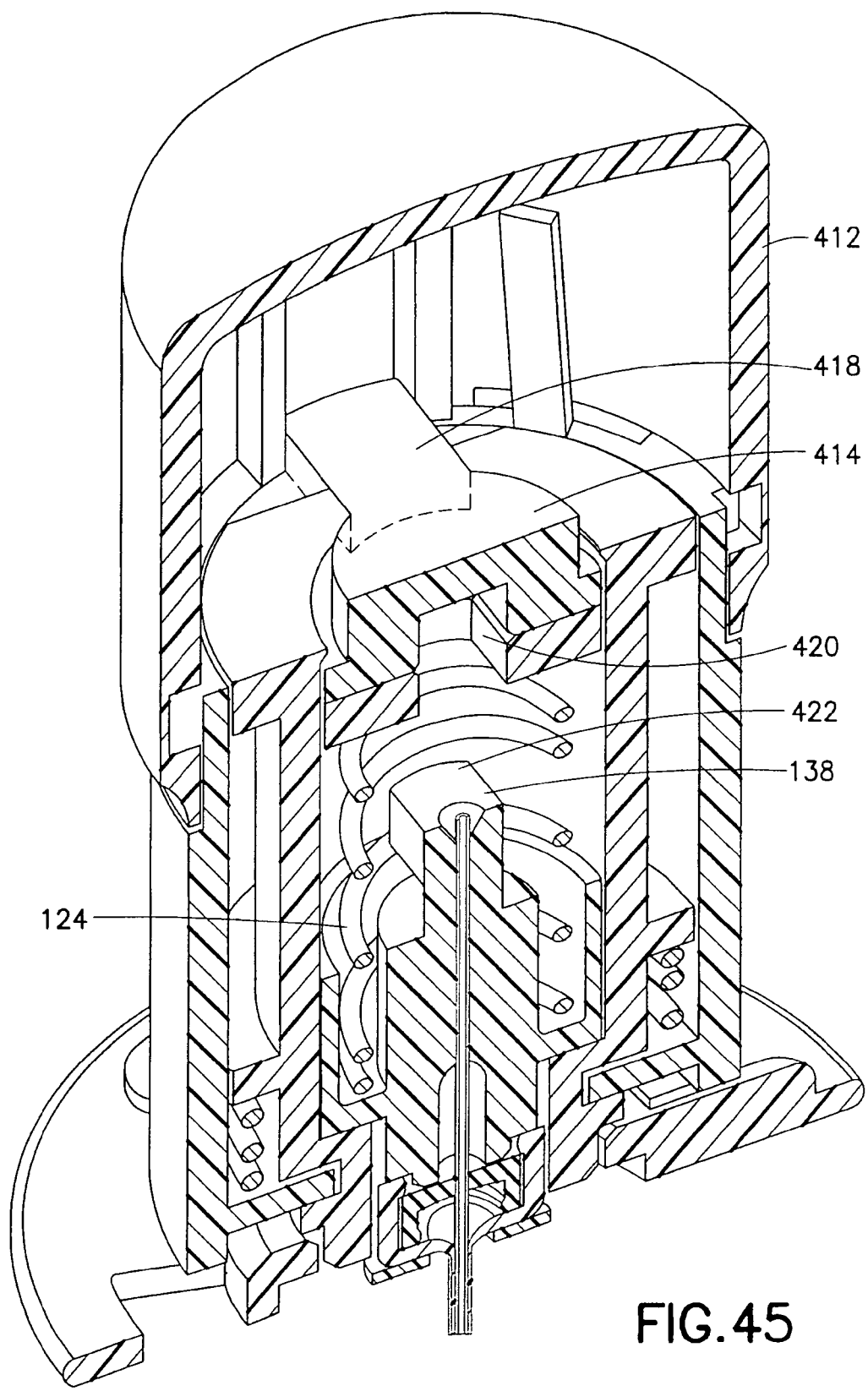

FIG. 43 illustrates the drive spring 124 in a loaded state as secured by the needle hub sear 422 and the inner barrel cap 152. FIG. 44 illustrates the needle hub sear 422 and the inner barrel cap slot 420 coming into alignment, such that the needle hub 138 will be released from the inner barrel cap 152, allowing the needle hub 138 to drive the introducer needle and catheter assembly into the users skin surface. FIG. 45 illustrates the needle hub in a final position after being released from the inner barrel cap.

In these and other exemplary embodiments of the present invention, a number of features can be provided to prevent premature activation of the introducer needle. The following embodiments of the present invention describe a number of such features including a manually-activated interlock designed to prevent premature activation and features to prevent separation of the extension set from the base. Such features can include elements for interlocking the outer barrel, hence the integrated/removable inserter assembly, to the base, as well as the extension set to the base, with variants of the same mechanism.

In such embodiments, there may be a concern that users can accidentally activate the needle stick protection mechanism before deploying the catheter assembly insertion mechanism, thereby rendering the device useless. Additionally, there can be a need to prevent rotation of the extension set top of the devices described above once it has been attached to the base in order to prevent inadvertent separation of the extension set and base, and interrupting the flow of insulin. A similar feature to that used to prevent premature activation of the needle stick protection mechanism can be added to the extension set top to prevent separation of the extension set and base.

FIG. 46 illustrates a locking latch to prevent rotation of elements. As shown in FIG. 46, a latch 425 has been added to the outer barrel 12 of the embodiments described above. The latch 425 rotates about a molded pivot point 427 and engages a slot 426 in the base 14, thereby locking the two from significantly rotating relative to one another, thus preventing inadvertent detachment of the inserter and subsequent activation of the needle stick prevention mechanism.

After insertion of the catheter has been accomplished, and the user is ready to detach the inserter, the user can do so by pressing the button 428 as shown in FIG. 47, thereby rotating the latch 425 out of the engagement with the slot 426 in the base 14. Once the latch 425 has been disengaged from the slot 426, the inserter assembly may be rotated and removed, at which time the needle stick protection mechanism will activate and retract the introducer needle from the catheter.

Figure 48:
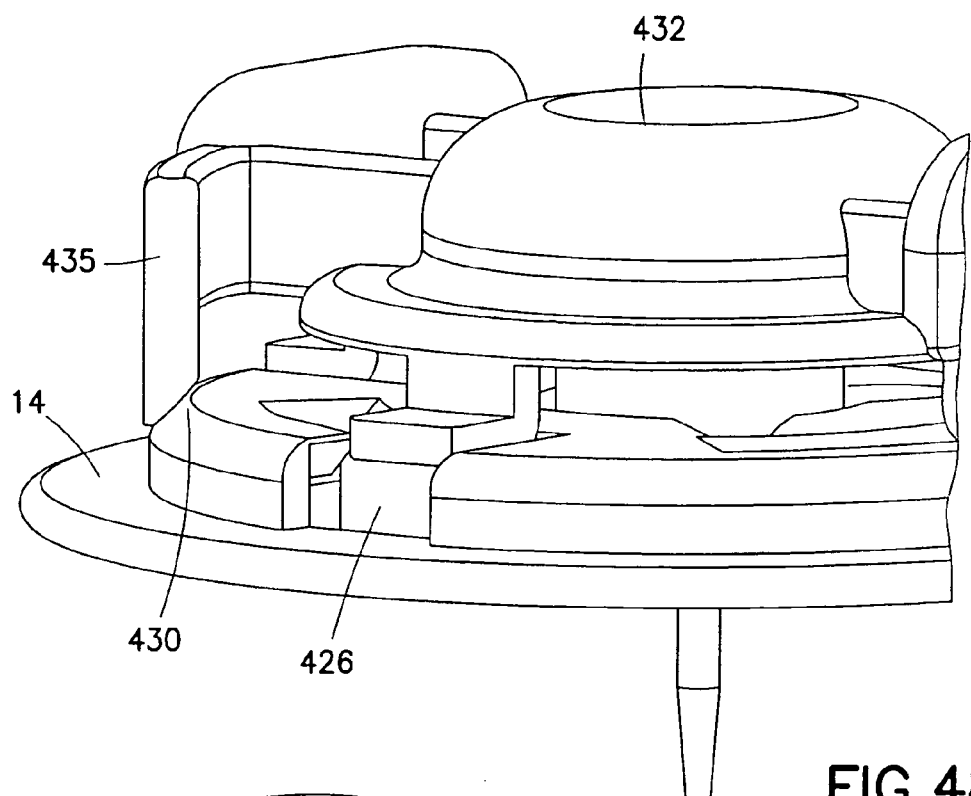
Figure 49:
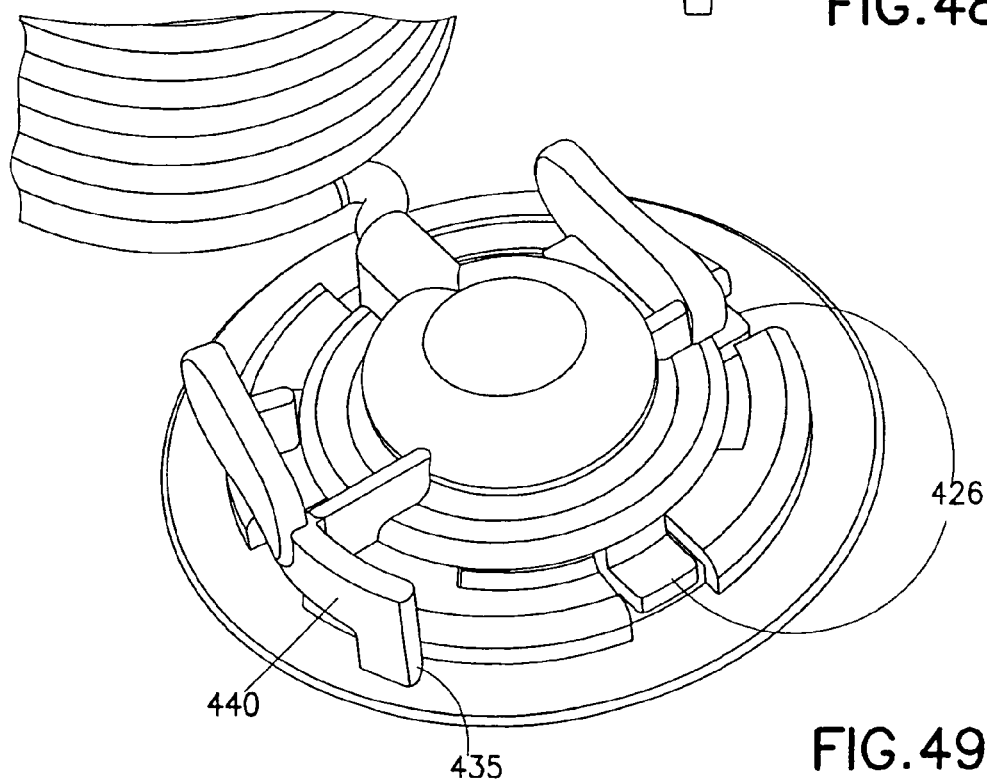
Figure 50:
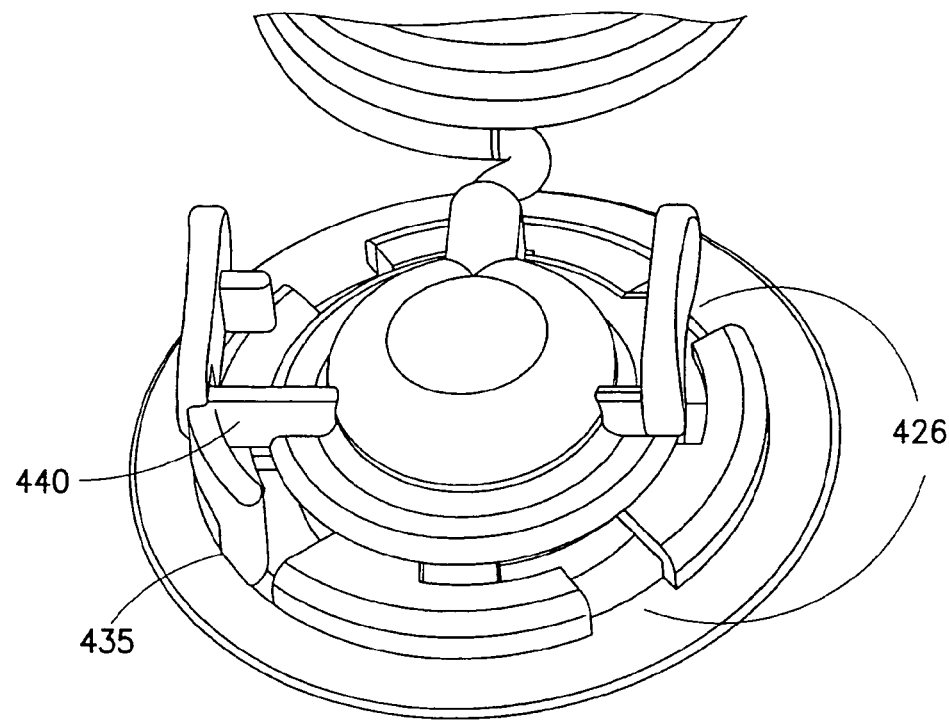
Figure 51:
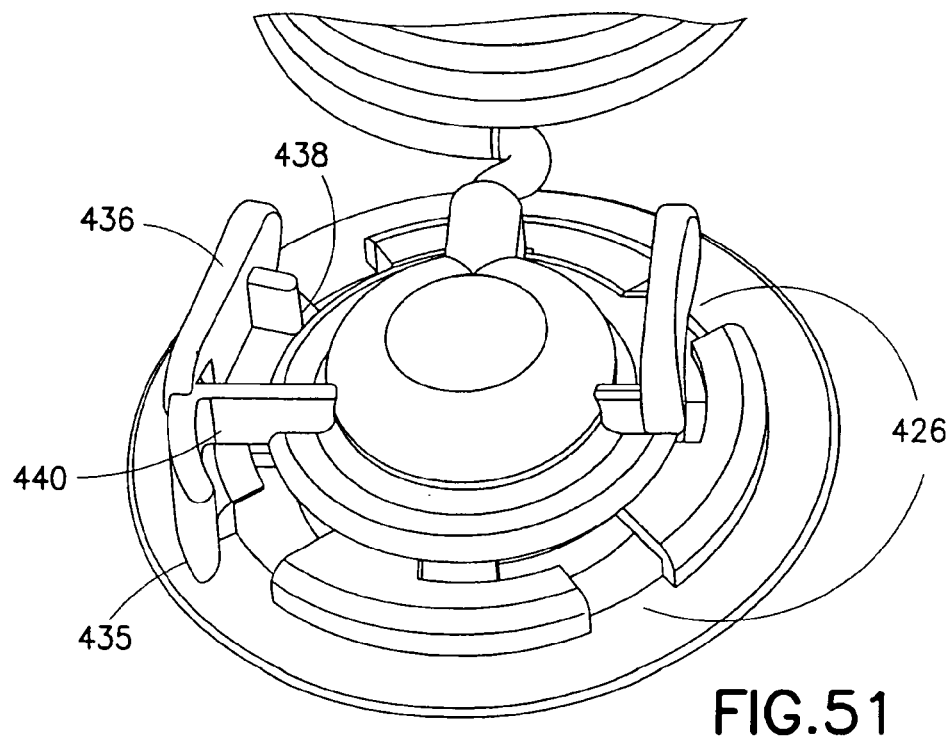

The set top can also incorporate the features described above to secure an operational position of the set top or tube set connector. In an exemplary embodiment, the set top can include a latch 435 as shown in FIGS. 48-51. When the extension set top 432 and latch 435 are brought into engagement with the base 14 as shown in FIG. 48, a chamfered lead-in area 430 can be provided to deflect the latch 435 around the base 14 as shown in FIGS. 48 and 49. Subsequent rotation of the extension set top 432 relative to the base 14 will bring the latch 435 into engagement with one of the base slots 426 to rotatably secure the extension set top 432 with the base 14 as shown in FIGS. 50 and 51. When the user wishes to disconnect the extension set from the base, pressure applied to the button 436 of the extension set top will rotate the latch 435 out of the engagement with the base slot 426, and the extension set top 432 can then be rotated to disconnect it from the base 14. A stop 438 can be employed to limit the travel of the button and latch, such that the molded pivot 440 will not become over-stressed.

The disclosed embodiments can achieve the desired functions of an interlock described above without additional components and assemblies. However, in these and other embodiments of the present invention, additional parts can be employed rather than molded-in parts and pivots as shown.

Figure 52:
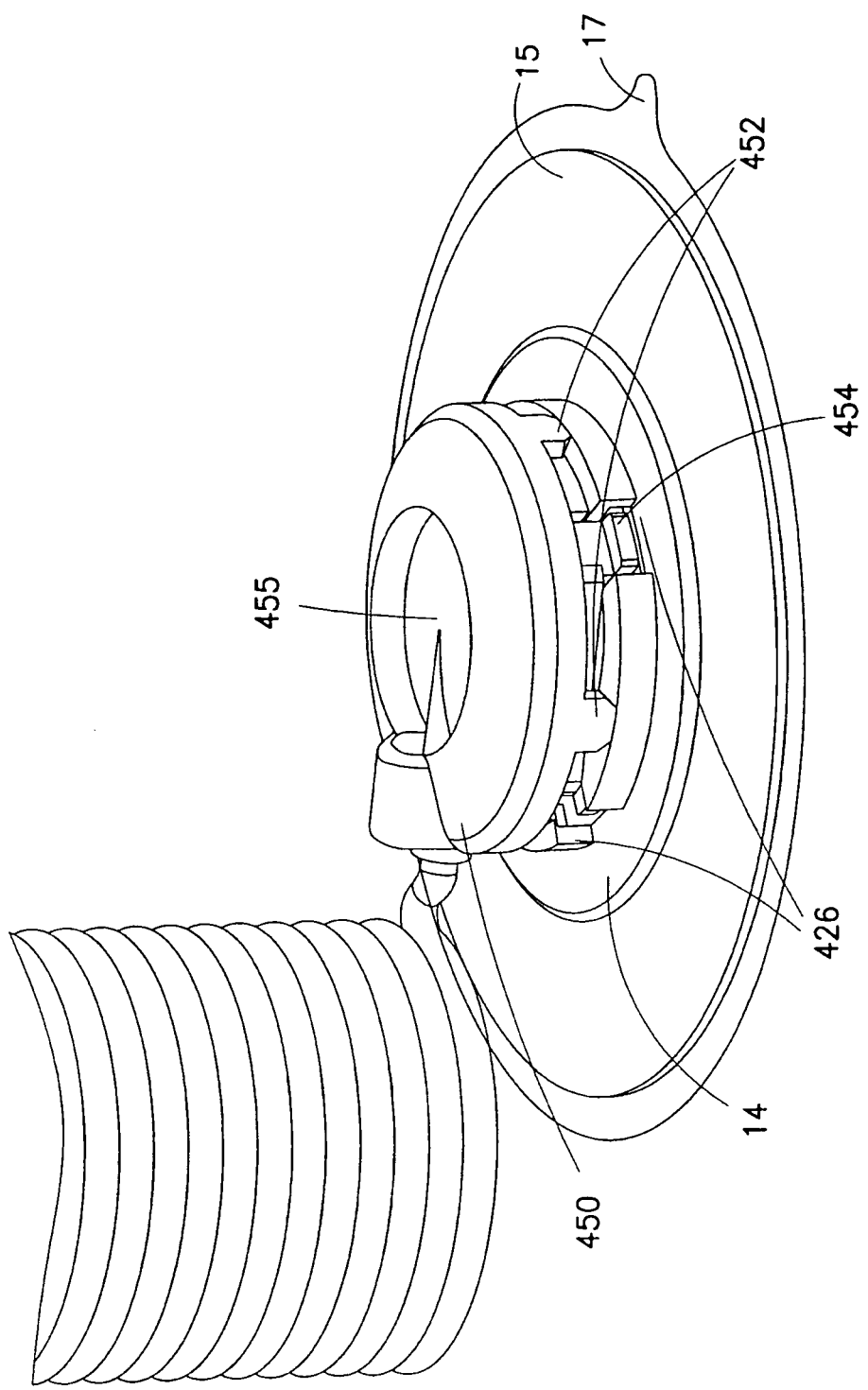
FIGS. 52-60 illustrate views of a secondary interlock for use with the above or other embodiments of the present invention.
Figure 60:
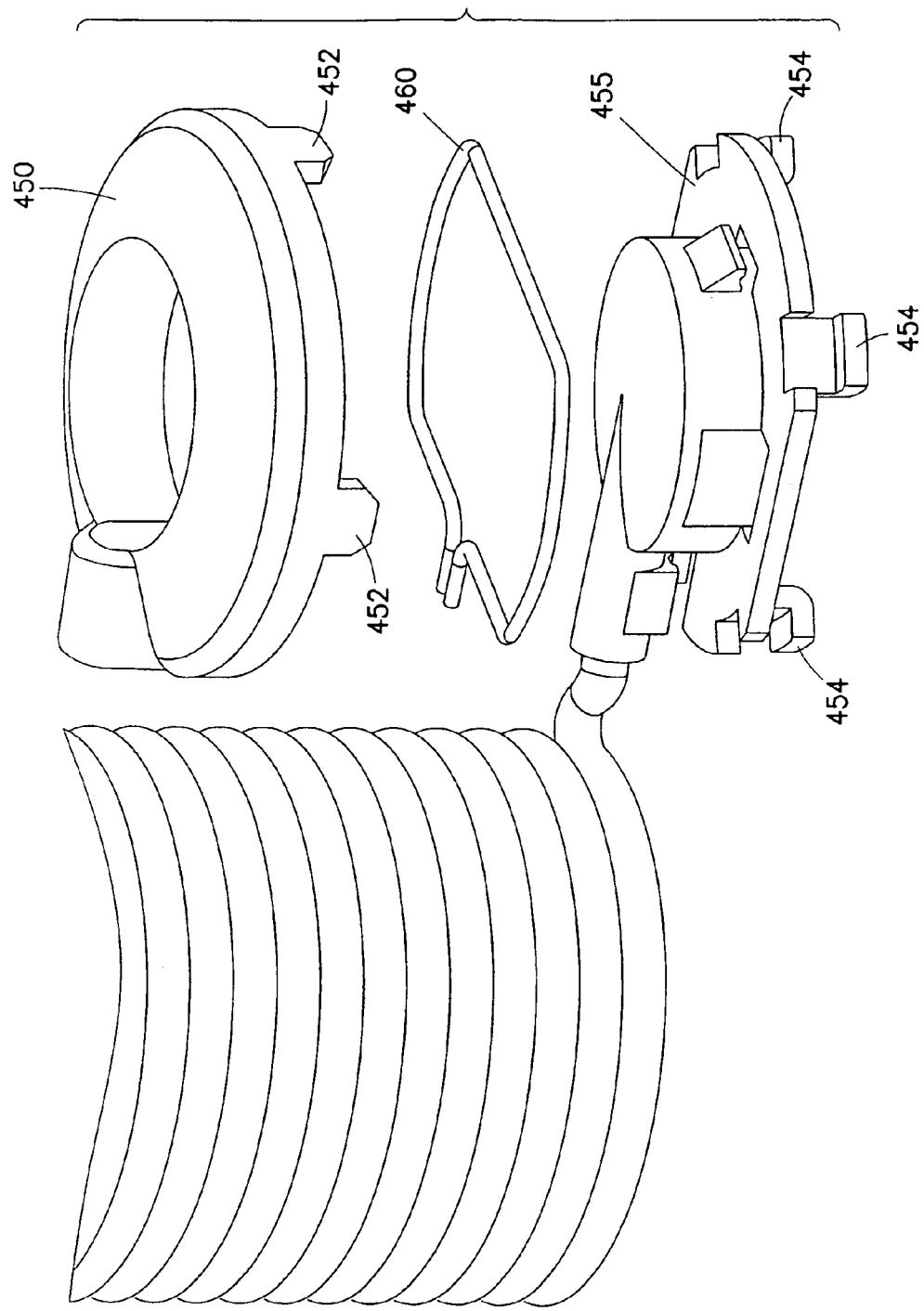

In yet another embodiment of the present invention, such a manually-activated interlock can be designed to prevent separation of the extension set from the base in the embodiments described above. In such embodiments, there may also be a concern that users can accidentally rotate the extension set top relative to the base, potentially disengaging the extension set top interlock tabs and allow the extension set to separate from the base. This can break the fluid path from the pump, and interrupt the flow of insulin to the patient. Accordingly, embodiments of the present invention can provide a secondary interlock for the extension set top and base in order to prevent disconnection. As shown in FIGS. 52 and 60, a lock ring 450 having one or more lock ring tabs 452, extension set top 455, and a lock ring spring 460 can be added to the design to prevent disconnection.

Figure 53:
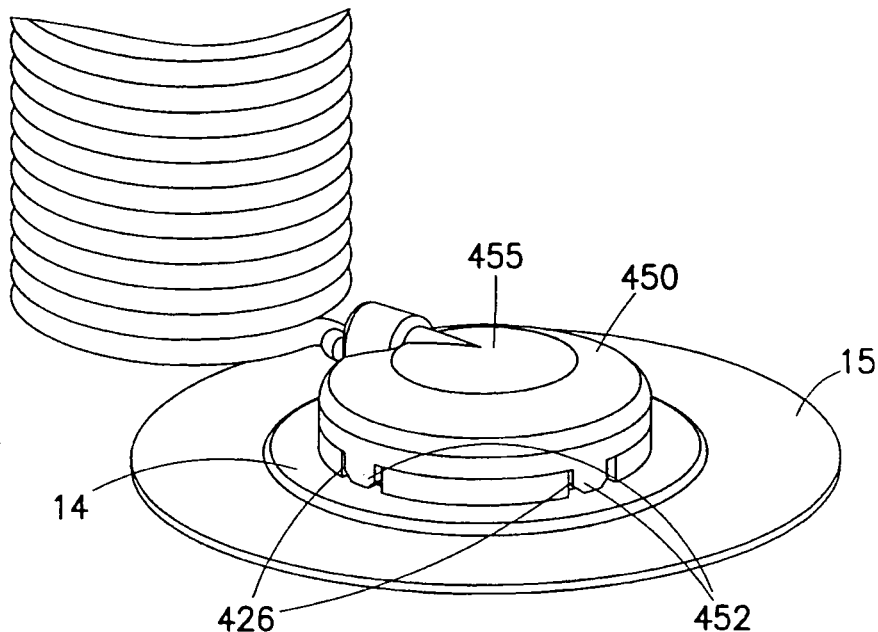
Figure 54:
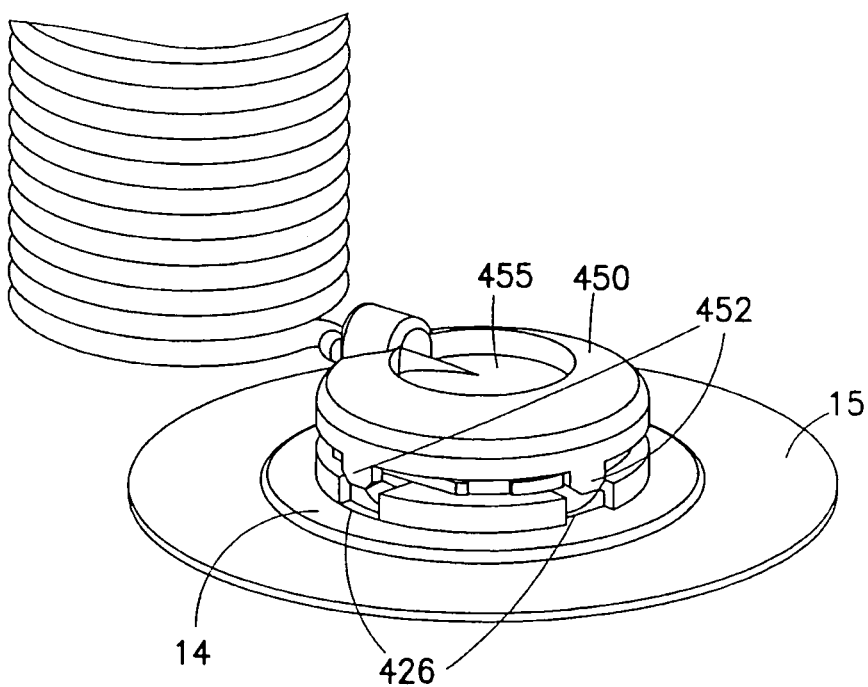
Figure 55:
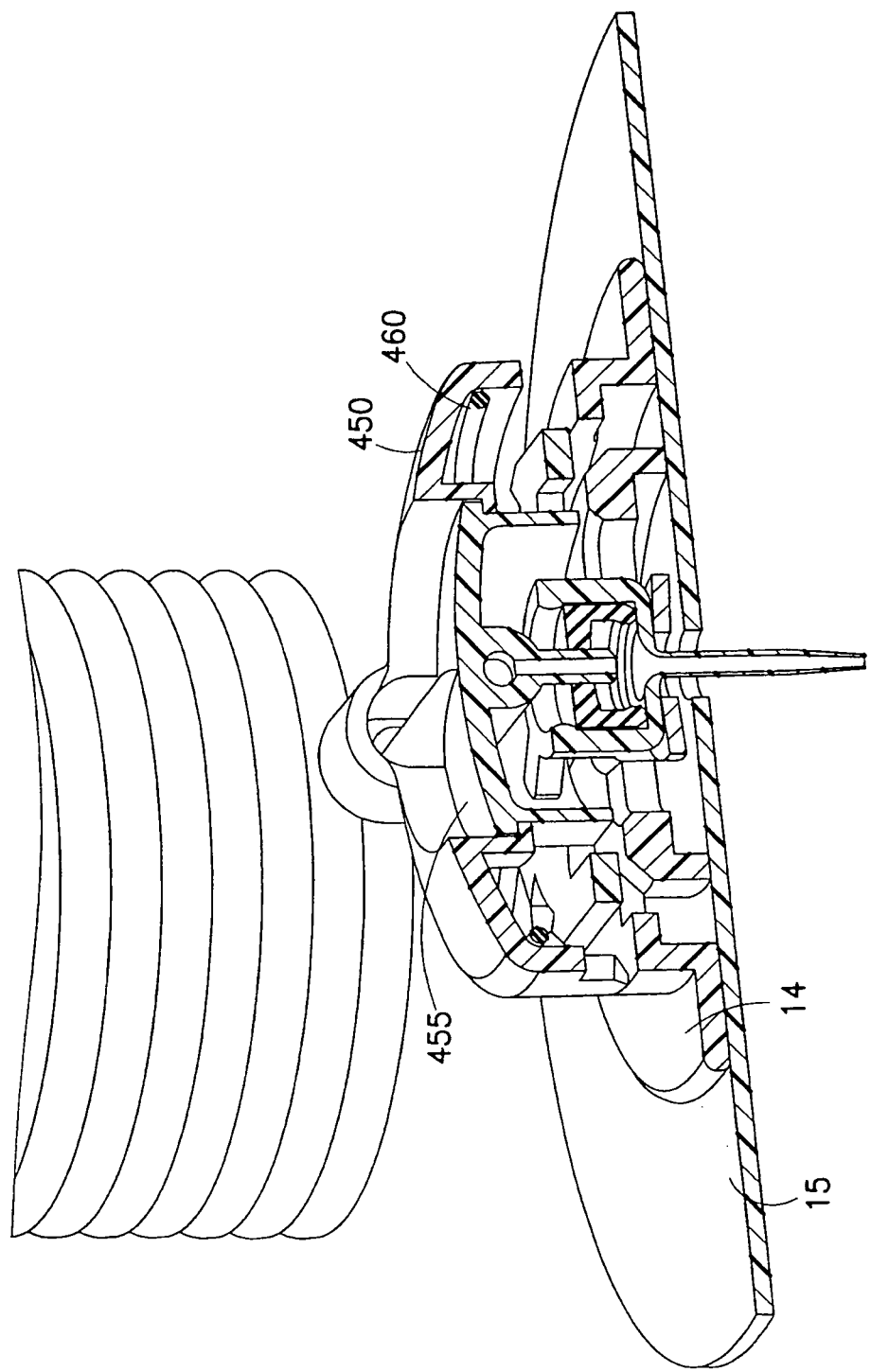
Figure 56:
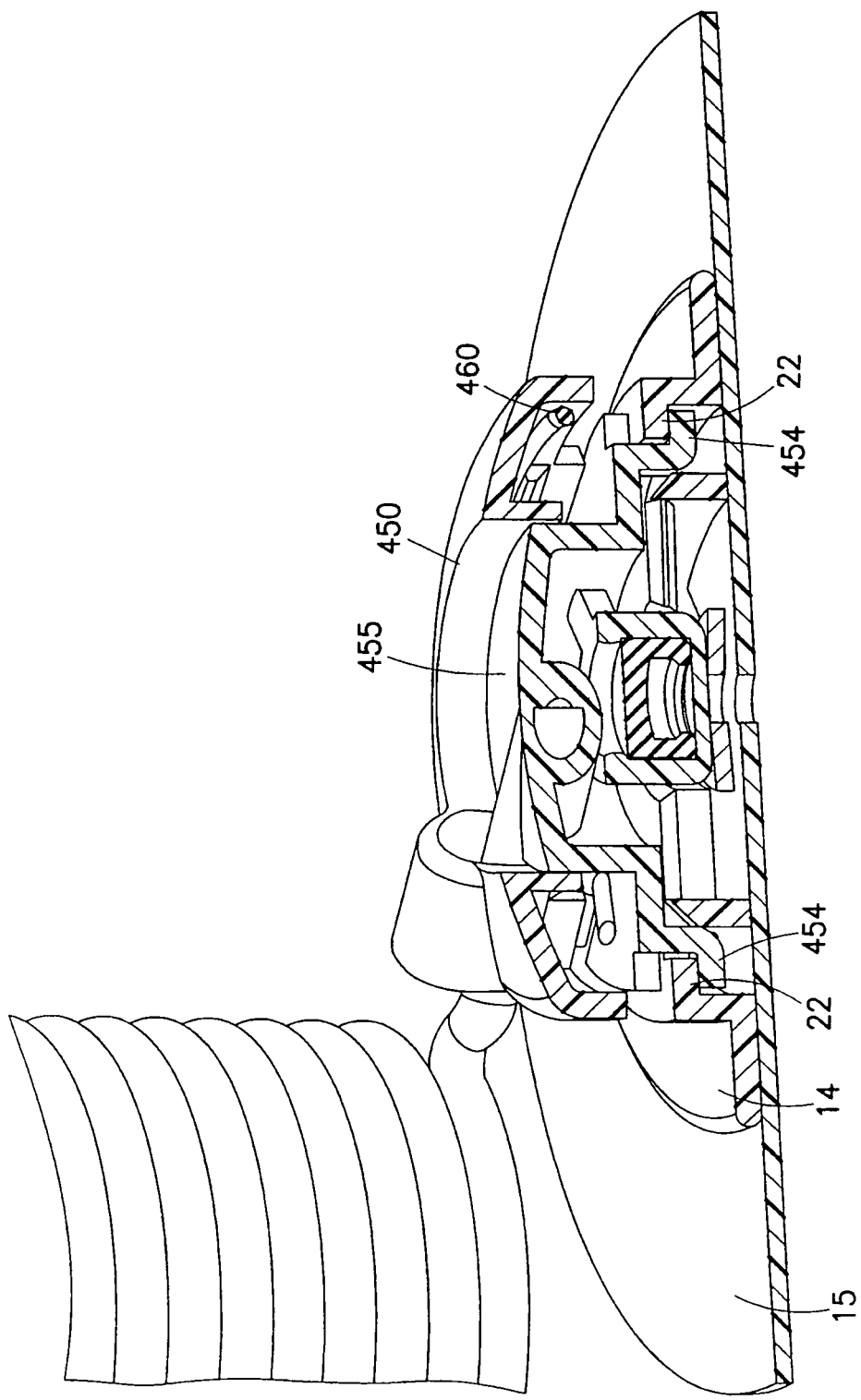

The rotatable lock ring 450 can be provided with lock ring lock tabs 452 that are designed to drop into base slots 426 once the extension set top 455 has moved into the correct locking position with the base 14. Upon installation, the user aligns the extension set top interlock tabs 454 with the base slots 426 as shown in FIGS. 52 and 55, and presses down on the center dome of the extension set top 455 as shown in FIG. 52. This moves the extension set top 455 down relative to the lock ring 450, which bears on the upper surface of the base 14 as shown in FIG. 52. Once the extension set top locking tabs 454 are pressed into the slots 426 in the base 14, the extension set top 455 and lock ring 450 can be rotated until the extension set top interlock tabs 454 lock with shoulders 22 of the base 14, and the lock ring tabs 452 drop into the base slots 426 as urged by the lock ring spring 460 as shown in FIG. 53. The extension set top 455 and locking ring 450 are now prevented from further rotation, thereby securing the extension set top 455 to the base 14 by means of the extension set top interlock tabs 454.

Figure 57:
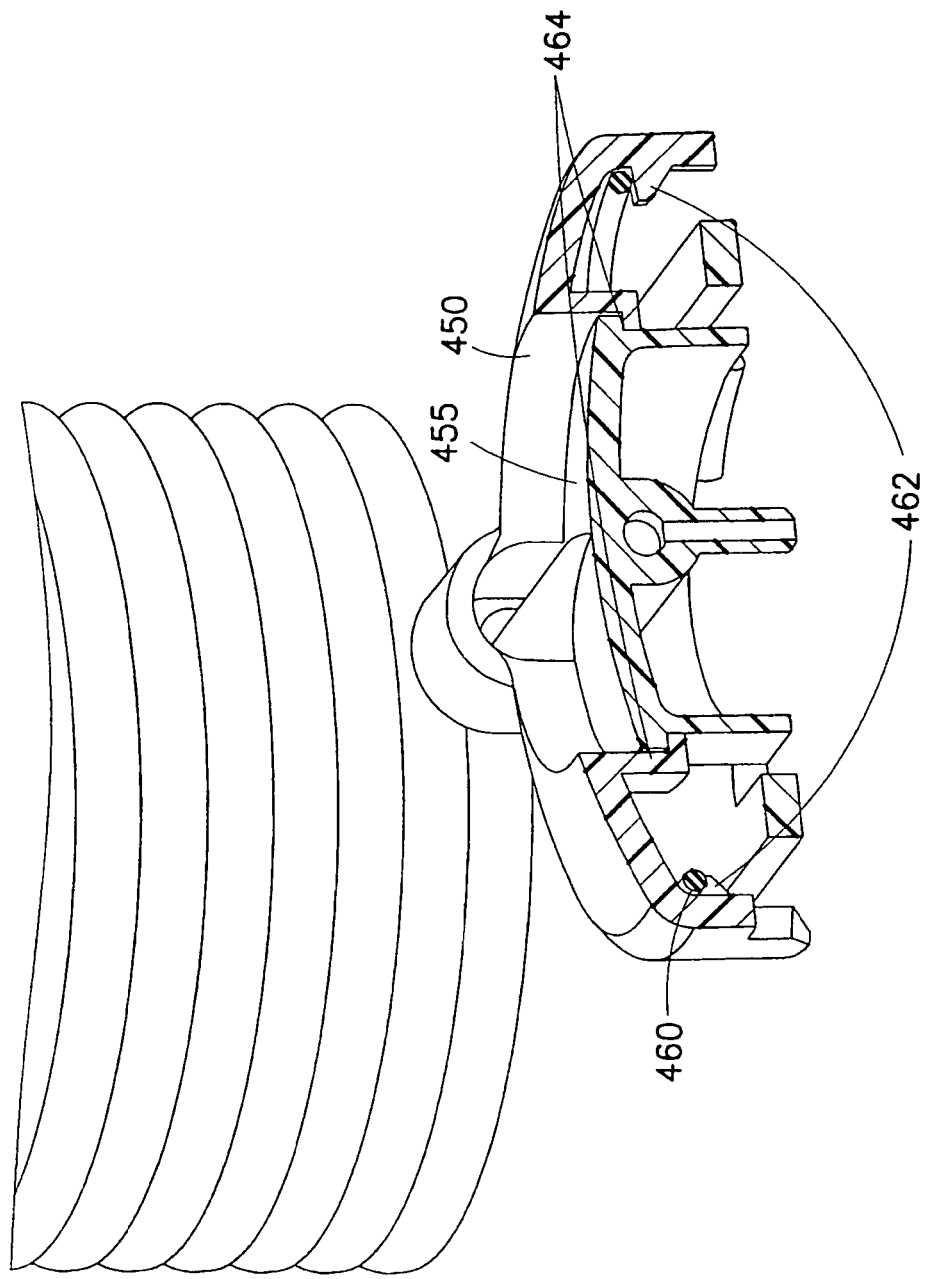
Figure 58:
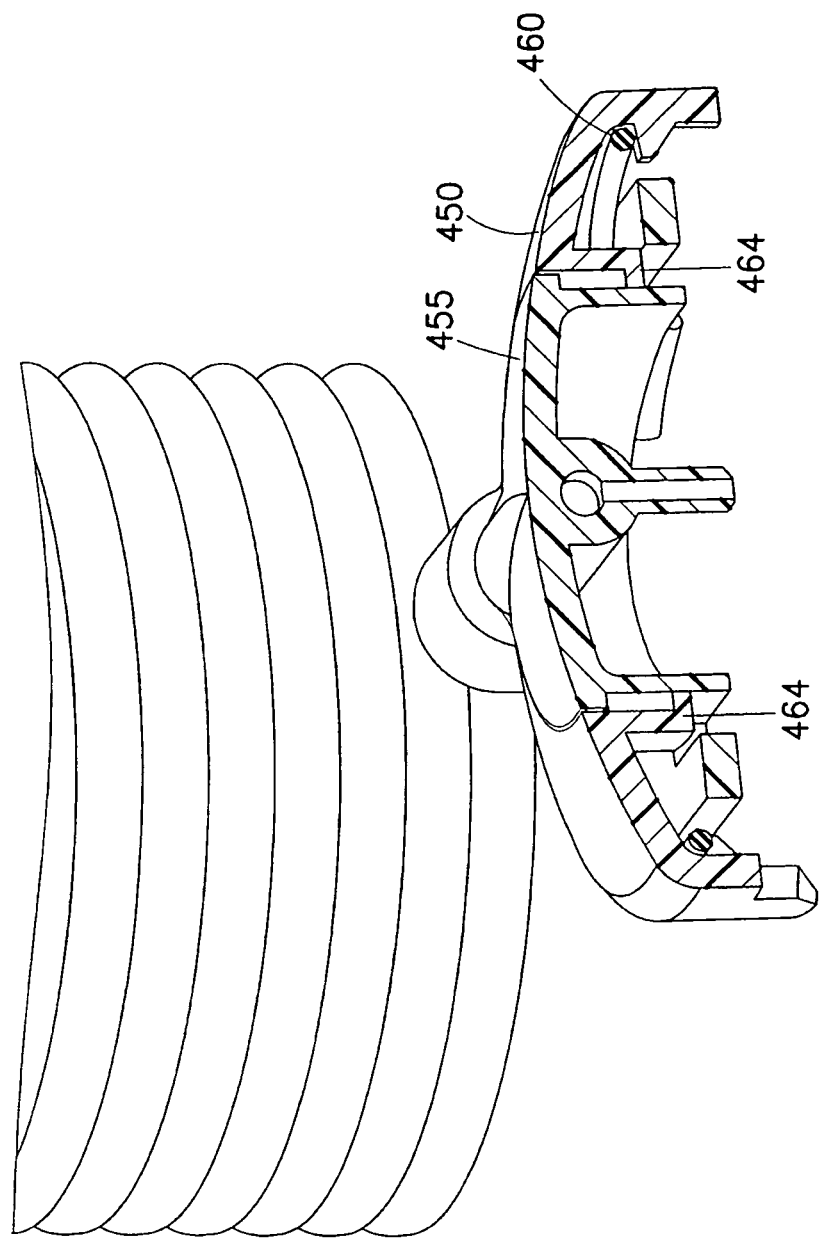
Figure 59:
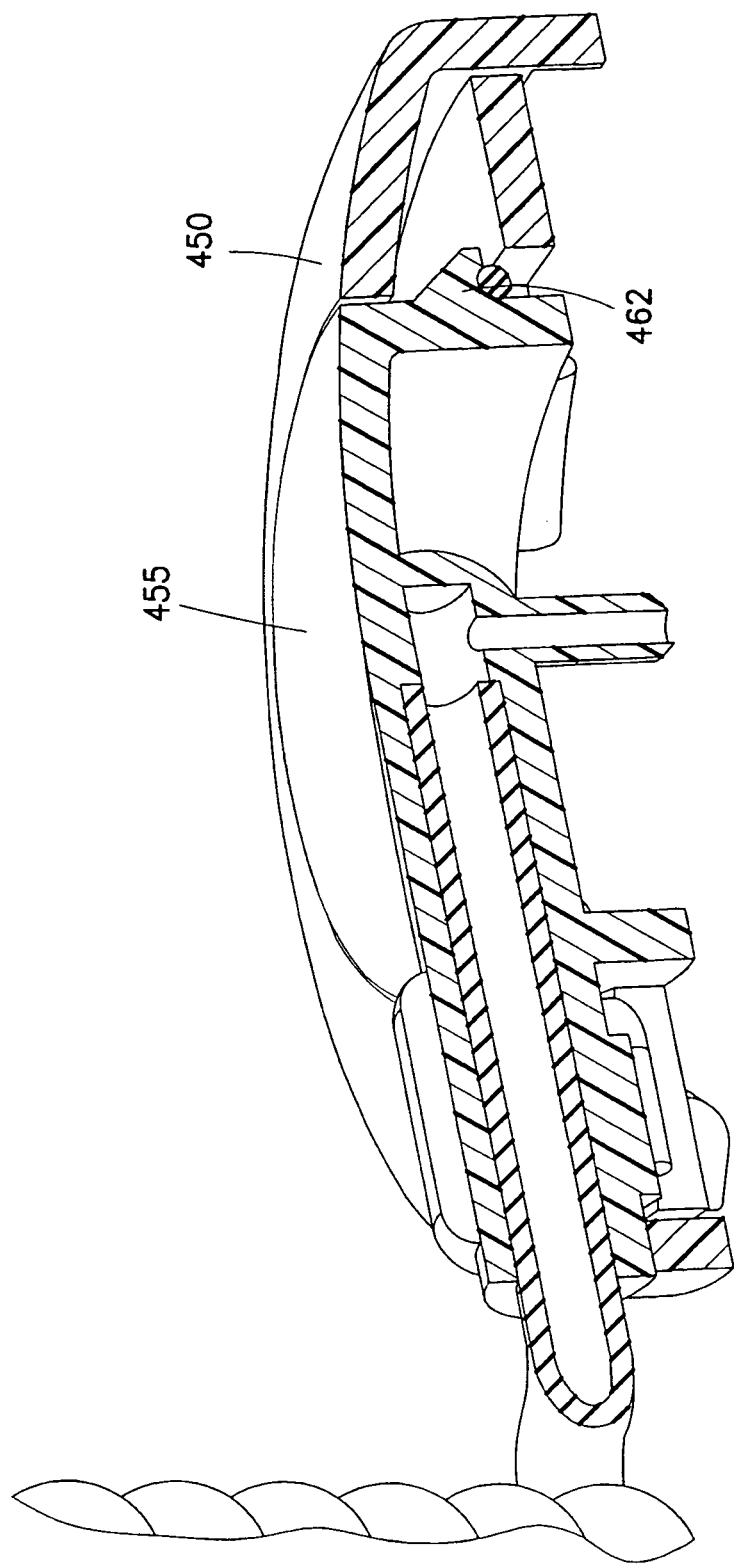

When the user needs to remove the extension set from the base, such as when swimming or showering, the user grasps the lock ring 450 and lifts it away from the base 14, then rotates the extension set top 455 until the extension set top interlock tabs 454 disengage from the base 14 as shown in FIG. 55, and removes the extension set. FIGS. 57-59 show the lock ring spring 460 and its retention feature in greater detail, and FIG. 60 is an exploded view of the embodiment. As shown in FIG. 57, the lock ring spring 460 is held within the locking ring 450 by a retention feature that comprises a shoulder 462 on an inner circumference of the lock ring 450. The lock ring 450 is held with the extension set top 455 by a retention feature that comprises a shoulder engagement 464 with the extension set top 455.

The disclosed embodiments can achieve the desired functions of an interlock described above with a more ergonomic interlock between the extension set and the base. In yet another embodiment of the present invention, a package 500 as shown in FIG. 61 can be provided that encloses the integrated/removable inserter, and shields the activation and removal buttons. This allows placement of the device in a manner that prevents premature activation of these buttons.

One or more of the above or other exemplary devices can comprise the activation button 16 on the top of the device, so that when the user places the device on the skin prior to activation, there is an ease of access and minimal requirement for dexterity to activate the button. However, in such cases, there is a possibility that the device can be activated unintentionally, and therefore, a package 500 as described below is used to fully protect at least the buttons 16 and 428 from activation during handling and placement of the device.

Figure 63:
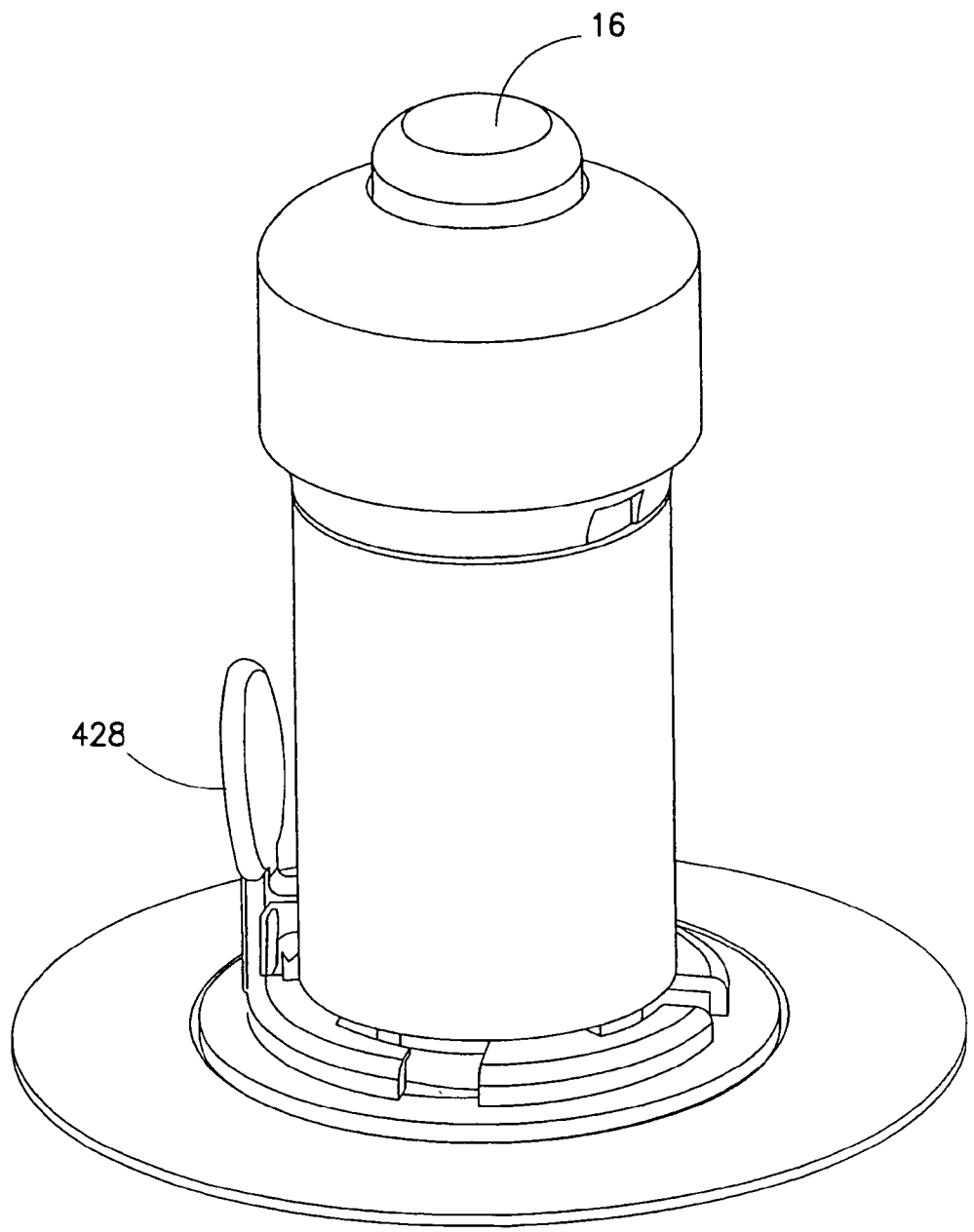

Accordingly, a package 500 is provided wherein at least the buttons 16 and 428 are shielded by the package. The device within the package 500 can be provided with a skin contacting adhesive layer such as a pressure sensitive adhesive (PSA), and an adhesive cover as described above. The adhesive layer cover of the infusion device and the package seal are integrated into a single, combined adhesive layer/package opening cover 504 with a user-graspable pull-tab 505. In addition to sealing the package and covering the adhesive of the device, the combined cover 504 is used to cover one or more pockets of the package 500 for other components related to filling and dispensing. FIG. 61 shows in transparency a small package 500 for enclosing and shrouding the buttons 16 and 428 of an embodiment as described above, and providing large, smooth handling surfaces 502. FIG. 62 shows the device of FIG. 61 with the package seal and/or adhesive cover 504 removed such that the device within the package can be placed on the skin surface and ready for activation of the buttons 16 and 428 once the package is removed from the device as shown in FIG. 63. Once the device is adhesively secured to the skin surface, the package can be lifted away.

FIG. 64 is a sectional view to illustrate the device of FIG. 61 in greater detail, including retention snaps 506 within an opening of the package 500 for engaging the device therein and releasably securing the device within the package. The snaps 506 can be configured to engage a surface of the device, or can correspond to detents or other profile features of the device contained therein. The exemplary device contained within the package can comprise any number of embodiments, such as those described above. FIG. 65 shows the device of FIG. 64 with the skin adhesive layer 508 exposed after removal of the package seal and/or release liner 504 using pull tab 505.

Figure 66:
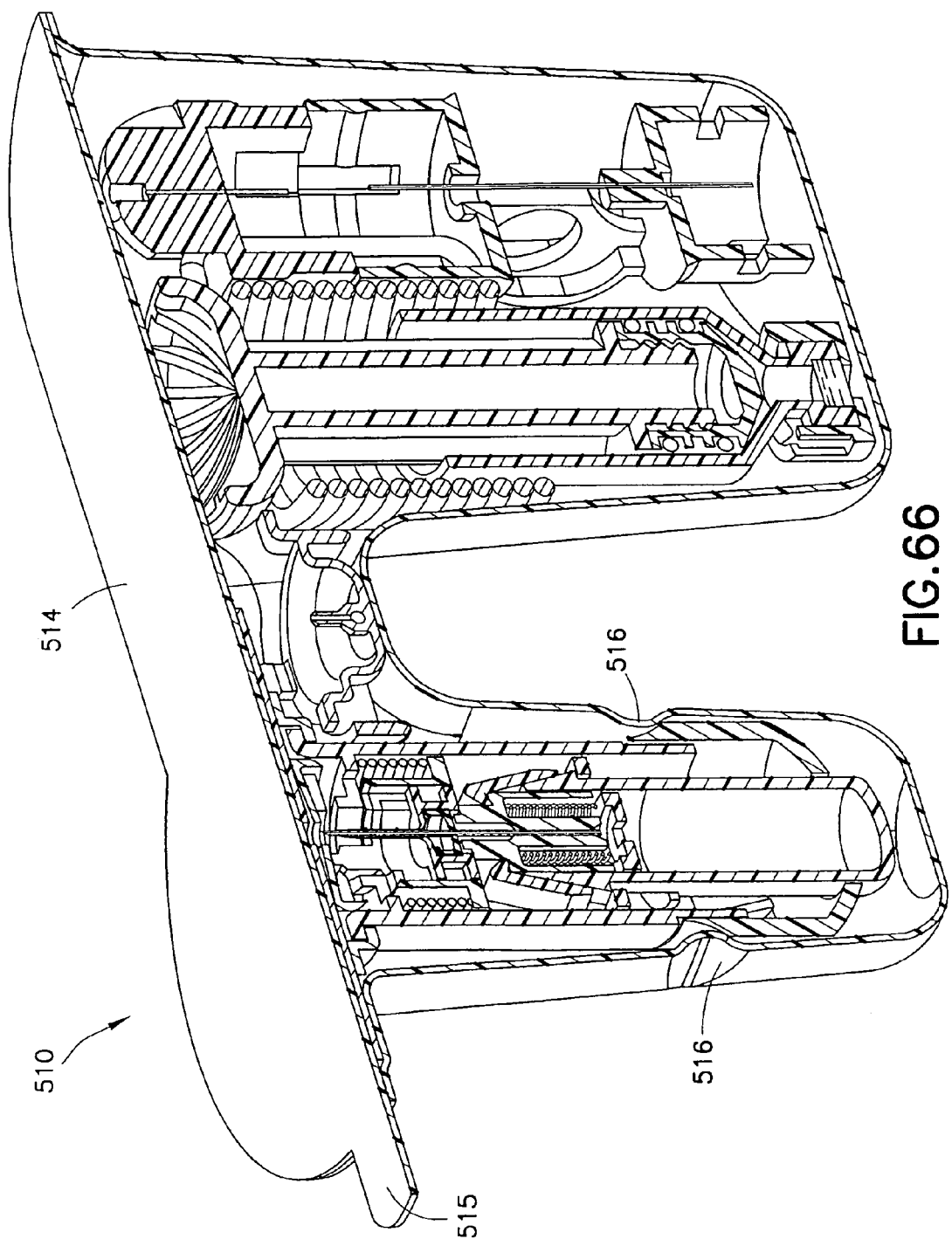
Figure 67:
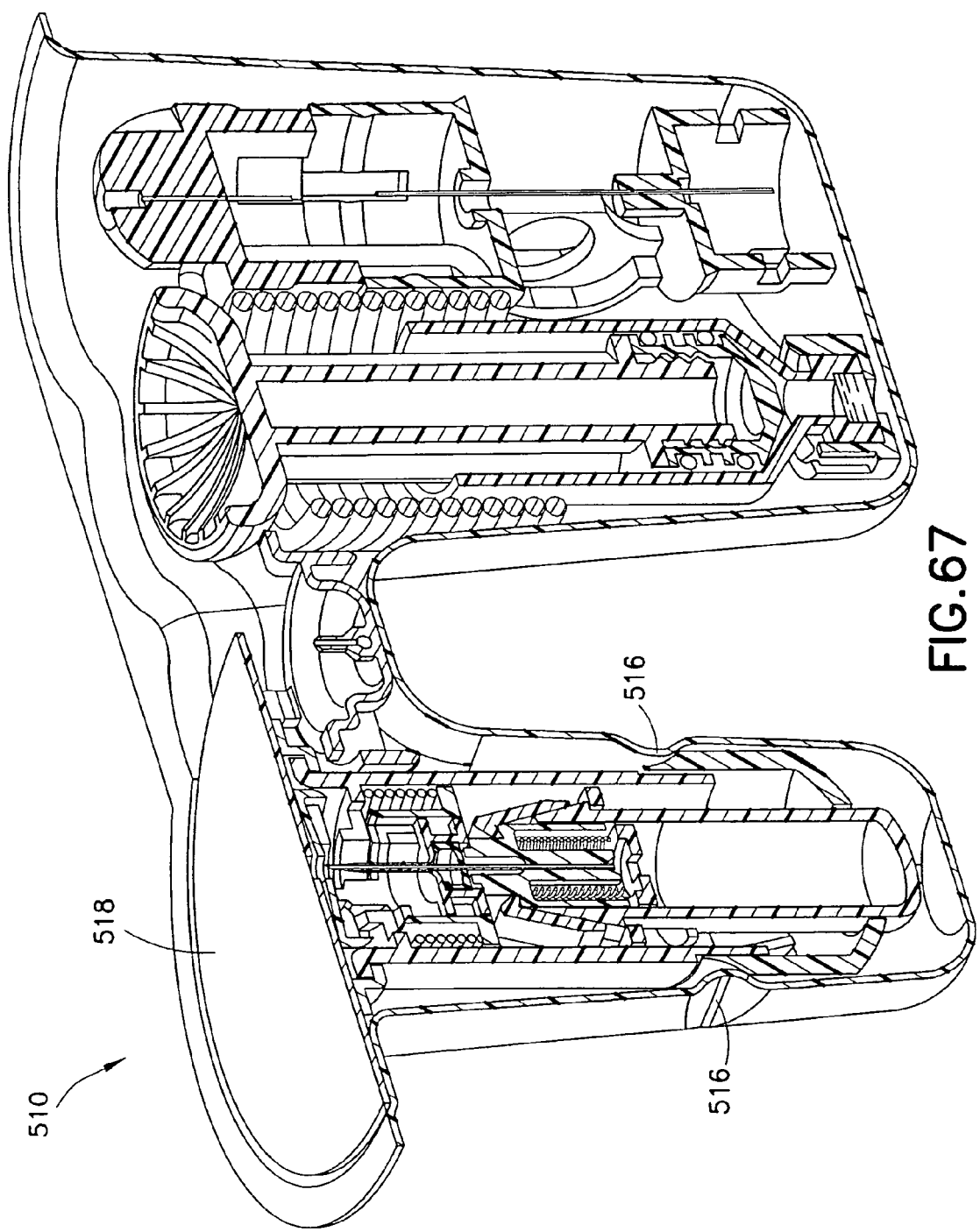

FIG. 66 shows another embodiment of the present invention substantially as described above, but further comprising one or more additional pockets for other components related to filling and dispensing. This embodiment comprises a larger package design 510 with the filling and dispensing components in a sample configuration. As noted above, the package 510 can also comprise a package seal integrated into a single, combined adhesive layer/package opening cover 514 with a user-graspable pull-tab 515, and retention snaps 516 within an opening of the package 510 for engaging the devices therein and releasably securing the devices within the package. FIG. 67 shows the device of FIG. 66 with the package seal/adhesive release liner removed exposing the adhesive layer 518.

In these embodiments, when the package seal and/or skin adhesive release liner is removed, the device can be placed on the skin surface, without removing it from the package, allowing placement without the possibility of premature button activation. The package retention snaps 506 and 516 are incorporated into the package 500 and 510 to maintain the devices in the package until the user is ready to activate the inserter, at which time the user may squeeze the package, such as at a 90 degree angle relative to the snaps, to open the snaps and allow the package to be lifted from the device, leaving the integrated/removable inserter on the user's skin surface.

As shown in FIGS. 66 and 67, the package 510 can include one or more additional cavities for the insulin reservoir, reservoir filling and dispensing components, and extension set tubing and connections. By integrating the package seal and adhesive release liner, the number of steps to open the device in preparation for placing the catheter is minimized. Further, in one embodiment, the catheter extension set, reservoir, and reservoir filling and dispensing components, are integrated into a single package for user convenience. Further, in the embodiment configured as a smaller package, there is a greater ease in placement. In the embodiment configured as a larger package, there is the convenience of having all of the components readily available for the subsequent steps of connecting the infusion pump.

Accordingly, concerns regarding devices having a button on top that may be prematurely activated during placement of the device on the skin surface can be minimized. The package further provides a sterile barrier which can also serve as the skin adhesive release liner to reduce steps. The package also protects the activation button during placement, after which the package is removed from the device by pressing the sides to release the undercut snaps. Further, the package can be configured to house other elements, for example, the insulin reservoir and extension set.

Although only a few exemplary embodiments of the present invention have been described in detail above, those skilled in the art will readily appreciate that many modifications are possible in the disclosed embodiments without materially departing from the novel teachings and advantages of the present invention. Accordingly, all such modifications are intended to be included within the scope of the invention as defined in the appended claims and their equivalents.

The invention claimed is:

1. An infusion device, comprising:
an inserter for inserting a catheter into a skin surface, said inserter comprising an infusion device housing, said infusion device housing comprising a catheter and driver for inserting said catheter into a skin surface;
an infusion device base for rotatably securing thereon said infusion device housing, said infusion device base comprising at least one adhesive layer for releasably securing said infusion device base with said skin surface; and
an introducer needle and a hub, wherein said driver comprises a push button configured to travel substantially perpendicular to said skin surface and rotate said hub into a release position; wherein the infusion device housing is rotatable relative to the infusion device base and wherein:

said hub comprises a retention sear, and said infusion device housing comprises a cam slot for slidably receiving said retention sear and for rotating said infusion device housing relative to said hub into said release position as said push button is pressed.

2. The infusion device as claimed in claim 1, further comprising:

a drive spring to drive said introducer needle and said catheter into said skin surface when said hub is rotated into said release position.

3. The infusion device as claimed in claim 1, wherein said driver is configured to release from said base and retract said introducer needle when rotated.

4. The infusion device as claimed in claim 1, further comprising a deflectable latch to prevent rotation of said infusion device housing relative to said infusion device base.

5. The infusion device as claimed in claim 1, further comprising:

a tube set connector; and a deflectable latch to prevent rotation of said tube set connector relative to said infusion device base.

6. The infusion device as claimed in claim 1, further comprising a stabilizer extending from said catheter.

7. The infusion device as claimed in claim 1, further comprising:

a packaging element for receiving said infusion device housing, wherein at least one side of said packaging element comprises said infusion device base.

8. The infusion device as claimed in claim 7, wherein said packaging element comprises at least one detent to releasably secure said infusion device housing.

* * * * *